United States Patent
Frey et al.

(10) Patent No.: US 12,365,705 B2
(45) Date of Patent: Jul. 22, 2025

(54) EPITOPE TAGS RECOGNIZED BY SPECIFIC BINDERS

(71) Applicant: NANOTAG BIOTECHNOLOGIES GmbH, Goettingen (DE)

(72) Inventors: Steffen Frey, Gottingen (DE); Hansjoerg Goetzke, Hannover (DE); Davilla Luis Felipe Opazo, Goettingen (DE); Paal Erik Gustav Stenmark, Jaerfaella (SE); Carranza Markel Martinez, Stockholm (SE)

(73) Assignee: NANOTAG BIOTECHNOLOGIES GmbH, Goettingen (DE)

( * ) Notice: Subject to any disclaimer, the term of this patent is extended or adjusted under 35 U.S.C. 154(b) by 1166 days.

(21) Appl. No.: 17/274,755

(22) PCT Filed: Sep. 11, 2019

(86) PCT No.: PCT/EP2019/074153
§ 371 (c)(1),
(2) Date: Mar. 11, 2021

(87) PCT Pub. No.: WO2020/053239
PCT Pub. Date: Mar. 19, 2020

(65) Prior Publication Data
US 2022/0048947 A1    Feb. 17, 2022

(30) Foreign Application Priority Data
Sep. 11, 2018 (EP) ..................... 18193663
Mar. 4, 2019 (EP) ..................... 19160485

(51) Int. Cl.
*A61K 38/00* (2006.01)
*C07K 7/08* (2006.01)
*C07K 14/435* (2006.01)

(52) U.S. Cl.
CPC .............. *C07K 7/08* (2013.01); *C07K 14/435* (2013.01); *C07K 14/43595* (2013.01); *C07K 2319/40* (2013.01)

(58) Field of Classification Search
CPC ............ C07K 14/435; C07K 14/43595; C07K 14/705; C07K 16/2854; C07K 16/44; C07K 2317/21; C07K 2317/22; C07K 2317/34; C07K 2317/569; C07K 2317/622; C07K 2317/80; C07K 2317/92; C07K 2319/03; C07K 2319/33; C07K 2319/40; C07K 7/04; C07K 7/08
See application file for complete search history.

(56) References Cited

U.S. PATENT DOCUMENTS

2017/0107302 A1 *   4/2017   Silence ................... A61P 29/00

FOREIGN PATENT DOCUMENTS

| WO | WO94/04678 | 3/1993 |
| WO | WO2003052076 A2 * | 12/2002 |
| WO | WO03/052076 | 6/2003 |

OTHER PUBLICATIONS

Office Action for Japanese Application 2021-537505, dated Aug. 16, 2023, 4 pages.
Office Action for Japanese Application 2021-537505, dated Aug. 16, 2023, 4 pages (English translation).
Loftus et al., The Genome of the Basidiomycetous Yeast and Human Pathogen Crytococcus neofformans, Science, Feb. 25, 2005, 1321-1324.
Petukhov, M. et al., "Design of Stable A-Helices Using Global Sequence Optimization", J. Peptide Science (2009) 15, 359-365.
Braun, M. et al., "Peptides in Headlock—A Novel High Affinity and Versatile Peptide-Binding Nanobody" (2016) 6, 1-10.
Goetzke, H. et al., "Teh Alfa-Tag is a Highly Versatile Tool for Nanobody-Based Bioscience Applications" (2019) 10, 1-12.
International Search Report for PCT/EP2019/074153 (WO2020053239A1), Dec. 16, 2019, 3 Pages.

* cited by examiner

*Primary Examiner* — Aradhana Sasan
*Assistant Examiner* — Mercy H Sabila
(74) *Attorney, Agent, or Firm* — SCI-LAW STRATEGIES, PC

(57) ABSTRACT

The present invention provides peptides useful as epitope tags, which may be fused to a polypeptide of interest, as well as antibodies that specifically bind to these peptides. The peptides and/or antibodies can be used for detecting, immobilizing, isolating or purifying a molecule that is conjugated to such a peptide and/or antibody.

13 Claims, 18 Drawing Sheets

Specification includes a Sequence Listing.

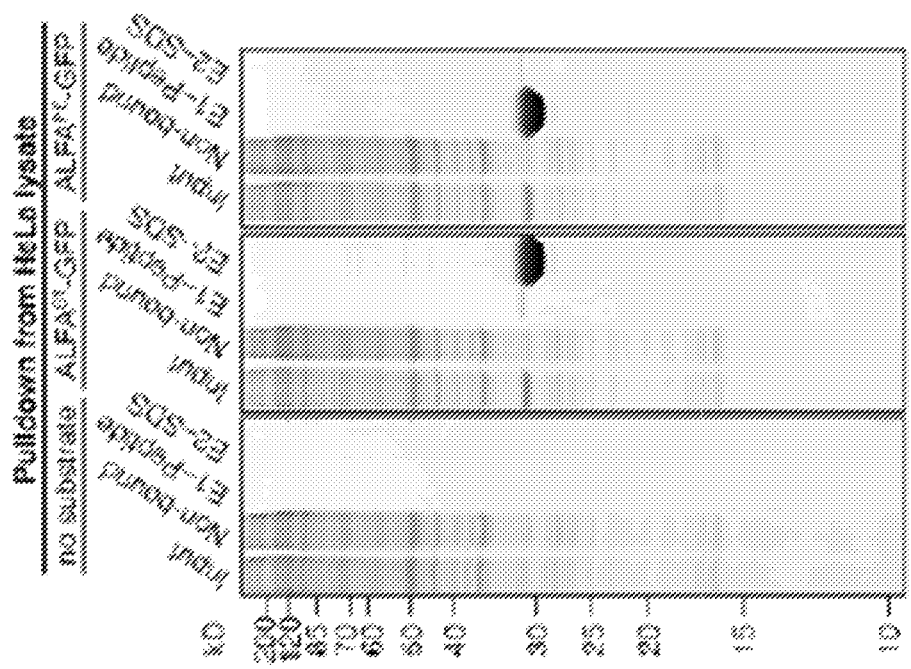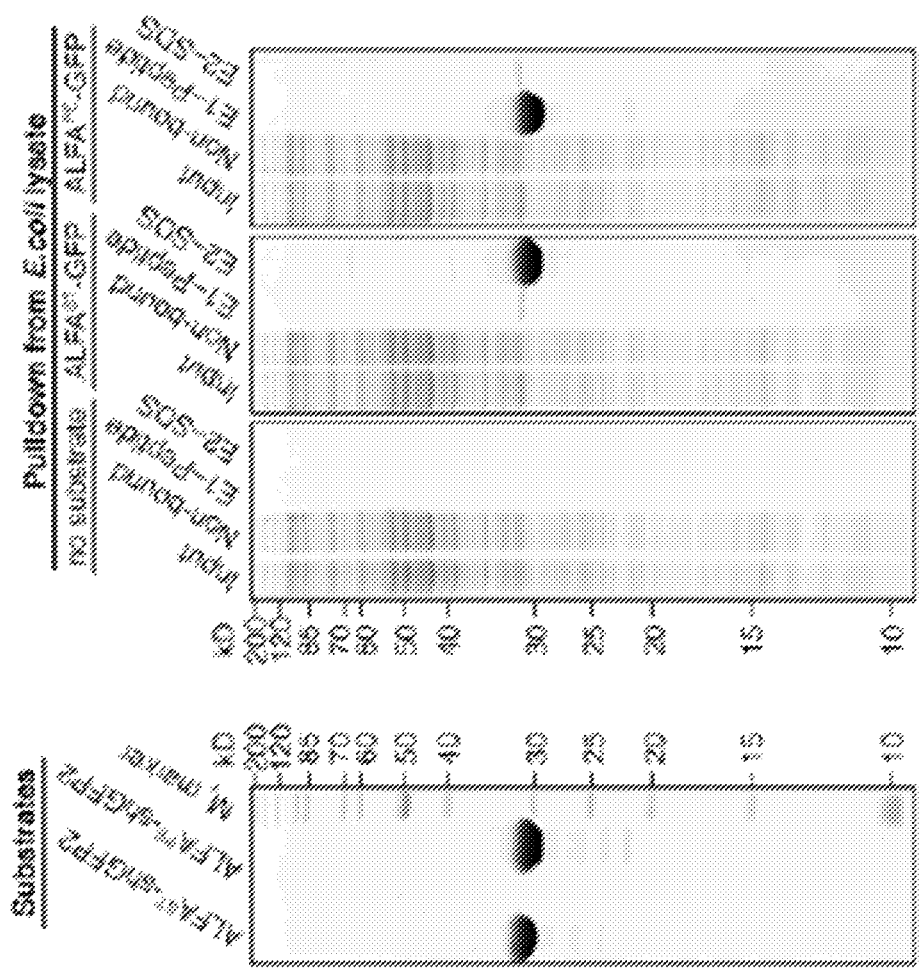

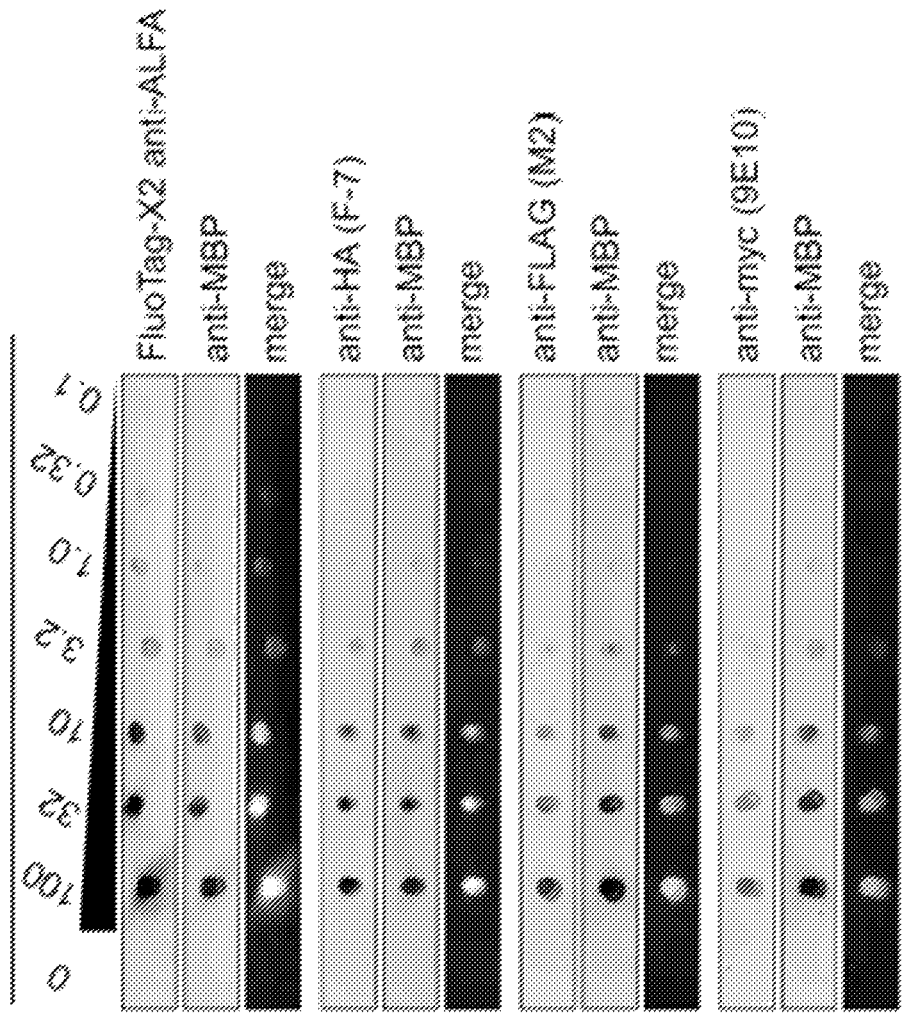
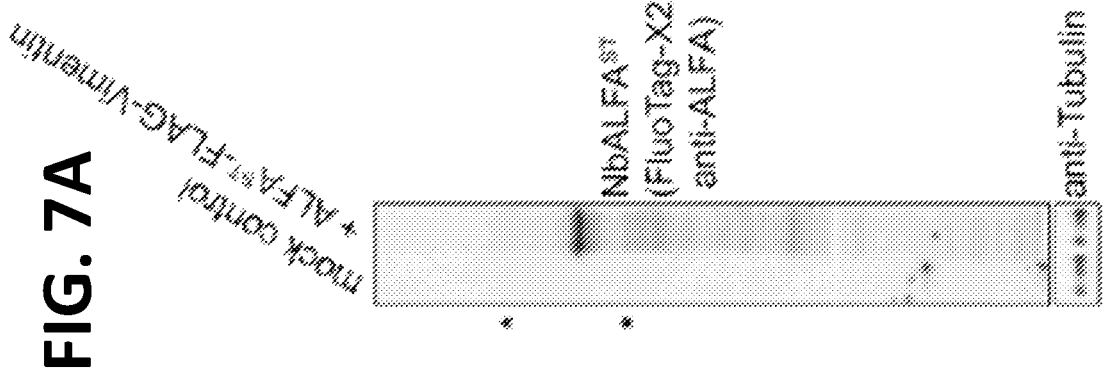
FIG. 7A
FIG. 7B

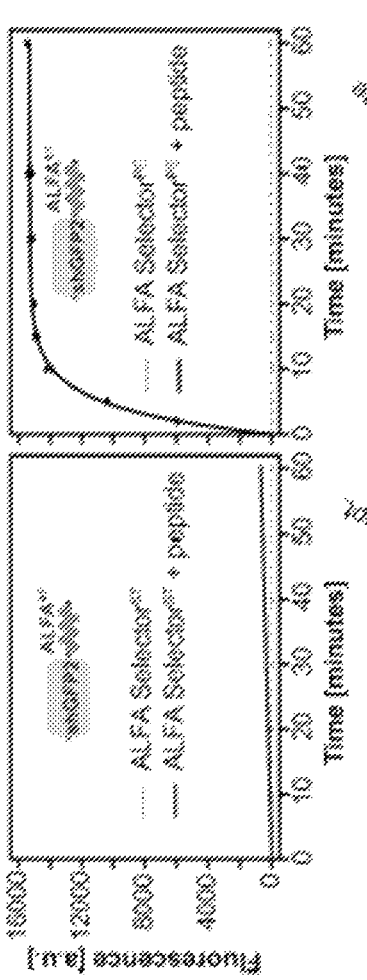
FIG. 8A
FIG. 8B
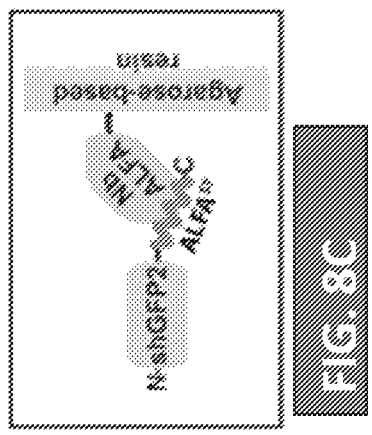
FIG. 8C
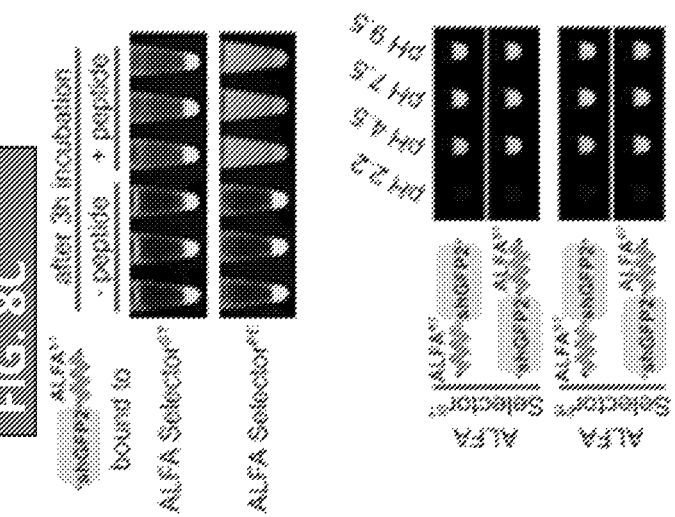
FIG. 8D

SEQUENCE LISTING

<160> NUMBER OF SEQ ID NOS: 199

<210> SEQ ID NO 1
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 1

Xaa Xaa Xaa Xaa Xaa Xaa Xaa Xaa Xaa Arg Leu Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is G or S or P or T
<220> FEATURE:
<221> NAME/KEY: MISC_FEATURE
<222> LOCATION: (2)..(2)
<223> OTHER INFORMATION: Xaa is R or G or P
<220> FEATURE:
<221> NAME/KEY: MISC_FEATURE
<222> LOCATION: (5)..(5)
<223> OTHER INFORMATION: Xaa is E or Q
<220> FEATURE:
<221> NAME/KEY: MISC_FEATURE
<222> LOCATION: (7)..(7)
<223> OTHER INFORMATION: Xaa is L or I
<220> FEATURE:
<221> NAME/KEY: MISC_FEATURE
<222> LOCATION: (12)..(12)
<223> OTHER INFORMATION: Xaa is S or T or P or A or D or E
<220> FEATURE:
<221> NAME/KEY: MISC_FEATURE
<222> LOCATION: (13)..(13)
<223> OTHER INFORMATION: Xaa is P or A or S or A or D or E or no amino
      acid

<400> SEQUENCE: 2

Xaa Xaa Leu Glu Xaa Glu Xaa Arg Arg Arg Leu Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is S or T
<220> FEATURE:
<221> NAME/KEY: MISC_FEATURE
<222> LOCATION: (2)..(2)
<223> OTHER INFORMATION: Xaa is R or G
<220> FEATURE:
<221> NAME/KEY: MISC_FEATURE
<222> LOCATION: (5)..(5)

```
<223> OTHER INFORMATION: Xaa is E or Q
<220> FEATURE:
<221> NAME/KEY: MISC_FEATURE
<222> LOCATION: (12)..(12)
<223> OTHER INFORMATION: Xaa is T or D or E
<220> FEATURE:
<221> NAME/KEY: MISC_FEATURE
<222> LOCATION: (13)..(13)
<223> OTHER INFORMATION: Xaa is A or D or E or no amino acid

<400> SEQUENCE: 3

Xaa Xaa Leu Glu Xaa Glu Leu Arg Arg Arg Leu Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: synthetic peptide

<400> SEQUENCE: 4

Ser Arg Leu Glu Glu Glu Leu Arg Arg Arg Leu Thr Glu
1               5                   10

<210> SEQ ID NO 5
<211> LENGTH: 16
<212> TYPE: PRT
<213> ORGANISM: Artificial Sequence
<220> FEATURE:
<223> OTHER INFORMATION: synthetic peptide

<400> SEQUENCE: 5

Met Pro Ser Arg Leu Glu Glu Glu Leu Arg Arg Arg Leu Thr Glu Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Pro Ser Arg Leu Glu Glu Glu Leu Arg Arg Arg Leu Thr Glu Pro
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: synthetic peptide

<400> SEQUENCE: 7

Pro Ser Arg Leu Glu Glu Glu Leu Arg Arg Arg Leu Thr Glu
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic peptide

<400> SEQUENCE: 8

Gly Arg Ser Arg Leu Glu Glu Glu Leu Arg Arg Arg Leu Thr Ala
1               5                   10                  15
```

```
<210> SEQ ID NO 9
<211> LENGTH: 16
<212> TYPE: PRT
<213> ORGANISM: Artificial Sequence
<220> FEATURE:
<223> OTHER INFORMATION: synthetic peptide

<400> SEQUENCE: 9

Pro Gly Ser Arg Leu Glu Glu Glu Leu Arg Arg Arg Leu Thr Ala Pro
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetic peptide

<400> SEQUENCE: 10

Pro Ser Thr Arg Leu Glu Glu Glu Leu Arg Arg Arg Leu Thr Ala Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic peptide

<400> SEQUENCE: 11

Ser Pro Ser Arg Leu Glu Glu Glu Leu Arg Arg Arg Leu Thr Ala Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is G or S or T or P
<220> FEATURE:
<221> NAME/KEY: MISC_FEATURE
<222> LOCATION: (2)..(2)
<223> OTHER INFORMATION: Xaa is R or G or A or E or P
<220> FEATURE:
<221> NAME/KEY: MISC_FEATURE
<222> LOCATION: (3)..(3)
<223> OTHER INFORMATION: Xaa is L or V
<220> FEATURE:
<221> NAME/KEY: MISC_FEATURE
<222> LOCATION: (4)..(4)
<223> OTHER INFORMATION: Xaa is E or Q
<220> FEATURE:
<221> NAME/KEY: MISC_FEATURE
<222> LOCATION: (5)..(5)
<223> OTHER INFORMATION: Xaa is E or Q
<220> FEATURE:
<221> NAME/KEY: MISC_FEATURE
<222> LOCATION: (6)..(6)
<223> OTHER INFORMATION: Xaa is E or Q
<220> FEATURE:
<221> NAME/KEY: MISC_FEATURE
<222> LOCATION: (7)..(7)
<223> OTHER INFORMATION: Xaa is L or I or V
<220> FEATURE:
<221> NAME/KEY: MISC_FEATURE
<222> LOCATION: (8)..(8)
<223> OTHER INFORMATION: Xaa is R or A or Q or E
```

```
<220> FEATURE:
<221> NAME/KEY: MISC_FEATURE
<222> LOCATION: (9)..(9)
<223> OTHER INFORMATION: Xaa is R or A or Q or E
<220> FEATURE:
<221> NAME/KEY: MISC_FEATURE
<222> LOCATION: (12)..(12)
<223> OTHER INFORMATION: Xaa is S or T or D or E or P or A or no amino
      acid
<220> FEATURE:
<221> NAME/KEY: MISC_FEATURE
<222> LOCATION: (13)..(13)
<223> OTHER INFORMATION: Xaa is E or K or P or S or A or D or no amino
      acid

<400> SEQUENCE: 12

Ser Pro Ser Arg Leu Glu Glu Glu Leu Arg Arg Arg Leu Asp Ala Pro
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

Ser Pro Ser Arg Leu Glu Glu Glu Leu Arg Arg Arg Leu Glu Ala Pro
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: synthetic peptide

<400> SEQUENCE: 14

Ser Pro Ser Arg Leu Glu Glu Glu Leu Arg Arg Arg Leu Thr Asp Pro
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic peptide

<400> SEQUENCE: 15

Ser Pro Ser Arg Leu Glu Glu Glu Leu Arg Arg Arg Leu Thr Glu Pro
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: synthetic peptide

<400> SEQUENCE: 16

Ser Pro Ser Arg Leu Glu Glu Glu Leu Arg Arg Arg Leu Thr Ala Asp
1               5                   10                  15

Pro

<210> SEQ ID NO 17
<211> LENGTH: 16
<212> TYPE: PRT
<213> ORGANISM: Artificial Sequence
```

```
<220> FEATURE:
<223> OTHER INFORMATION: synthetic peptide

<400> SEQUENCE: 17

Ser Pro Ser Gly Leu Glu Glu Glu Leu Arg Arg Arg Leu Thr Glu Pro
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: synthetic peptide

<400> SEQUENCE: 18

Gly Pro Ser Arg Leu Glu Glu Glu Leu Arg Arg Arg Leu Thr
1               5                   10

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

Gly Pro Ser Arg Leu Glu Glu Glu Leu Arg Arg Arg Leu Thr Ala
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: synthetic peptide

<400> SEQUENCE: 20

Gly Pro Ser Arg Leu Glu Glu Glu Leu Arg Arg Arg Leu Thr Ala Ala
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: synthetic peptide

<400> SEQUENCE: 21

Gly Pro Ser Arg Leu Glu Glu Glu Leu Arg Arg Arg Leu Thr Ala Ala
1               5                   10                  15

Ser

<210> SEQ ID NO 22
<211> LENGTH: 16
<212> TYPE: PRT
<213> ORGANISM: Artificial Sequence
<220> FEATURE:
<223> OTHER INFORMATION: synthetic peptide

<400> SEQUENCE: 22

Ser Pro Ser Gly Leu Glu Gln Glu Leu Arg Arg Arg Leu Thr Ala Pro
1               5                   10                  15

<210> SEQ ID NO 23
<211> LENGTH: 16
<212> TYPE: PRT
```

<213> ORGANISM: Artificial Sequence
<220> FEATURE:
<223> OTHER INFORMATION: synthetic peptide

<400> SEQUENCE: 23

Ser Pro Ser Gly Leu Glu Gln Glu Leu Arg Arg Arg Leu Asp Ala Pro
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: synthetic peptide

<400> SEQUENCE: 24

Ser Pro Ser Gly Leu Glu Gln Glu Leu Arg Arg Arg Leu Glu Ala Pro
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: synthetic peptide

<400> SEQUENCE: 25

Ser Pro Ser Gly Leu Glu Gln Glu Leu Arg Arg Arg Leu Thr Glu Pro
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic peptide

<400> SEQUENCE: 26

Gly Pro Ser Arg Leu Glu Glu Glu Leu Arg Arg Arg Leu Thr Ala Pro
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: synthetic peptide

<400> SEQUENCE: 27

Gly Pro Ser Arg Leu Glu Glu Glu Leu Arg Arg Arg Leu Thr Glu Pro
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Gly Pro Ser Arg Leu Glu Glu Glu Leu Arg Arg Arg Leu Thr Glu
1               5                   10                  15

<210> SEQ ID NO 29
<211> LENGTH: 15
<212> TYPE: PRT
<213> ORGANISM: Artificial Sequence

```
<220> FEATURE:
<223> OTHER INFORMATION: synthetic peptide

<400> SEQUENCE: 29

Met Ser Arg Leu Glu Glu Glu Leu Arg Arg Arg Leu Thr Glu Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: synthetic peptide

<400> SEQUENCE: 30

Met Ser Ser Arg Leu Glu Glu Glu Leu Arg Arg Arg Leu Thr Glu Pro
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is G or S or P
<220> FEATURE:
<221> NAME/KEY: MISC_FEATURE
<222> LOCATION: (2)..(2)
<223> OTHER INFORMATION: Xaa is R or G
<220> FEATURE:
<221> NAME/KEY: MISC_FEATURE
<222> LOCATION: (5)..(5)
<223> OTHER INFORMATION: Xaa is E or Q
<220> FEATURE:
<221> NAME/KEY: MISC_FEATURE
<222> LOCATION: (7)..(7)
<223> OTHER INFORMATION: Xaa is L or I
<220> FEATURE:
<221> NAME/KEY: MISC_FEATURE
<222> LOCATION: (12)..(12)
<223> OTHER INFORMATION: Xaa is S or T or P or A
<220> FEATURE:
<221> NAME/KEY: MISC_FEATURE
<222> LOCATION: (13)..(13)
<223> OTHER INFORMATION: Xaa is P or A or S or no amino acid

<400> SEQUENCE: 31

Xaa Xaa Leu Glu Xaa Glu Xaa Arg Arg Arg Leu Xaa Xaa
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic peptide

<400> SEQUENCE: 32

Gly Arg Leu Glu Glu Glu Leu Arg Arg Arg Leu Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: synthetic peptide
```

<400> SEQUENCE: 33

Met Ser Gly Arg Leu Glu Glu Glu Leu Arg Arg Arg Leu Ser Pro
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: synthetic peptide

<400> SEQUENCE: 34

Ser Asp Ser Gly Leu Glu Gln Glu Leu Arg Arg Arg Leu Ser Pro Gly
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: synthetic peptide

<400> SEQUENCE: 35

Pro Asp Gly Gly Leu Glu Gln Glu Leu Arg Arg Arg Leu Thr Ala Pro
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: synthetic peptide

<400> SEQUENCE: 36

Pro Ser Gly Gly Leu Glu Gln Glu Leu Arg Arg Arg Leu Thr Ala Pro
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: synthetic peptide

<400> SEQUENCE: 37

Asp Ser Pro Gly Leu Glu Gln Glu Leu Arg Arg Arg Leu Thr Ala Pro
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: synthetic peptide

<400> SEQUENCE: 38

Pro Asp Ser Gly Leu Glu Gln Glu Leu Arg Arg Arg Leu Thr Pro Ala
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: synthetic peptide

<400> SEQUENCE: 39

```
Ser Pro Ser Gly Leu Glu Glu Glu Leu Arg Arg Arg Leu Thr Ala Glu
1               5                   10                  15

Pro

<210> SEQ ID NO 40
<211> LENGTH: 14
<212> TYPE: PRT
<213> ORGANISM: Artificial Sequence
<220> FEATURE:
<223> OTHER INFORMATION: synthetic peptide

<400> SEQUENCE: 40

Gly Pro Ser Gly Leu Glu Gln Glu Leu Arg Arg Arg Leu Thr
1               5                   10

<210> SEQ ID NO 41
<211> LENGTH: 17
<212> TYPE: PRT
<213> ORGANISM: Artificial Sequence
<220> FEATURE:
<223> OTHER INFORMATION: synthetic peptide

<400> SEQUENCE: 41

Gly Pro Ser Gly Leu Glu Gln Glu Leu Arg Arg Arg Leu Thr Ala Ala
1               5                   10                  15

Ser

<210> SEQ ID NO 42
<211> LENGTH: 16
<212> TYPE: PRT
<213> ORGANISM: Artificial Sequence
<220> FEATURE:
<223> OTHER INFORMATION: synthetic peptide

<400> SEQUENCE: 42

Ser Pro Ser Arg Leu Glu Glu Glu Leu Arg Arg Arg Leu Pro Ser Lys
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: synthetic peptide

<400> SEQUENCE: 43

Ser Pro Ser Gly Leu Glu Gln Glu Leu Arg Arg Arg Leu Thr Pro Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: synthetic peptide

<400> SEQUENCE: 44

Ser Pro Gly Arg Leu Glu Gln Glu Ile Arg Arg Arg Leu Ser Pro Ser
1               5                   10                  15

<210> SEQ ID NO 45
<211> LENGTH: 16
<212> TYPE: PRT
<213> ORGANISM: Artificial Sequence
<220> FEATURE:
```

<223> OTHER INFORMATION: synthetic peptide

<400> SEQUENCE: 45

Pro Ser Gly Arg Leu Glu Glu Glu Leu Arg Arg Arg Leu Ser Pro Ser
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: synthetic peptide

<400> SEQUENCE: 46

Pro Ser Gly Arg Leu Glu Glu Glu Leu Arg Arg Arg Leu Ser
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic peptide

<400> SEQUENCE: 47

Pro Ser Gly Arg Leu Glu Glu Glu Leu Arg Arg Arg Leu Ala
1               5                   10

<210> SEQ ID NO 48
<211> LENGTH: 15
<212> TYPE: PRT
<213> ORGANISM: Artificial Sequence
<220> FEATURE:
<223> OTHER INFORMATION: synthetic peptide

<400> SEQUENCE: 48

Pro Ser Gly Arg Leu Glu Glu Glu Leu Arg Arg Arg Leu Ser Pro
1               5                   10                  15

<210> SEQ ID NO 49
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is S or G or P
<220> FEATURE:
<221> NAME/KEY: MISC_FEATURE
<222> LOCATION: (2)..(2)
<223> OTHER INFORMATION: Xaa is R or G or P
<220> FEATURE:
<221> NAME/KEY: MISC_FEATURE
<222> LOCATION: (5)..(5)
<223> OTHER INFORMATION: Xaa is E or Q
<220> FEATURE:
<221> NAME/KEY: MISC_FEATURE
<222> LOCATION: (12)..(12)
<223> OTHER INFORMATION: Xaa is S or T or D or E
<220> FEATURE:
<221> NAME/KEY: MISC_FEATURE
<222> LOCATION: (13)..(13)
<223> OTHER INFORMATION: Xaa is P or A or D or no amino acid

<400> SEQUENCE: 49

Xaa Xaa Leu Glu Xaa Glu Leu Arg Arg Arg Leu Xaa Xaa
1               5                   10

```
<210> SEQ ID NO 50
<211> LENGTH: 16
<212> TYPE: PRT
<213> ORGANISM: Artificial Sequence
<220> FEATURE:
<223> OTHER INFORMATION: synthetic peptide

<400> SEQUENCE: 50

Pro Asp Ser Gly Leu Glu Gln Glu Leu Arg Arg Arg Leu Ser Pro Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: synthetic peptide

<400> SEQUENCE: 51

Pro Asp Ser Gly Leu Glu Gln Glu Leu Arg Arg Arg Leu Thr Ala Pro
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: synthetic peptide

<400> SEQUENCE: 52

Pro Ser Ser Gly Leu Glu Gln Glu Leu Arg Arg Arg Leu Thr Ala Pro
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: synthetic peptide

<400> SEQUENCE: 53

Asp Pro Ser Gly Leu Glu Gln Glu Leu Arg Arg Arg Leu Thr Ala Pro
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: synthetic peptide

<400> SEQUENCE: 54

Asp Ser Gly Pro Leu Glu Gln Glu Leu Arg Arg Arg Leu Thr Ala Pro
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: synthetic peptide

<400> SEQUENCE: 55

Ser Pro Ser Arg Leu Glu Glu Glu Leu Arg Arg Arg Leu Thr Ala Glu
1               5                   10                  15

Pro
```

```
<210> SEQ ID NO 56
<211> LENGTH: 16
<212> TYPE: PRT
<213> ORGANISM: Artificial Sequence
<220> FEATURE:
<223> OTHER INFORMATION: synthetic peptide

<400> SEQUENCE: 56

Ser Pro Ser Gly Leu Glu Glu Glu Leu Arg Arg Arg Leu Thr Ala Pro
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: synthetic peptide

<400> SEQUENCE: 57

Ser Pro Ser Gly Leu Glu Glu Glu Leu Arg Arg Arg Leu Asp Ala Pro
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: synthetic peptide

<400> SEQUENCE: 58

Ser Pro Ser Gly Leu Glu Glu Glu Leu Arg Arg Arg Leu Glu Ala Pro
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: synthetic peptide

<400> SEQUENCE: 59

Ser Pro Ser Gly Leu Glu Glu Glu Leu Arg Arg Arg Leu Thr Asp Pro
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: synthetic peptide

<400> SEQUENCE: 60

Ser Pro Ser Gly Leu Glu Glu Glu Leu Arg Arg Arg Leu Thr Ala Asp
1               5                   10                  15

Pro

<210> SEQ ID NO 61
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is G or S
```

```
<220> FEATURE:
<221> NAME/KEY: MISC_FEATURE
<222> LOCATION: (2)..(2)
<223> OTHER INFORMATION: Xaa is R or G or A or E
<220> FEATURE:
<221> NAME/KEY: MISC_FEATURE
<222> LOCATION: (3)..(3)
<223> OTHER INFORMATION: Xaa is L or V
<220> FEATURE:
<221> NAME/KEY: MISC_FEATURE
<222> LOCATION: (4)..(4)
<223> OTHER INFORMATION: Xaa is E or Q
<220> FEATURE:
<221> NAME/KEY: MISC_FEATURE
<222> LOCATION: (5)..(5)
<223> OTHER INFORMATION: Xaa is E or Q
<220> FEATURE:
<221> NAME/KEY: MISC_FEATURE
<222> LOCATION: (6)..(6)
<223> OTHER INFORMATION: Xaa is E or Q
<220> FEATURE:
<221> NAME/KEY: MISC_FEATURE
<222> LOCATION: (7)..(7)
<223> OTHER INFORMATION: Xaa is L or I or V
<220> FEATURE:
<221> NAME/KEY: MISC_FEATURE
<222> LOCATION: (8)..(8)
<223> OTHER INFORMATION: Xaa is R or A or Q or E
<220> FEATURE:
<221> NAME/KEY: MISC_FEATURE
<222> LOCATION: (9)..(9)
<223> OTHER INFORMATION: Xaa is R or A or Q or E
<220> FEATURE:
<221> NAME/KEY: MISC_FEATURE
<222> LOCATION: (12)..(12)
<223> OTHER INFORMATION: Xaa is S or T or L or no amino acid
<220> FEATURE:
<221> NAME/KEY: MISC_FEATURE
<222> LOCATION: (13)..(13)
<223> OTHER INFORMATION: Xaa is K or P or S or no amino acid

<400> SEQUENCE: 61

Xaa Xaa Xaa Xaa Xaa Xaa Xaa Xaa Xaa Arg Leu Xaa Xaa
1               5                   10

<210> SEQ ID NO 62
<211> LENGTH: 16
<212> TYPE: PRT
<213> ORGANISM: Artificial Sequence
<220> FEATURE:
<223> OTHER INFORMATION: synthetic peptide

<400> SEQUENCE: 62

Asp Ser Gly Arg Leu Glu Glu Glu Leu Arg Arg Arg Leu Ser Lys Gly
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: synthetic peptide

<400> SEQUENCE: 63

Asp Ser Gly Arg Leu Glu Glu Glu Leu Arg Arg Arg Leu Ser Pro Gly
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: synthetic peptide
```

```
<400> SEQUENCE: 64

Ser Asp Ser Gly Leu Glu Glu Glu Leu Arg Arg Arg Leu Ser Pro Gly
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: synthetic peptide

<400> SEQUENCE: 65

Ser Asp Ser Gly Val Glu Glu Glu Leu Arg Arg Arg Leu Ser Pro Gly
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: synthetic peptide

<400> SEQUENCE: 66

Ser Asp Ser Ala Val Glu Glu Glu Leu Arg Arg Arg Leu Ser Pro Gly
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: synthetic peptide

<400> SEQUENCE: 67

Ser Asp Ser Gly Leu Gln Glu Glu Leu Arg Arg Arg Leu Ser Pro Gly
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: synthetic peptide

<400> SEQUENCE: 68

Ser Asp Ser Gly Leu Glu Glu Gln Leu Arg Arg Arg Leu Ser Pro Gly
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: synthetic peptide

<400> SEQUENCE: 69

Ser Asp Ser Gly Leu Glu Glu Glu Ile Arg Arg Arg Leu Ser Pro Gly
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: synthetic peptide
```

```
<400> SEQUENCE: 70

Ser Asp Ser Gly Leu Glu Glu Glu Val Arg Arg Arg Leu Ser Pro Gly
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: synthetic peptide

<400> SEQUENCE: 71

Asp Ser Gly Glu Leu Glu Glu Glu Leu Arg Arg Arg Leu Ser Pro Gly
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: synthetic peptide

<400> SEQUENCE: 72

Asp Ser Gly Arg Leu Glu Gln Glu Leu Arg Arg Arg Leu Ser Pro Gly
1               5                   10                  15

<210> SEQ ID NO 73
<211> LENGTH: 18
<212> TYPE: PRT
<213> ORGANISM: Artificial Sequence
<220> FEATURE:
<223> OTHER INFORMATION: synthetic peptide

<400> SEQUENCE: 73

Gln Gln Asp Ser Gly Arg Leu Glu Glu Glu Ile Arg Arg Arg Leu Ser
1               5                   10                  15

Pro Gly

<210> SEQ ID NO 74
<211> LENGTH: 16
<212> TYPE: PRT
<213> ORGANISM: Artificial Sequence
<220> FEATURE:
<223> OTHER INFORMATION: synthetic peptide

<400> SEQUENCE: 74

Asp Ser Gly Arg Leu Glu Gln Glu Ile Arg Arg Arg Leu Ser Pro Gly
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: synthetic peptide

<400> SEQUENCE: 75

Asp Ser Gly Arg Leu Glu Gln Glu Ile Ala Arg Arg Leu Ser Pro Gly
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: synthetic peptide
```

<400> SEQUENCE: 76

Asp Ser Gly Arg Leu Glu Gln Glu Ile Gln Arg Arg Leu Ser Pro Gly
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: synthetic peptide

<400> SEQUENCE: 77

Asp Ser Gly Arg Leu Glu Gln Glu Ile Glu Arg Arg Leu Ser Pro Gly
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: synthetic peptide

<400> SEQUENCE: 78

Asp Ser Gly Arg Leu Glu Gln Glu Ile Arg Ala Arg Leu Ser Pro Gly
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: synthetic peptide

<400> SEQUENCE: 79

Asp Ser Gly Arg Leu Glu Gln Glu Ile Arg Gln Arg Leu Ser Pro Gly
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: synthetic peptide

<400> SEQUENCE: 80

Asp Ser Gly Arg Leu Glu Gln Glu Ile Arg Glu Arg Leu Ser Pro Gly
1               5                   10                  15

<210> SEQ ID NO 81
<211> LENGTH: 13
<212> TYPE: PRT
<213> ORGANISM: Artificial Sequence
<220> FEATURE:
<223> OTHER INFORMATION: synthetic peptide

<400> SEQUENCE: 81

Gly Pro Ser Arg Leu Glu Glu Glu Leu Arg Arg Arg Leu
1               5                   10

<210> SEQ ID NO 82
<211> LENGTH: 15
<212> TYPE: PRT
<213> ORGANISM: Artificial Sequence
<220> FEATURE:
<223> OTHER INFORMATION: synthetic peptide

```
<400> SEQUENCE: 82

Met Ser Gly Leu Glu Gln Glu Leu Arg Arg Arg Leu Thr Pro Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: synthetic peptide

<400> SEQUENCE: 83

Met Ser Gly Arg Leu Glu Glu Glu Leu Arg Arg Arg Leu Ser Pro Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: synthetic peptide

<400> SEQUENCE: 84

Ser Pro Ser Ala Val Glu Glu Glu Leu Arg Arg Arg Leu Ser Pro Ser
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: synthetic peptide

<400> SEQUENCE: 85

Gly Pro Ser Ala Val Glu Glu Glu Leu Arg Arg Arg Leu Ser
1               5                   10

<210> SEQ ID NO 86
<211> LENGTH: 16
<212> TYPE: PRT
<213> ORGANISM: Artificial Sequence
<220> FEATURE:
<223> OTHER INFORMATION: synthetic peptide

<400> SEQUENCE: 86

Met Pro Ser Gly Leu Glu Gln Glu Leu Arg Arg Arg Leu Thr Pro Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: synthetic peptide

<400> SEQUENCE: 87

Met Ser Ser Gly Leu Glu Gln Glu Leu Arg Arg Arg Leu Thr Pro Ser
1               5                   10                  15

<210> SEQ ID NO 88
<211> LENGTH: 17
<212> TYPE: PRT
<213> ORGANISM: Artificial Sequence
<220> FEATURE:
<223> OTHER INFORMATION: synthetic peptide

<400> SEQUENCE: 88
```

Met Pro Ser Gly Arg Leu Glu Glu Leu Arg Arg Leu Ser Pro
1               5                   10                  15

Ser

<210> SEQ ID NO 89
<211> LENGTH: 15
<212> TYPE: PRT
<213> ORGANISM: Artificial Sequence
<220> FEATURE:
<223> OTHER INFORMATION: synthetic peptide

<400> SEQUENCE: 89

Met Ser Gly Arg Leu Glu Glu Glu Leu Arg Arg Arg Leu Ser Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: synthetic peptide

<400> SEQUENCE: 90

Asp Ser Met Arg Leu Glu Glu Glu Leu Arg Arg Arg Leu Ser Lys Gly
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: synthetic peptide

<400> SEQUENCE: 91

Asp Ser Met Arg Leu Glu Glu Glu Leu Arg Arg Arg Leu Ser Pro Gly
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: synthetic peptide

<400> SEQUENCE: 92

Ser Asp Ser Gly Glu Glu Glu Leu Arg Arg Arg Leu Ser Pro Gly
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: synthetic peptide

<400> SEQUENCE: 93

Ser Asp Ser Gly Glu Glu Leu Arg Arg Arg Leu Ser Pro Gly
1               5                   10

<210> SEQ ID NO 94
<211> LENGTH: 15
<212> TYPE: PRT
<213> ORGANISM: Artificial Sequence
<220> FEATURE:
<223> OTHER INFORMATION: synthetic peptide

```
<400> SEQUENCE: 94

Asp Ser Gly Arg Leu Glu Glu Glu Leu Arg Arg Arg Ser Pro Gly
1               5                   10                  15

<210> SEQ ID NO 95
<211> LENGTH: 14
<212> TYPE: PRT
<213> ORGANISM: Artificial Sequence
<220> FEATURE:
<223> OTHER INFORMATION: synthetic peptide

<400> SEQUENCE: 95

Asp Ser Gly Arg Leu Glu Glu Glu Leu Arg Arg Ser Pro Gly
1               5                   10

<210> SEQ ID NO 96
<211> LENGTH: 13
<212> TYPE: PRT
<213> ORGANISM: Artificial Sequence
<220> FEATURE:
<223> OTHER INFORMATION: synthetic peptide

<400> SEQUENCE: 96

Asp Ser Gly Arg Leu Glu Glu Glu Leu Arg Ser Pro Gly
1               5                   10

<210> SEQ ID NO 97
<211> LENGTH: 16
<212> TYPE: PRT
<213> ORGANISM: Artificial Sequence
<220> FEATURE:
<223> OTHER INFORMATION: synthetic peptide

<400> SEQUENCE: 97

Ser Asp Ser Gly Leu Glu Glu Glu Ala Arg Arg Arg Leu Ser Pro Gly
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: synthetic peptide

<400> SEQUENCE: 98

Ser Asp Ser Gly Ala Glu Glu Glu Leu Arg Arg Arg Leu Ser Pro Gly
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: synthetic peptide

<400> SEQUENCE: 99

Asp Ser Gly Ala Leu Glu Glu Glu Leu Arg Arg Arg Leu Ser Pro Gly
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: synthetic peptide

<400> SEQUENCE: 100
```

Asp Ser Gly Ala Leu Glu Gln Glu Ile Arg Arg Leu Ser Pro Gly
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: synthetic peptide

<400> SEQUENCE: 101

Asp Ser Gly Arg Leu Glu Gln Glu Ile Arg Arg Ala Leu Ser Pro Gly
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: synthetic peptide

<400> SEQUENCE: 102

Asp Ser Gly Arg Leu Glu Gln Glu Ile Arg Arg Gln Leu Ser Pro Gly
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: synthetic peptide

<400> SEQUENCE: 103

Asp Ser Gly Arg Leu Glu Gln Glu Ile Arg Arg Glu Leu Ser Pro Gly
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: synthetic peptide

<400> SEQUENCE: 104

Pro Asp Ser Gly Leu Glu Gln Glu Leu Arg Arg Arg Leu Pro Thr Ala
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: synthetic peptide

<400> SEQUENCE: 105

Asp Pro Ser Gly Leu Glu Gln Glu Leu Arg Arg Arg Leu Pro Thr Ala
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: synthetic peptide

<400> SEQUENCE: 106

Asp Ser Pro Gly Leu Glu Gln Glu Leu Arg Arg Arg Leu Pro Thr Ala
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: synthetic peptide

<400> SEQUENCE: 107

Asp Ser Gly Pro Leu Glu Gln Glu Leu Arg Arg Arg Leu Pro Thr Ala
1               5                   10                  15

<210> SEQ ID NO 108
<211> LENGTH: 13
<212> TYPE: PRT
<213> ORGANISM: Artificial Sequence
<220> FEATURE:
<223> OTHER INFORMATION: synthetic peptide

<400> SEQUENCE: 108

Gly Pro Ser Gly Leu Glu Gln Glu Leu Arg Arg Arg Leu
1               5                   10

<210> SEQ ID NO 109
<211> LENGTH: 15
<212> TYPE: PRT
<213> ORGANISM: Artificial Sequence
<220> FEATURE:
<223> OTHER INFORMATION: synthetic peptide

<400> SEQUENCE: 109

Met Ser Ala Val Glu Glu Glu Leu Arg Arg Arg Leu Ser Pro Ser
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: synthetic peptide

<400> SEQUENCE: 110

Met Ser Gly Leu Glu Gln Glu Leu Arg Arg Arg Leu Thr Pro Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: synthetic peptide

<400> SEQUENCE: 111

Met Ser Ala Val Glu Glu Glu Leu Arg Arg Arg Leu Ser Pro Ser
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: synthetic peptide

<400> SEQUENCE: 112

Met Pro Ser Ala Val Glu Glu Glu Leu Arg Arg Arg Leu Ser Pro Ser

<210> SEQ ID NO 113
<211> LENGTH: 16
<212> TYPE: PRT
<213> ORGANISM: Artificial Sequence
<220> FEATURE:
<223> OTHER INFORMATION: synthetic peptide

<400> SEQUENCE: 113

Met Ser Ser Ala Val Glu Glu Glu Leu Arg Arg Arg Leu Ser Pro Ser
1               5                   10                  15

<210> SEQ ID NO 114
<211> LENGTH: 14
<212> TYPE: PRT
<213> ORGANISM: Artificial Sequence
<220> FEATURE:
<223> OTHER INFORMATION: synthetic peptide

<400> SEQUENCE: 114

Pro Ser Gly Arg Leu Glu Glu Glu Leu Arg Arg Arg Leu Pro
1               5                   10

<210> SEQ ID NO 115
<211> LENGTH: 13
<212> TYPE: PRT
<213> ORGANISM: Artificial Sequence
<220> FEATURE:
<223> OTHER INFORMATION: antibody CDR

<400> SEQUENCE: 115

Gly Val Thr Ile Ser Ala Leu Asn Ala Met Ala Met Gly
1               5                   10

<210> SEQ ID NO 116
<211> LENGTH: 9
<212> TYPE: PRT
<213> ORGANISM: Artificial Sequence
<220> FEATURE:
<223> OTHER INFORMATION: antibody CDR

<400> SEQUENCE: 116

Ala Val Ser Glu Arg Gly Asn Ala Met
1               5

<210> SEQ ID NO 117
<211> LENGTH: 11
<212> TYPE: PRT
<213> ORGANISM: Artificial Sequence
<220> FEATURE:
<223> OTHER INFORMATION: antibody CDR

<400> SEQUENCE: 117

Leu Glu Asp Arg Val Asp Ser Phe His Asp Tyr
1               5                   10

<210> SEQ ID NO 118
<211> LENGTH: 13
<212> TYPE: PRT
<213> ORGANISM: Artificial Sequence
<220> FEATURE:
<223> OTHER INFORMATION: antibody CDR

<400> SEQUENCE: 118

Gly Val Thr Ile Ser Ala Leu Asn Ala Met Ala Met Gly
1               5                   10

<210> SEQ ID NO 119
<211> LENGTH: 9
<212> TYPE: PRT
<213> ORGANISM: Artificial Sequence
<220> FEATURE:
<223> OTHER INFORMATION: antibody CDR

<400> SEQUENCE: 119

Ala Val Ser Ser Arg Gly Asn Ala Met
1               5

<210> SEQ ID NO 120
<211> LENGTH: 11
<212> TYPE: PRT
<213> ORGANISM: Artificial Sequence
<220> FEATURE:
<223> OTHER INFORMATION: antibody CDR

<400> SEQUENCE: 120

Leu Glu Asp Arg Val Asp Ser Phe His Asp Tyr
1               5                   10

<210> SEQ ID NO 121
<211> LENGTH: 13
<212> TYPE: PRT
<213> ORGANISM: Artificial Sequence
<220> FEATURE:
<223> OTHER INFORMATION: antibody CDR

<400> SEQUENCE: 121

Gly Val Thr Val Ser Ala Leu Asn Ala Met Ala Met Gly
1               5                   10

<210> SEQ ID NO 122
<211> LENGTH: 9
<212> TYPE: PRT
<213> ORGANISM: Artificial Sequence
<220> FEATURE:
<223> OTHER INFORMATION: antibody CDR

<400> SEQUENCE: 122

Ala Val Ser Glu Arg Gly Asn Ala Met
1               5

<210> SEQ ID NO 123
<211> LENGTH: 11
<212> TYPE: PRT
<213> ORGANISM: Artificial Sequence
<220> FEATURE:
<223> OTHER INFORMATION: antibody CDR

<400> SEQUENCE: 123

Leu Glu Asp Arg Val Asp Ser Phe His Asp Tyr
1               5                   10

<210> SEQ ID NO 124
<211> LENGTH: 25
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (5)..(5)
<223> OTHER INFORMATION: Xaa is Q, V, E, or L
<220> FEATURE:
<221> NAME/KEY: MISC_FEATURE

```
<222> LOCATION: (13)..(13)
<223> OTHER INFORMATION: Xaa is Q or P
<220> FEATURE:
<221> NAME/KEY: MISC_FEATURE
<222> LOCATION: (18)..(18)
<223> OTHER INFORMATION: Xaa is L or M

<400> SEQUENCE: 124

Glu Val Gln Leu Xaa Glu Ser Gly Gly Gly Leu Val Xaa Pro Gly Gly
1               5                   10                  15

Ser Xaa Arg Leu Ser Cys Thr Ala Ser
            20                  25

<210> SEQ ID NO 125
<211> LENGTH: 25
<212> TYPE: PRT
<213> ORGANISM: Artificial Sequence
<220> FEATURE:
<223> OTHER INFORMATION: antibody FR

<400> SEQUENCE: 125

Glu Val Gln Leu Gln Glu Ser Gly Gly Gly Leu Val Gln Pro Gly Gly
1               5                   10                  15

Ser Leu Arg Leu Ser Cys Thr Ala Ser
            20                  25

<210> SEQ ID NO 126
<211> LENGTH: 14
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (5)..(5)
<223> OTHER INFORMATION: Xaa is A or R
<220> FEATURE:
<221> NAME/KEY: MISC_FEATURE
<222> LOCATION: (9)..(9)
<223> OTHER INFORMATION: Xaa is R or E

<400> SEQUENCE: 126

Trp Tyr Arg Gln Xaa Pro Gly Glu Xaa Arg Val Met Val Ala
1               5                   10

<210> SEQ ID NO 127
<211> LENGTH: 14
<212> TYPE: PRT
<213> ORGANISM: Artificial Sequence
<220> FEATURE:
<223> OTHER INFORMATION: antibody FR

<400> SEQUENCE: 127

Trp Tyr Arg Gln Ala Pro Gly Glu Arg Arg Val Met Val Ala
1               5                   10

<210> SEQ ID NO 128
<211> LENGTH: 14
<212> TYPE: PRT
<213> ORGANISM: Artificial Sequence
<220> FEATURE:
<223> OTHER INFORMATION: antibody FR

<400> SEQUENCE: 128

Trp Tyr Arg Gln Ala Pro Gly Glu Glu Arg Val Met Val Ala
1               5                   10
```

```
<210> SEQ ID NO 129
<211> LENGTH: 39
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (28)..(28)
<223> OTHER INFORMATION: Xaa is K or Q
<220> FEATURE:
<221> NAME/KEY: MISC_FEATURE
<222> LOCATION: (32)..(32)
<223> OTHER INFORMATION: Xaa is T or M

<400> SEQUENCE: 129

Tyr Arg Glu Ser Val Gln Gly Arg Phe Thr Val Thr Arg Asp Phe Thr
1               5                   10                  15

Asn Lys Met Val Ser Leu Gln Met Asp Asn Leu Xaa Pro Glu Asp Xaa
            20                  25                  30

Ala Val Tyr Tyr Cys His Val
            35

<210> SEQ ID NO 130
<211> LENGTH: 39
<212> TYPE: PRT
<213> ORGANISM: Artificial Sequence
<220> FEATURE:
<223> OTHER INFORMATION: antibody FR

<400> SEQUENCE: 130

Tyr Arg Glu Ser Val Gln Gly Arg Phe Thr Val Thr Arg Asp Phe Thr
1               5                   10                  15

Asn Lys Met Val Ser Leu Gln Met Asp Asn Leu Lys Pro Glu Asp Thr
            20                  25                  30

Ala Val Tyr Tyr Cys His Val
            35

<210> SEQ ID NO 131
<211> LENGTH: 11
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (5)..(5)
<223> OTHER INFORMATION: Xaa is T or I

<400> SEQUENCE: 131

Trp Gly Gln Gly Xaa Gln Val Thr Val Ser Ser
1               5                   10

<210> SEQ ID NO 132
<211> LENGTH: 11
<212> TYPE: PRT
<213> ORGANISM: Artificial Sequence
<220> FEATURE:
<223> OTHER INFORMATION: antibody FR

<400> SEQUENCE: 132

Trp Gly Gln Gly Thr Gln Val Thr Val Ser Ser
1               5                   10

<210> SEQ ID NO 133
<211> LENGTH: 122
<212> TYPE: PRT
```

<213> ORGANISM: Artificial Sequence
<220> FEATURE:
<223> OTHER INFORMATION: Camelid VHH domain

<400> SEQUENCE: 133

| Glu | Val | Gln | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Val | Thr | Ile | Ser | Ala | Leu |
|---|---|---|---|---|---|---|---|---|---|---|---|---|---|---|---|
| | | | 20 | | | | | 25 | | | | | 30 | | |

| Asn | Ala | Met | Ala | Met | Gly | Trp | Tyr | Arg | Gln | Ala | Pro | Gly | Glu | Arg | Arg |
|---|---|---|---|---|---|---|---|---|---|---|---|---|---|---|---|
| | | 35 | | | | | 40 | | | | | 45 | | | |

| Val | Met | Val | Ala | Ala | Val | Ser | Glu | Arg | Gly | Asn | Ala | Met | Tyr | Arg | Glu |
|---|---|---|---|---|---|---|---|---|---|---|---|---|---|---|---|
| | 50 | | | | | 55 | | | | | 60 | | | | |

| Ser | Val | Gln | Gly | Arg | Phe | Thr | Val | Thr | Arg | Asp | Phe | Thr | Asn | Lys | Met |
|---|---|---|---|---|---|---|---|---|---|---|---|---|---|---|---|
| 65 | | | | | 70 | | | | | 75 | | | | | 80 |

| Val | Ser | Leu | Gln | Met | Asp | Asn | Leu | Lys | Pro | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | His | Val | Leu | Glu | Asp | Arg | Val | Asp | Ser | Phe | His | Asp | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Gln | Val | Thr | Val | Ser | Ser |
|---|---|---|---|---|---|---|---|---|---|
| | | | 115 | | | | | 120 | |

<210> SEQ ID NO 134
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 134

| Glu | Val | Gln | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Val | Thr | Ile | Ser | Ala | Leu |
|---|---|---|---|---|---|---|---|---|---|---|---|---|---|---|---|
| | | | 20 | | | | | 25 | | | | | 30 | | |

| Asn | Ala | Met | Ala | Met | Gly | Trp | Tyr | Arg | Gln | Ala | Pro | Gly | Glu | Glu | Arg |
|---|---|---|---|---|---|---|---|---|---|---|---|---|---|---|---|
| | | 35 | | | | | 40 | | | | | 45 | | | |

| Val | Met | Val | Ala | Ala | Val | Ser | Ser | Arg | Gly | Asn | Ala | Met | Tyr | Arg | Glu |
|---|---|---|---|---|---|---|---|---|---|---|---|---|---|---|---|
| | 50 | | | | | 55 | | | | | 60 | | | | |

| Ser | Val | Gln | Gly | Arg | Phe | Thr | Val | Thr | Arg | Asp | Phe | Thr | Asn | Lys | Met |
|---|---|---|---|---|---|---|---|---|---|---|---|---|---|---|---|
| 65 | | | | | 70 | | | | | 75 | | | | | 80 |

| Val | Ser | Leu | Gln | Met | Asp | Asn | Leu | Lys | Pro | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | His | Val | Leu | Glu | Asp | Arg | Val | Asp | Ser | Phe | His | Asp | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Gln | Val | Thr | Val | Ser | Ser |
|---|---|---|---|---|---|---|---|---|---|
| | | | 115 | | | | | 120 | |

<210> SEQ ID NO 135
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 135

| Glu | Val | Gln | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Val | Thr | Ile | Ser | Ala | Leu |
|---|---|---|---|---|---|---|---|---|---|---|---|---|---|---|---|
| | | | 20 | | | | | 25 | | | | | 30 | | |

```
Asn Ala Met Ala Met Gly Trp Tyr Arg Gln Ala Pro Gly Glu Arg
            35                  40                  45

Val Met Val Ala Ala Val Ser Glu Arg Gly Asn Ala Met Tyr Arg Glu
        50                  55                  60

Ser Val Gln Gly Arg Phe Thr Val Thr Arg Asp Phe Thr Asn Lys Met
 65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
                100                 105                 110

Gly Gln Gly Thr Gln Val Thr Val Ser Ser
            115                 120

<210> SEQ ID NO 136
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 136

Glu Val Gln Leu Gln Glu Ser Gly Gly Gly Leu Val Gln Pro Gly Gly
 1               5                  10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
            35                  40                  45

Val Met Val Ala Ala Val Ser Ser Arg Gly Asn Ala Met Tyr Arg Glu
        50                  55                  60

Ser Val Gln Gly Arg Phe Thr Val Thr Arg Asp Phe Thr Asn Lys Met
 65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
                100                 105                 110

Gly Gln Gly Thr Gln Val Thr Val Ser Ser
            115                 120

<210> SEQ ID NO 137
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 137

Glu Val Gln Leu Val Glu Ser Gly Gly Gly Leu Val Pro Pro Gly Gly
 1               5                  10                  15

Ser Met Arg Leu Ser Cys Thr Ala Ser Gly Val Thr Val Ser Ala Leu
            20                  25                  30

Asn Ala Met Ala Met Gly Trp Tyr Arg Gln Arg Pro Gly Glu Arg Arg
            35                  40                  45

Val Met Val Ala Ala Val Ser Glu Arg Gly Asn Ala Met Tyr Arg Glu
        50                  55                  60

Ser Val Gln Gly Arg Phe Thr Val Thr Arg Asp Phe Thr Asn Lys Met
 65                  70                  75                  80

Val Ser Leu Gln Met Asp Asn Leu Gln Pro Glu Asp Met Ala Val Tyr
```

```
                     85                  90                  95

Tyr Cys His Val Leu Glu Asp Arg Val Asp Ser Phe His Asp Tyr Trp
            100                 105                 110

Gly Gln Gly Ile Gln Val Thr Val Ser Ser
        115                 120

<210> SEQ ID NO 138
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 138

Glu Val Gln Leu Val Glu Ser Gly Gly Gly Leu Val Pro Pro Gly Gly
1               5                   10                  15

Ser Met Arg Leu Ser Cys Thr Ala Pro Gly Val Thr Val Ser Ala Leu
            20                  25                  30

Asn Ala Met Ala Met Gly Trp Tyr Arg Gln Arg Pro Gly Glu Arg Arg
        35                  40                  45

Val Met Val Ala Ala Val Ser Glu Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Gln Pro Glu Asp Met Ala Val Tyr
                85                  90                  95

Tyr Cys His Val Leu Glu Asp Arg Val Asp Ser Phe His Asp Tyr Trp
            100                 105                 110

Gly Gln Gly Ile Gln Val Thr Val Ser Ser
        115                 120

<210> SEQ ID NO 139
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 139

Glu Val Gln Leu Val Glu Ser Gly Gly Gly Val Val Gln Pro Gly Gly
1               5                   10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
        35                  40                  45

Val Met Val Ala Ala Val Ser Glu Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 140
<211> LENGTH: 122
```

```
<212> TYPE: PRT
<213> ORGANISM: Artificial Sequence
<220> FEATURE:
<223> OTHER INFORMATION: Camelid VHH domain

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
        35                  40                  45

Val Met Val Ala Ala Val Ser Glu Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 141
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 141

Glu Val Gln Leu Glu Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
        35                  40                  45

Val Met Val Ala Ala Val Ser Glu Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 142
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
```

```
                    20                  25                  30
Asn Ala Met Ala Met Gly Trp Tyr Arg Gln Ala Pro Gly Glu Arg Arg
            35                  40                  45

Val Met Val Ala Ala Val Ser Glu Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 143
<211> LENGTH: 10
<212> TYPE: PRT
<213> ORGANISM: Artificial Sequence
<220> FEATURE:
<223> OTHER INFORMATION: antibody CDR

<400> SEQUENCE: 143

Gly Thr Met Ser Ala Ile Asn Ala Leu Asn
1               5                   10

<210> SEQ ID NO 144
<211> LENGTH: 9
<212> TYPE: PRT
<213> ORGANISM: Artificial Sequence
<220> FEATURE:
<223> OTHER INFORMATION: antibody CDR

<400> SEQUENCE: 144

Ala Ile Thr Asp Asn Gly Asn Ala His
1               5

<210> SEQ ID NO 145
<211> LENGTH: 12
<212> TYPE: PRT
<213> ORGANISM: Artificial Sequence
<220> FEATURE:
<223> OTHER INFORMATION: antibody CDR

<400> SEQUENCE: 145

Leu Glu Glu Glu Lys Leu Gly Val Trp Val Asp Tyr
1               5                   10

<210> SEQ ID NO 146
<211> LENGTH: 10
<212> TYPE: PRT
<213> ORGANISM: Artificial Sequence
<220> FEATURE:
<223> OTHER INFORMATION: antibody CDR

<400> SEQUENCE: 146

Gly Thr Met Ser Ala Ile Asn Ala Leu Asn
1               5                   10

<210> SEQ ID NO 147
<211> LENGTH: 9
<212> TYPE: PRT
<213> ORGANISM: Artificial Sequence
<220> FEATURE:
<223> OTHER INFORMATION: antibody CDR
```

```
<400> SEQUENCE: 147

Ala Ile Thr Asp Asn Gly Asn Ala His
1               5

<210> SEQ ID NO 148
<211> LENGTH: 11
<212> TYPE: PRT
<213> ORGANISM: Artificial Sequence
<220> FEATURE:
<223> OTHER INFORMATION: antibody CDR

<400> SEQUENCE: 148

Leu Glu Glu Lys Leu Gly Ala Trp Val Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: antibody CDR

<400> SEQUENCE: 149

Gly Thr Met Ser Ala Ile Asn Ala Leu Asn
1               5                   10

<210> SEQ ID NO 150
<211> LENGTH: 9
<212> TYPE: PRT
<213> ORGANISM: Artificial Sequence
<220> FEATURE:
<223> OTHER INFORMATION: antibody CDR

<400> SEQUENCE: 150

Ala Ile Thr Asp Asn Gly Asn Ala His
1               5

<210> SEQ ID NO 151
<211> LENGTH: 12
<212> TYPE: PRT
<213> ORGANISM: Artificial Sequence
<220> FEATURE:
<223> OTHER INFORMATION: antibody CDR

<400> SEQUENCE: 151

Leu Glu Lys Glu Lys Leu Gly Val Trp Val Asp Tyr
1               5                   10

<210> SEQ ID NO 152
<211> LENGTH: 25
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (5)..(5)
<223> OTHER INFORMATION: Xaa is V or L

<400> SEQUENCE: 152

Glu Val Gln Leu Xaa Glu Ser Gly Gly Gly Leu Val Gln Pro Gly Gly
1               5                   10                  15

Ser Leu Thr Leu Ser Cys Ala Ala Ser
            20                  25
```

```
<210> SEQ ID NO 153
<211> LENGTH: 14
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (5)..(5)
<223> OTHER INFORMATION: Xaa is P or A

<400> SEQUENCE: 153

Trp Tyr Arg Gln Xaa Pro Gly Lys Glu Arg Lys Met Val Ala
1               5                   10

<210> SEQ ID NO 154
<211> LENGTH: 39
<212> TYPE: PRT
<213> ORGANISM: Artificial Sequence
<220> FEATURE:
<223> OTHER INFORMATION: antibody FR
<220> FEATURE:
<221> NAME/KEY: MISC_FEATURE
<222> LOCATION: (28)..(28)
<223> OTHER INFORMATION: Xaa is K or E

<400> SEQUENCE: 154

Tyr Ala Asp Ser Val Lys Gly Arg Phe Thr Ile Ser Arg Asp Asn Ala
1               5                   10                  15

Arg Asn Met Val Phe Leu Gln Met Asn Ser Leu Xaa Pro Asp Asp Thr
            20                  25                  30

Ala Val Tyr Tyr Cys His Tyr
        35

<210> SEQ ID NO 155
<211> LENGTH: 11
<212> TYPE: PRT
<213> ORGANISM: Artificial Sequence
<220> FEATURE:
<223> OTHER INFORMATION: antibody FR

<400> SEQUENCE: 155

Trp Gly Gln Gly Thr Gln Val Thr Val Ser Ser
1               5                   10

<210> SEQ ID NO 156
<211> LENGTH: 120
<212> TYPE: PRT
<213> ORGANISM: Artificial Sequence
<220> FEATURE:
<223> OTHER INFORMATION: Camelid VHH domain

<400> SEQUENCE: 156

Glu Val Gln Leu Val Glu Ser Gly Gly Gly Leu Val Gln Pro Gly Gly
1               5                   10                  15

Ser Leu Thr Leu Ser Cys Ala Ala Ser Gly Thr Met Ser Ala Ile Asn
            20                  25                  30

Ala Leu Asn Trp Tyr Arg Gln Pro Pro Gly Lys Glu Arg Lys Met Val
        35                  40                  45

Ala Ala Ile Thr Asp Asn Gly Asn Ala His Tyr Ala Asp Ser Val Lys
    50                  55                  60

Gly Arg Phe Thr Ile Ser Arg Asp Asn Ala Arg Asn Met Val Phe Leu
65                  70                  75                  80

Gln Met Asn Ser Leu Lys Pro Asp Asp Thr Ala Val Tyr Tyr Cys His
                85                  90                  95
```

Tyr Leu Glu Glu Glu Lys Leu Gly Val Trp Val Asp Tyr Trp Gly Gln
                100                 105                 110

Gly Thr Gln Val Thr Val Ser Ser
        115                 120

<210> SEQ ID NO 157
<211> LENGTH: 119
<212> TYPE: PRT
<213> ORGANISM: Artificial Sequence
<220> FEATURE:
<223> OTHER INFORMATION: Camelid VHH domain

<400> SEQUENCE: 157

Glu Val Gln Leu Leu Glu Ser Gly Gly Gly Leu Val Gln Pro Gly Gly
1               5                   10                  15

Ser Leu Thr Leu Ser Cys Ala Ala Ser Gly Thr Met Ser Ala Ile Asn
            20                  25                  30

Ala Leu Asn Trp Tyr Arg Gln Ala Pro Gly Lys Glu Arg Lys Met Val
        35                  40                  45

Ala Ala Ile Thr Asp Asn Gly Asn Ala His Tyr Ala Asp Ser Val Lys
    50                  55                  60

Gly Arg Phe Thr Ile Ser Arg Asp Asn Ala Arg Asn Met Val Phe Leu
65                  70                  75                  80

Gln Met Asn Ser Leu Glu Pro Asp Asp Thr Ala Val Tyr Tyr Cys His
                85                  90                  95

Tyr Leu Glu Glu Lys Leu Gly Ala Trp Val Asp Tyr Trp Gly Gln Gly
                100                 105                 110

Thr Gln Val Thr Val Ser Ser
        115

<210> SEQ ID NO 158
<211> LENGTH: 120
<212> TYPE: PRT
<213> ORGANISM: Artificial Sequence
<220> FEATURE:
<223> OTHER INFORMATION: Camelid VHH domain

<400> SEQUENCE: 158

Glu Val Gln Leu Val Glu Ser Gly Gly Gly Leu Val Gln Pro Gly Gly
1               5                   10                  15

Ser Leu Thr Leu Ser Cys Ala Ala Ser Gly Thr Met Ser Ala Ile Asn
            20                  25                  30

Ala Leu Asn Trp Tyr Arg Gln Pro Pro Gly Lys Glu Arg Lys Met Val
        35                  40                  45

Ala Ala Ile Thr Asp Asn Gly Asn Ala His Tyr Ala Asp Ser Val Lys
    50                  55                  60

Gly Arg Phe Thr Ile Ser Arg Asp Asn Ala Arg Asn Met Val Phe Leu
65                  70                  75                  80

Gln Met Asn Ser Leu Lys Pro Asp Asp Thr Ala Val Tyr Tyr Cys His
                85                  90                  95

Tyr Leu Glu Lys Glu Lys Leu Gly Val Trp Val Asp Tyr Trp Gly Gln
                100                 105                 110

Gly Thr Gln Val Thr Val Ser Ser
        115                 120

<210> SEQ ID NO 159
<211> LENGTH: 15
<212> TYPE: PRT

```
<213> ORGANISM: Artificial Sequence
<220> FEATURE:
<223> OTHER INFORMATION: linker

<400> SEQUENCE: 159

Gly Gly Gly Gly Ser Gly Gly Gly Gly Ser Gly Gly Gly Gly Ser
1               5                   10                  15

<210> SEQ ID NO 160
<211> LENGTH: 8
<212> TYPE: PRT
<213> ORGANISM: Artificial Sequence
<220> FEATURE:
<223> OTHER INFORMATION: FLAG-tag

<400> SEQUENCE: 160

Asp Tyr Lys Asp Asp Asp Asp Lys
1               5

<210> SEQ ID NO 161
<211> LENGTH: 10
<212> TYPE: PRT
<213> ORGANISM: Artificial Sequence
<220> FEATURE:
<223> OTHER INFORMATION: Myc-tag

<400> SEQUENCE: 161

Glu Gln Lys Leu Ile Ser Glu Glu Asp Leu
1               5                   10

<210> SEQ ID NO 162
<211> LENGTH: 9
<212> TYPE: PRT
<213> ORGANISM: Artificial Sequence
<220> FEATURE:
<223> OTHER INFORMATION: HA-tag

<400> SEQUENCE: 162

Tyr Pro Tyr Asp Val Pro Asp Tyr Ala
1               5

<210> SEQ ID NO 163
<211> LENGTH: 11
<212> TYPE: PRT
<213> ORGANISM: Artificial Sequence
<220> FEATURE:
<223> OTHER INFORMATION: VSV-G-tag

<400> SEQUENCE: 163

Tyr Thr Asp Ile Glu Met Asn Arg Leu Gly Lys
1               5                   10

<210> SEQ ID NO 164
<211> LENGTH: 11
<212> TYPE: PRT
<213> ORGANISM: Artificial Sequence
<220> FEATURE:
<223> OTHER INFORMATION: HSV-tag

<400> SEQUENCE: 164

Gln Pro Glu Leu Ala Pro Glu Asp Pro Glu Asp
1               5                   10

<210> SEQ ID NO 165
<211> LENGTH: 14
<212> TYPE: PRT
<213> ORGANISM: Artificial Sequence
```

```
<220> FEATURE:
<223> OTHER INFORMATION: V5-tag

<400> SEQUENCE: 165

Gly Lys Pro Ile Pro Asn Pro Leu Leu Gly Leu Asp Ser Thr
1               5                   10

<210> SEQ ID NO 166
<211> LENGTH: 12
<212> TYPE: PRT
<213> ORGANISM: Artificial Sequence
<220> FEATURE:
<223> OTHER INFORMATION: SPOT-tag

<400> SEQUENCE: 166

Pro Asp Arg Val Arg Ala Val Ser His Trp Ser Ser
1               5                   10

<210> SEQ ID NO 167
<211> LENGTH: 12
<212> TYPE: PRT
<213> ORGANISM: Artificial Sequence
<220> FEATURE:
<223> OTHER INFORMATION: BC2 tag

<400> SEQUENCE: 167

Pro Asp Arg Lys Ala Ala Val Ser His Trp Gln Gln
1               5                   10

<210> SEQ ID NO 168
<211> LENGTH: 4
<212> TYPE: PRT
<213> ORGANISM: Artificial Sequence
<220> FEATURE:
<223> OTHER INFORMATION: EPEA tag

<400> SEQUENCE: 168

Glu Pro Glu Ala
1

<210> SEQ ID NO 169
<211> LENGTH: 15
<212> TYPE: PRT
<213> ORGANISM: Artificial Sequence
<220> FEATURE:
<223> OTHER INFORMATION: synthetic peptide

<400> SEQUENCE: 169

Gly Pro Ser Gly Leu Glu Gln Glu Leu Arg Arg Arg Leu Thr Ala
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: synthetic peptide

<400> SEQUENCE: 170

Ser Pro Ser Gly Leu Glu Gln Glu Leu Arg Arg Arg Leu Thr Asp Pro
1               5                   10                  15

<210> SEQ ID NO 171
<211> LENGTH: 17
<212> TYPE: PRT
<213> ORGANISM: Artificial Sequence
<220> FEATURE:
```

<223> OTHER INFORMATION: synthetic peptide

<400> SEQUENCE: 171

Ser Pro Ser Gly Leu Glu Gln Glu Leu Arg Arg Arg Leu Thr Ala Asp
1               5                   10                  15

Pro

<210> SEQ ID NO 172
<211> LENGTH: 17
<212> TYPE: PRT
<213> ORGANISM: Artificial Sequence
<220> FEATURE:
<223> OTHER INFORMATION: synthetic peptide

<400> SEQUENCE: 172

Ser Pro Ser Gly Leu Glu Gln Glu Leu Arg Arg Arg Leu Thr Ala Glu
1               5                   10                  15

Pro

<210> SEQ ID NO 173
<211> LENGTH: 16
<212> TYPE: PRT
<213> ORGANISM: Artificial Sequence
<220> FEATURE:
<223> OTHER INFORMATION: synthetic peptide

<400> SEQUENCE: 173

Asp Ser Pro Gly Leu Glu Gln Glu Leu Arg Arg Arg Leu Thr Ala Pro
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: synthetic peptide

<400> SEQUENCE: 174

Ser Pro Ser Gly Leu Glu Gln Glu Leu Arg Arg Arg Leu Ser Pro Ser
1               5                   10                  15

<210> SEQ ID NO 175
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 175

Glu Val Gln Leu Gln Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
                20                  25                  30

Asn Ala Met Ala Met Gly Trp Tyr Arg Gln Ala Pro Gly Glu Arg Arg
            35                  40                  45

Val Met Val Ala Ala Val Ser Asp Arg Gly Asn Ala Met Tyr Arg Glu
        50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp

```
              100                 105                 110

Gly Gln Gly Thr Gln Val Thr Val Ser Ser
        115                 120

<210> SEQ ID NO 176
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 176

Glu Val Gln Leu Gln Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
        35                  40                  45

Val Met Val Ala Ala Val Ser Asn Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 177
<211> LENGTH: 122
<212> TYPE: PRT
<213> ORGANISM: Artificial Sequence
<220> FEATURE:
<223> OTHER INFORMATION: Camelid VHH domain

<400> SEQUENCE: 177

Glu Val Gln Leu Gln Glu Ser Gly Gly Gly Leu Val Gln Pro Gly Gly
1               5                   10                  15

Ser Leu Arg Leu Ser Cys Thr Ala Ser Gly Val Thr Ile Ser Ala Leu
            20                  25                  30

Asn Ala Met Ala Met Gly Trp Tyr Arg Gln Ala Pro Gly Glu Arg Arg
        35                  40                  45

Val Met Val Ala Ala Val Ser His Arg Gly Asn Ala Met Tyr Arg Glu
    50                  55                  60

Ser Val Gln Gly Arg Phe Thr Val Thr Arg Asp Phe Thr Asn Lys Met
65                  70                  75                  80

Val Ser Leu Gln Met Asp Asn Leu Lys Pro Glu Asp Thr Ala Val Tyr
                85                  90                  95

Tyr Cys His Val Leu Glu Asp Arg Val Asp Ser Phe His Asp Tyr Trp
            100                 105                 110

Gly Gln Gly Thr Gln Val Thr Val Ser Ser
        115                 120

<210> SEQ ID NO 178
<211> LENGTH: 8
<212> TYPE: PRT
<213> ORGANISM: Artificial Sequence
<220> FEATURE:
```

```
<223> OTHER INFORMATION: Strep-tag

<400> SEQUENCE: 178

Trp Ser His Pro Gln Phe Glu Lys
1               5

<210> SEQ ID NO 179
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 179

Pro Ser Arg Leu Glu Glu Glu Leu Arg Arg Arg Leu Thr Glu Pro
1               5                   10                  15

<210> SEQ ID NO 180
<211> LENGTH: 490
<212> TYPE: PRT
<213> ORGANISM: Artificial Sequence
<220> FEATURE:
<223> OTHER INFORMATION: fusion protein

<400> SEQUENCE: 180

Met Pro Ser Arg Leu Glu Glu Glu Leu Arg Arg Arg Leu Thr Glu Pro
1               5                   10                  15

Asp Tyr Lys Asp Asp Asp Asp Lys Gly Ser Thr Arg Ser Val Ser Ser
                20                  25                  30

Ser Ser Tyr Arg Arg Met Phe Gly Gly Ser Gly Thr Ser Ser Arg Pro
            35                  40                  45

Ser Ser Asn Arg Ser Tyr Val Thr Thr Ser Thr Arg Thr Tyr Ser Leu
    50                  55                  60

Gly Ser Ala Leu Arg Pro Ser Thr Ser Arg Ser Leu Tyr Ser Ser Ser
65                  70                  75                  80

Pro Gly Gly Ala Tyr Val Thr Arg Ser Ser Ala Val Arg Leu Arg Ser
                85                  90                  95

Ser Val Pro Gly Val Arg Leu Leu Gln Asp Ser Val Asp Phe Ser Leu
            100                 105                 110

Ala Asp Ala Ile Asn Thr Glu Phe Lys Asn Thr Arg Thr Asn Glu Lys
        115                 120                 125

Val Glu Leu Gln Glu Leu Asn Asp Arg Phe Ala Asn Tyr Ile Asp Lys
    130                 135                 140

Val Arg Phe Leu Glu Gln Gln Asn Lys Ile Leu Leu Ala Glu Leu Glu
145                 150                 155                 160

Gln Leu Lys Gly Gln Gly Lys Ser Arg Leu Gly Asp Leu Tyr Glu Glu
                165                 170                 175

Glu Met Arg Glu Leu Arg Arg Gln Val Asp Gln Leu Thr Asn Asp Lys
            180                 185                 190

Ala Arg Val Glu Val Glu Arg Asp Asn Leu Ala Glu Asp Ile Met Arg
        195                 200                 205

Leu Arg Glu Lys Leu Gln Glu Glu Met Leu Gln Arg Glu Glu Ala Glu
    210                 215                 220
```

Ser Thr Leu Gln Ser Phe Arg Gln Asp Val Asp Asn Ala Ser Leu Ala
225                 230                 235                 240

Arg Leu Asp Leu Glu Arg Lys Val Glu Ser Leu Gln Glu Glu Ile Ala
            245                 250                 255

Phe Leu Lys Lys Leu His Asp Glu Glu Ile Gln Glu Leu Gln Ala Gln
                260                 265                 270

Ile Gln Glu Gln His Val Gln Ile Asp Val Asp Val Ser Lys Pro Asp
        275                 280                 285

Leu Thr Ala Ala Leu Arg Asp Val Arg Gln Gln Tyr Glu Ser Val Ala
    290                 295                 300

Ala Lys Asn Leu Gln Glu Ala Glu Glu Trp Tyr Lys Ser Lys Phe Ala
305                 310                 315                 320

Asp Leu Ser Glu Ala Ala Asn Arg Asn Asn Asp Ala Leu Arg Gln Ala
                325                 330                 335

Lys Gln Glu Ser Asn Glu Tyr Arg Arg Gln Val Gln Ser Leu Thr Cys
                340                 345                 350

Glu Val Asp Ala Leu Lys Gly Thr Asn Glu Ser Leu Glu Arg Gln Met
            355                 360                 365

Arg Glu Met Glu Glu Asn Phe Ala Leu Glu Ala Ala Asn Tyr Gln Asp
370                 375                 380

Thr Ile Gly Arg Leu Gln Asp Glu Ile Gln Asn Met Lys Glu Glu Met
385                 390                 395                 400

Ala Arg His Leu Arg Glu Tyr Gln Asp Leu Leu Asn Val Lys Met Ala
                405                 410                 415

Leu Asp Ile Glu Ile Ala Thr Tyr Arg Lys Leu Leu Glu Gly Glu Glu
            420                 425                 430

Ser Arg Ile Ser Leu Pro Leu Pro Thr Phe Ser Ser Leu Asn Leu Arg
            435                 440                 445

Glu Thr Asn Leu Glu Ser Leu Pro Leu Val Asp Thr His Ser Lys Arg
450                 455                 460

Thr Leu Leu Ile Lys Thr Val Glu Thr Arg Asp Gly Gln Val Ile Asn
465                 470                 475                 480

Glu Thr Ser Gln His His Asp Asp Leu Glu
                485                 490

<210> SEQ ID NO 181
<211> LENGTH: 489
<212> TYPE: PRT
<213> ORGANISM: Artificial Sequence
<220> FEATURE:
<223> OTHER INFORMATION: fusion protein

<400> SEQUENCE: 181

Met Ser Gly Arg Leu Glu Glu Glu Leu Arg Arg Arg Leu Ser Pro Asp
1               5                   10                  15

Tyr Lys Asp Asp Asp Asp Lys Gly Ser Thr Arg Ser Val Ser Ser Ser
            20                  25                  30

Ser Tyr Arg Arg Met Phe Gly Gly Ser Gly Thr Ser Ser Arg Pro Ser
        35                  40                  45

Ser Asn Arg Ser Tyr Val Thr Thr Ser Thr Arg Thr Tyr Ser Leu Gly
    50                  55                  60

Ser Ala Leu Arg Pro Ser Thr Ser Arg Ser Leu Tyr Ser Ser Ser Pro
65                  70                  75                  80

Gly Gly Ala Tyr Val Thr Arg Ser Ser Ala Val Arg Leu Arg Ser Ser
                85                  90                  95

```
Val Pro Gly Val Arg Leu Leu Gln Asp Ser Val Asp Phe Ser Leu Ala
            100                 105                 110

Asp Ala Ile Asn Thr Glu Phe Lys Asn Thr Arg Thr Asn Glu Lys Val
            115                 120                 125

Glu Leu Gln Glu Leu Asn Asp Arg Phe Ala Asn Tyr Ile Asp Lys Val
            130                 135                 140

Arg Phe Leu Glu Gln Gln Asn Lys Ile Leu Ala Glu Leu Glu Gln
145                 150                 155                 160

Leu Lys Gly Gln Gly Lys Ser Arg Leu Gly Asp Leu Tyr Glu Glu Glu
                165                 170                 175

Met Arg Glu Leu Arg Arg Gln Val Asp Gln Leu Thr Asn Asp Lys Ala
            180                 185                 190

Arg Val Glu Val Glu Arg Asp Asn Leu Ala Glu Asp Ile Met Arg Leu
            195                 200                 205

Arg Glu Lys Leu Gln Glu Glu Met Leu Gln Arg Glu Glu Ala Glu Ser
            210                 215                 220

Thr Leu Gln Ser Phe Arg Gln Asp Val Asp Asn Ala Ser Leu Ala Arg
225                 230                 235                 240

Leu Asp Leu Glu Arg Lys Val Glu Ser Leu Gln Glu Glu Ile Ala Phe
                245                 250                 255

Leu Lys Lys Leu His Asp Glu Glu Ile Gln Glu Leu Gln Ala Gln Ile
                260                 265                 270

Gln Glu Gln His Val Gln Ile Asp Val Asp Val Ser Lys Pro Asp Leu
            275                 280                 285

Thr Ala Ala Leu Arg Asp Val Arg Gln Gln Tyr Glu Ser Val Ala Ala
            290                 295                 300

Lys Asn Leu Gln Glu Ala Glu Glu Trp Tyr Lys Ser Lys Phe Ala Asp
305                 310                 315                 320

Leu Ser Glu Ala Ala Asn Arg Asn Asn Asp Ala Leu Arg Gln Ala Lys
                325                 330                 335

Gln Glu Ser Asn Glu Tyr Arg Arg Gln Val Gln Ser Leu Thr Cys Glu
                340                 345                 350

Val Asp Ala Leu Lys Gly Thr Asn Glu Ser Leu Glu Arg Gln Met Arg
            355                 360                 365

Glu Met Glu Glu Asn Phe Ala Leu Glu Ala Ala Asn Tyr Gln Asp Thr
            370                 375                 380

Ile Gly Arg Leu Gln Asp Glu Ile Gln Asn Met Lys Glu Glu Met Ala
385                 390                 395                 400

Arg His Leu Arg Glu Tyr Gln Asp Leu Leu Asn Val Lys Met Ala Leu
                405                 410                 415

Asp Ile Glu Ile Ala Thr Tyr Arg Lys Leu Leu Glu Gly Glu Glu Ser
            420                 425                 430

Arg Ile Ser Leu Pro Leu Pro Thr Phe Ser Ser Leu Asn Leu Arg Glu
            435                 440                 445

Thr Asn Leu Glu Ser Leu Pro Leu Val Asp Thr His Ser Lys Arg Thr
            450                 455                 460

Leu Leu Ile Lys Thr Val Glu Thr Arg Asp Gly Gln Val Ile Asn Glu
465                 470                 475                 480

Thr Ser Gln His His Asp Asp Leu Glu
            485

<210> SEQ ID NO 182
<211> LENGTH: 291
```

```
<212> TYPE: PRT
<213> ORGANISM: Artificial Sequence
<220> FEATURE:
<223> OTHER INFORMATION: fusion protein

<400> SEQUENCE: 182

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Gly Asn Ser
            20                  25                  30

Pro Val Ala Thr Met Val Ser Lys Gly Glu Leu Phe Thr Gly Val
            35                  40                  45

Val Pro Ile Leu Val Glu Leu Asp Gly Asp Val Asn Gly His Lys Phe
50                  55                  60

Ser Val Ser Gly Glu Gly Glu Gly Asp Ala Thr Tyr Gly Lys Leu Thr
65                  70                  75                  80

Leu Lys Phe Ile Cys Thr Thr Gly Lys Leu Pro Val Pro Trp Pro Thr
                85                  90                  95

Leu Val Thr Thr Leu Thr Tyr Gly Val Gln Cys Phe Ser Arg Tyr Pro
            100                 105                 110

Asp His Met Lys Gln His Asp Phe Phe Lys Ser Ala Met Pro Glu Gly
        115                 120                 125

Tyr Val Gln Glu Arg Thr Ile Phe Phe Lys Asp Gly Asn Tyr Lys
130                 135                 140

Thr Arg Ala Glu Val Lys Phe Glu Gly Asp Thr Leu Val Asn Arg Ile
145                 150                 155                 160

Glu Leu Lys Gly Ile Asp Phe Lys Glu Asp Gly Asn Ile Leu Gly His
                165                 170                 175

Lys Leu Glu Tyr Asn Tyr Asn Ser His Asn Val Tyr Ile Met Ala Asp
            180                 185                 190

Lys Gln Lys Asn Gly Ile Lys Val Asn Phe Lys Ile Arg His Asn Ile
        195                 200                 205

Glu Asp Gly Ser Val Gln Leu Ala Asp His Tyr Gln Gln Asn Thr Pro
210                 215                 220

Ile Gly Asp Gly Pro Val Leu Leu Pro Asp Asn His Tyr Leu Ser Thr
225                 230                 235                 240

Gln Ser Lys Leu Ser Lys Asp Pro Asn Glu Lys Arg Asp His Met Val
                245                 250                 255

Leu Leu Glu Phe Val Thr Ala Ala Gly Ile Thr Leu Gly Met Asp Glu
            260                 265                 270

Leu Tyr Lys Gly Ser Pro Ser Arg Leu Glu Glu Leu Arg Arg Arg
        275                 280                 285

Leu Thr Glu
    290

<210> SEQ ID NO 183
<211> LENGTH: 291
<212> TYPE: PRT
<213> ORGANISM: Artificial Sequence
<220> FEATURE:
<223> OTHER INFORMATION: fusion protein

<400> SEQUENCE: 183

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Gly Asn Ser
            20                  25                  30
```

```
Pro Val Ala Thr Met Val Ser Lys Gly Glu Glu Leu Phe Thr Gly Val
            35                  40                  45

Val Pro Ile Leu Val Glu Leu Asp Gly Asp Val Asn Gly His Lys Phe
 50                  55                  60

Ser Val Ser Gly Glu Gly Glu Gly Asp Ala Thr Tyr Gly Lys Leu Thr
 65                  70                  75                  80

Leu Lys Phe Ile Cys Thr Thr Gly Lys Leu Pro Val Pro Trp Pro Thr
                85                  90                  95

Leu Val Thr Thr Leu Thr Tyr Gly Val Gln Cys Phe Ser Arg Tyr Pro
                100                 105                 110

Asp His Met Lys Gln His Asp Phe Phe Lys Ser Ala Met Pro Glu Gly
            115                 120                 125

Tyr Val Gln Glu Arg Thr Ile Phe Phe Lys Asp Asp Gly Asn Tyr Lys
            130                 135                 140

Thr Arg Ala Glu Val Lys Phe Glu Gly Asp Thr Leu Val Asn Arg Ile
145                 150                 155                 160

Glu Leu Lys Gly Ile Asp Phe Lys Glu Asp Gly Asn Ile Leu Gly His
                165                 170                 175

Lys Leu Glu Tyr Asn Tyr Asn Ser His Asn Val Tyr Ile Met Ala Asp
            180                 185                 190

Lys Gln Lys Asn Gly Ile Lys Val Asn Phe Lys Ile Arg His Asn Ile
            195                 200                 205

Glu Asp Gly Ser Val Gln Leu Ala Asp His Tyr Gln Gln Asn Thr Pro
            210                 215                 220

Ile Gly Asp Gly Pro Val Leu Leu Pro Asp Asn His Tyr Leu Ser Thr
225                 230                 235                 240

Gln Ser Lys Leu Ser Lys Asp Pro Asn Glu Lys Arg Asp His Met Val
                245                 250                 255

Leu Leu Glu Phe Val Thr Ala Ala Gly Ile Thr Leu Gly Met Asp Glu
                260                 265                 270

Leu Tyr Lys Gly Ser Pro Ser Arg Leu Glu Glu Leu Arg Arg Arg
            275                 280                 285

Leu Thr Glu
    290

<210> SEQ ID NO 184
<211> LENGTH: 350
<212> TYPE: PRT
<213> ORGANISM: Artificial Sequence
<220> FEATURE:
<223> OTHER INFORMATION: fusion protein

<400> SEQUENCE: 184

Met Glu Thr Asp Thr Leu Leu Leu Trp Val Leu Leu Leu Trp Val Pro
 1               5                  10                  15

Gly Ser Thr Gly Asp Tyr Pro Tyr Asp Val Pro Asp Tyr Ala Ser Asn
            20                  25                  30

Gly Thr Ser Lys Gly Glu Glu Leu Phe Thr Gly Val Val Pro Ile Leu
            35                  40                  45

Val Glu Leu Asp Gly Asp Val Asn Gly His Lys Phe Ser Val Ser Gly
 50                  55                  60

Glu Gly Glu Gly Asp Ala Thr Tyr Gly Lys Leu Thr Leu Lys Phe Ile
 65                  70                  75                  80

Cys Thr Thr Gly Lys Leu Pro Val Pro Trp Pro Thr Leu Val Thr Thr
                85                  90                  95
```

Leu Thr Tyr Gly Val Gln Cys Phe Ser Arg Tyr Pro Asp His Met Lys
                100                 105                 110

Gln His Asp Phe Phe Lys Ser Ala Met Pro Glu Gly Tyr Val Gln Glu
            115                 120                 125

Arg Thr Ile Phe Phe Lys Asp Asp Gly Asn Tyr Lys Thr Arg Ala Glu
130                 135                 140

Val Lys Phe Glu Gly Asp Thr Leu Val Asn Arg Ile Glu Leu Lys Gly
145                 150                 155                 160

Ile Asp Phe Lys Glu Asp Gly Asn Ile Leu Gly His Lys Leu Glu Tyr
                165                 170                 175

Asn Tyr Asn Ser His Asn Val Tyr Ile Met Ala Asp Lys Gln Lys Asn
            180                 185                 190

Gly Ile Lys Val Asn Phe Lys Ile Arg His Asn Ile Glu Asp Gly Ser
        195                 200                 205

Val Gln Leu Ala Asp His Tyr Gln Gln Asn Thr Pro Ile Gly Asp Gly
    210                 215                 220

Pro Val Leu Leu Pro Asp Asn His Tyr Leu Ser Thr Gln Ser Ala Leu
225                 230                 235                 240

Ser Lys Asp Pro Asn Glu Lys Arg Asp His Met Val Leu Lys Glu Phe
                245                 250                 255

Val Thr Ala Ala Gly Ile Thr Leu Gly Met Asp Glu Leu Tyr Lys Gly
            260                 265                 270

Ser Pro Ser Arg Leu Glu Glu Glu Leu Arg Arg Leu Thr Glu Pro
        275                 280                 285

Gly Asp Glu Gln Lys Leu Ile Ser Glu Glu Asp Leu Asn Ala Val Gly
    290                 295                 300

Gln Asp Thr Gln Glu Val Ile Val Val Pro His Ser Leu Pro Phe Lys
305                 310                 315                 320

Val Val Val Ile Ser Ala Ile Leu Ala Leu Val Val Leu Thr Ile Ile
                325                 330                 335

Ser Leu Ile Ile Leu Ile Met Leu Trp Gln Lys Lys Pro Arg
            340                 345                 350

<210> SEQ ID NO 185
<211> LENGTH: 382
<212> TYPE: PRT
<213> ORGANISM: Artificial Sequence
<220> FEATURE:
<223> OTHER INFORMATION: fusion protein

<400> SEQUENCE: 185

Met Gly Ser Gly Asp Ala Ser Asp Ser Glu Val Gln Leu Gln Glu Ser
1               5                   10                  15

Gly Gly Gly Leu Val Gln Pro Gly Gly Ser Leu Arg Leu Ser Cys Thr
            20                  25                  30

Ala Ser Gly Val Thr Ile Ser Ala Leu Asn Ala Met Ala Met Gly Trp
        35                  40                  45

Tyr Arg Gln Ala Pro Gly Glu Arg Arg Val Met Val Ala Ala Val Ser
    50                  55                  60

Glu Arg Gly Asn Ala Met Tyr Arg Glu Ser Val Gln Gly Arg Phe Thr
65                  70                  75                  80

Val Thr Arg Asp Phe Thr Asn Lys Met Val Ser Leu Gln Met Asp Asn
                85                  90                  95

Leu Lys Pro Glu Asp Thr Ala Val Tyr Tyr Cys His Val Leu Glu Asp
            100                 105                 110

```
Arg Val Asp Ser Phe His Asp Tyr Trp Gly Gln Gly Thr Gln Val Thr
            115                 120                 125

Val Ser Ser Glu Pro Lys Thr Pro Lys Pro Gln Thr Ser Gly Ser Thr
130                 135                 140

Gly Glu Asn Val Ala Thr Met Val Ser Lys Gly Glu Ala Val Ile Lys
145                 150                 155                 160

Glu Phe Met Arg Phe Lys Val His Met Glu Gly Ser Met Asn Gly His
                165                 170                 175

Glu Phe Glu Ile Glu Gly Gly Gly Arg Pro Tyr Glu Gly Thr
            180                 185                 190

Gln Thr Ala Lys Leu Lys Val Thr Lys Gly Gly Pro Leu Pro Phe Ser
            195                 200                 205

Trp Asp Ile Leu Ser Pro Gln Phe Met Tyr Gly Ser Arg Ala Phe Ile
210                 215                 220

Lys His Pro Ala Asp Ile Pro Asp Tyr Tyr Lys Gln Ser Phe Pro Glu
225                 230                 235                 240

Gly Phe Lys Trp Glu Arg Val Met Asn Phe Glu Asp Gly Gly Ala Val
                245                 250                 255

Thr Val Thr Gln Asp Thr Ser Leu Glu Asp Gly Thr Leu Ile Tyr Lys
            260                 265                 270

Val Lys Leu Arg Gly Thr Asn Phe Pro Pro Asp Gly Pro Val Met Gln
            275                 280                 285

Lys Lys Thr Met Gly Trp Glu Ala Ser Thr Glu Arg Leu Tyr Pro Glu
            290                 295                 300

Asp Gly Val Leu Lys Gly Asp Ile Lys Met Ala Leu Arg Leu Lys Asp
305                 310                 315                 320

Gly Gly Arg Tyr Leu Ala Asp Phe Lys Thr Thr Tyr Lys Ala Lys Lys
                325                 330                 335

Pro Val Gln Met Pro Gly Ala Tyr Asn Val Asp Arg Lys Leu Asp Ile
            340                 345                 350

Thr Ser His Asn Glu Asp Tyr Thr Val Val Glu Gln Tyr Glu Arg Ser
            355                 360                 365

Glu Gly Arg His Ser Thr Gly Gly Met Asp Glu Leu Tyr Lys
            370                 375                 380

<210> SEQ ID NO 186
<211> LENGTH: 239
<212> TYPE: PRT
<213> ORGANISM: Artificial Sequence
<220> FEATURE:
<223> OTHER INFORMATION: EGFP

<400> SEQUENCE: 186

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 187
<211> LENGTH: 255
<212> TYPE: PRT
<213> ORGANISM: Artificial Sequence
<220> FEATURE:
<223> OTHER INFORMATION: fusion protein

<400> SEQUENCE: 187

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

```
Val Thr Ala Ala Gly Ile Thr Leu Gly Met Asp Glu Leu Tyr Lys Gly
225                 230                 235                 240

Ser Pro Ser Arg Leu Glu Glu Glu Leu Arg Arg Leu Thr Glu
                245                 250                 255
```

<210> SEQ ID NO 188
<211> LENGTH: 255
<212> TYPE: PRT
<213> ORGANISM: Artificial Sequence
<220> FEATURE:
<223> OTHER INFORMATION: fusion protein

<400> SEQUENCE: 188

```
Met Pro Ser Arg Leu Glu Glu Glu Leu Arg Arg Leu Thr Glu Pro
1               5                   10                  15

Met Val Ser Lys Gly Glu Glu Leu Phe Thr Gly Val Val Pro Ile Leu
                20                  25                  30

Val Glu Leu Asp Gly Asp Val Asn Gly His Lys Phe Ser Val Ser Gly
            35                  40                  45

Glu Gly Glu Gly Asp Ala Thr Tyr Gly Lys Leu Thr Leu Lys Phe Ile
50                  55                  60

Cys Thr Thr Gly Lys Leu Pro Val Pro Trp Pro Thr Leu Val Thr Thr
65                  70                  75                  80

Leu Thr Tyr Gly Val Gln Cys Phe Ser Arg Tyr Pro Asp His Met Lys
                85                  90                  95

Gln His Asp Phe Phe Lys Ser Ala Met Pro Glu Gly Tyr Val Gln Glu
            100                 105                 110

Arg Thr Ile Phe Phe Lys Asp Asp Gly Asn Tyr Lys Thr Arg Ala Glu
        115                 120                 125

Val Lys Phe Glu Gly Asp Thr Leu Val Asn Arg Ile Glu Leu Lys Gly
130                 135                 140

Ile Asp Phe Lys Glu Asp Gly Asn Ile Leu Gly His Lys Leu Glu Tyr
145                 150                 155                 160

Asn Tyr Asn Ser His Asn Val Tyr Ile Met Ala Asp Lys Gln Lys Asn
                165                 170                 175

Gly Ile Lys Val Asn Phe Lys Ile Arg His Asn Ile Glu Asp Gly Ser
            180                 185                 190

Val Gln Leu Ala Asp His Tyr Gln Gln Asn Thr Pro Ile Gly Asp Gly
        195                 200                 205

Pro Val Leu Leu Pro Asp Asn His Tyr Leu Ser Thr Gln Ser Ala Leu
210                 215                 220

Ser Lys Asp Pro Asn Glu Lys Arg Asp His Met Val Leu Leu Glu Phe
225                 230                 235                 240

Val Thr Ala Ala Gly Ile Thr Leu Gly Met Asp Glu Leu Tyr Lys
                245                 250                 255
```

<210> SEQ ID NO 189
<211> LENGTH: 558
<212> TYPE: PRT
<213> ORGANISM: Artificial Sequence
<220> FEATURE:
<223> OTHER INFORMATION: fusion protein

<400> SEQUENCE: 189

```
Met Ser Lys His His His His Ser Asn His His Arg His Asn His His
1               5                   10                  15

His His Ser Gly Asn His His His Ser Gly Ser Ala Ala Gly Gly Glu
```

```
            20                  25                  30
Glu Asp Lys Lys Pro Ala Gly Gly Glu Gly Gly Gly Ala His Ile Asn
        35                  40                  45

Leu Lys Val Lys Gly Gln Asp Gly Asn Glu Val Phe Phe Arg Ile Lys
    50                  55                  60

Arg Ser Thr Gln Leu Lys Leu Met Asn Ala Tyr Cys Asp Arg Gln
65                  70                  75                  80

Ser Val Asp Met Thr Ala Ile Ala Phe Leu Phe Asp Gly Arg Arg Leu
                85                  90                  95

Arg Ala Glu Gln Thr Pro Asp Glu Leu Glu Met Glu Asp Gly Asp Glu
            100                 105                 110

Ile Asp Ala Met Leu His Gln Thr Gly Gly Ala Ser Asp Tyr Lys Asp
            115                 120                 125

Asp Asp Asp Lys Gly Ser Thr Gly Asp Tyr Pro Tyr Asp Val Pro Asp
        130                 135                 140

Tyr Ala Ser Asn Gly Thr Lys Thr Glu Glu Gly Lys Leu Val Ile Trp
145                 150                 155                 160

Ile Asn Gly Asp Lys Gly Tyr Asn Gly Leu Ala Glu Val Gly Lys Lys
                165                 170                 175

Phe Glu Lys Asp Thr Gly Ile Lys Val Thr Val Glu His Pro Asp Lys
            180                 185                 190

Leu Glu Glu Lys Phe Pro Gln Val Ala Ala Thr Gly Asp Gly Pro Asp
        195                 200                 205

Ile Ile Phe Trp Ala His Asp Arg Phe Gly Gly Tyr Ala Gln Ser Gly
        210                 215                 220

Leu Leu Ala Glu Ile Thr Pro Asp Lys Ala Phe Gln Asp Lys Leu Tyr
225                 230                 235                 240

Pro Phe Thr Trp Asp Ala Val Arg Tyr Asn Gly Lys Leu Ile Ala Tyr
                245                 250                 255

Pro Ile Ala Val Glu Ala Leu Ser Leu Ile Tyr Asn Lys Asp Leu Leu
            260                 265                 270

Pro Asn Pro Pro Lys Thr Trp Glu Glu Ile Pro Ala Leu Asp Lys Glu
        275                 280                 285

Leu Lys Ala Lys Gly Lys Ser Ala Leu Met Phe Asn Leu Gln Glu Pro
        290                 295                 300

Tyr Phe Thr Trp Pro Leu Ile Ala Ala Asp Gly Gly Tyr Ala Phe Lys
305                 310                 315                 320

Tyr Glu Asn Gly Lys Tyr Asp Ile Lys Asp Val Gly Val Asp Asn Ala
                325                 330                 335

Gly Ala Lys Ala Gly Leu Thr Phe Leu Val Asp Leu Ile Lys Asn Lys
            340                 345                 350

His Met Asn Ala Asp Thr Asp Tyr Ser Ile Ala Glu Ala Ala Phe Asn
        355                 360                 365

Lys Gly Glu Thr Ala Met Thr Ile Asn Gly Pro Trp Ala Trp Ser Asn
        370                 375                 380

Ile Asp Thr Ser Lys Val Asn Tyr Gly Val Thr Val Leu Pro Thr Phe
385                 390                 395                 400

Lys Gly Gln Pro Ser Lys Pro Phe Val Gly Val Leu Ser Ala Gly Ile
                405                 410                 415

Asn Ala Ala Ser Pro Asn Lys Glu Leu Ala Lys Glu Phe Leu Glu Asn
            420                 425                 430

Tyr Leu Leu Thr Asp Glu Gly Leu Glu Ala Val Asn Lys Asp Lys Pro
        435                 440                 445
```

Leu Gly Ala Val Ala Leu Lys Ser Tyr Glu Glu Leu Ala Lys Asp
    450                 455                 460

Pro Arg Ile Ala Ala Thr Met Glu Asn Ala Gln Lys Gly Glu Ile Met
465                 470                 475                 480

Pro Asn Ile Pro Gln Met Ser Ala Phe Trp Tyr Ala Val Arg Thr Ala
                485                 490                 495

Val Ile Asn Ala Ala Ser Gly Arg Gln Thr Val Asp Glu Ala Leu Lys
                500                 505                 510

Asp Ala Gln Thr Asn Gly Ser Val Ser Ala Gly Asp Glu Gln Lys Leu
            515                 520                 525

Ile Ser Glu Glu Asp Leu Asn Ala Val Gly Gln Asp Thr Ala Ser Thr
    530                 535                 540

Pro Ser Arg Leu Glu Glu Glu Leu Arg Arg Arg Leu Thr Glu
545                 550                 555

<210> SEQ ID NO 190
<211> LENGTH: 259
<212> TYPE: PRT
<213> ORGANISM: Artificial Sequence
<220> FEATURE:
<223> OTHER INFORMATION: fusion protein

<400> SEQUENCE: 190

Met Pro Ser Arg Leu Glu Glu Glu Leu Arg Arg Leu Thr Glu Pro
1               5                   10                  15

Ser Lys Gly Glu Glu Leu Phe Thr Gly Thr Val Pro Ile Lys Val Glu
                20                  25                  30

Leu Asp Gly Asp Val Asn Gly His Lys Phe Ser Val Arg Gly Glu Gly
            35                  40                  45

Glu Gly Asp Ala Thr Glu Gly Lys Leu Thr Leu Lys Phe Ile Cys Thr
    50                  55                  60

Thr Gly Lys Leu Pro Val Pro Trp Pro Thr Leu Val Thr Thr Leu Thr
65                  70                  75                  80

Tyr Gly Val Gln Cys Phe Ser Arg Tyr Pro Asp His Met Lys Arg His
                85                  90                  95

Asp Phe Phe Lys Ser Ala Met Pro Glu Gly Tyr Val Gln Glu Arg Thr
                100                 105                 110

Ile Glu Phe Lys Asp Asp Gly Thr Tyr Lys Thr Arg Ala Glu Val Lys
            115                 120                 125

Phe Glu Gly Asp Thr Leu Val Asn Arg Ile Glu Leu Lys Gly Asn Asp
    130                 135                 140

Phe Lys Glu Asp Gly Asn Ile Leu Gly His Lys Leu Glu Tyr Asn His
145                 150                 155                 160

Asn Ser His Asn Val Arg Ile Glu Ala Asp Lys Gln Lys Asn Gly Ile
                165                 170                 175

Lys Ala Asn Phe Lys Ile Arg His Asn Val Glu Asp Gly Ser Gln Gln
            180                 185                 190

Glu Ala Asp His Lys Gln Gln Asn Thr Pro Ile Gly Asp Gly Pro Val
    195                 200                 205

Arg Leu Pro Asp Asn His Tyr Leu Ser Thr Gln Thr Thr Leu Ser Lys
210                 215                 220

Asp Pro Asn Glu Lys Arg Asp His Met Val Leu Lys Glu Phe Val Thr
225                 230                 235                 240

Ala Ala Gly Ile Thr Lys Gly Glu Asp Glu Arg Asp Lys His His His
                245                 250                 255

His His His

<210> SEQ ID NO 191
<211> LENGTH: 258
<212> TYPE: PRT
<213> ORGANISM: Artificial Sequence
<220> FEATURE:
<223> OTHER INFORMATION: fusion protein

<400> SEQUENCE: 191

```
Met Ser Gly Arg Leu Glu Glu Leu Arg Arg Leu Ser Pro Ser
1               5                   10                  15

Lys Gly Glu Glu Leu Phe Thr Gly Thr Val Pro Ile Lys Val Glu Leu
            20                  25                  30

Asp Gly Asp Val Asn Gly His Lys Phe Ser Val Arg Gly Glu Gly Glu
        35                  40                  45

Gly Asp Ala Thr Glu Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Glu Phe Lys Asp Asp Gly Thr Tyr Lys Thr Arg Ala Glu Val Lys Phe
        115                 120                 125

Glu Gly Asp Thr Leu Val Asn Arg Ile Glu Leu Lys Gly Asn Asp Phe
    130                 135                 140

Lys Glu Asp Gly Asn Ile Leu Gly His Lys Leu Glu Tyr Asn His Asn
145                 150                 155                 160

Ser His Asn Val Arg Ile Glu Ala Asp Lys Gln Lys Asn Gly Ile Lys
                165                 170                 175

Ala Asn Phe Lys Ile Arg His Asn Val Glu Asp Gly Ser Gln Gln Glu
            180                 185                 190

Ala Asp His Lys Gln Gln Asn Thr Pro Ile Gly Asp Gly Pro Val Arg
        195                 200                 205

Leu Pro Asp Asn His Tyr Leu Ser Thr Gln Thr Thr Leu Ser Lys Asp
    210                 215                 220

Pro Asn Glu Lys Arg Asp His Met Val Leu Glu Phe Val Thr Ala
225                 230                 235                 240

Ala Gly Ile Thr Lys Gly Glu Asp Glu Arg Asp Lys His His His His
                245                 250                 255

His His
```

<210> SEQ ID NO 192
<211> LENGTH: 381
<212> TYPE: PRT
<213> ORGANISM: Artificial Sequence
<220> FEATURE:
<223> OTHER INFORMATION: fusion protein

<400> SEQUENCE: 192

```
Met Ser Lys His His His His Ser Asn His Arg His Asn His His
1               5                   10                  15

His His Ser Gly Asn His His Ser Gly Ser Ala Ala Gly Gly Glu
            20                  25                  30
```

Glu Asp Lys Pro Ala Gly Gly Glu Gly Gly Ala His Ile Asn
            35                  40                  45

Leu Lys Val Lys Gly Gln Asp Gly Asn Glu Val Phe Phe Arg Ile Lys
 50                  55                  60

Arg Ser Thr Gln Leu Lys Lys Leu Met Asn Ala Tyr Cys Asp Arg Gln
 65                  70                  75                  80

Ser Val Asp Met Thr Ala Ile Ala Phe Leu Phe Asp Gly Arg Arg Leu
                85                  90                  95

Arg Ala Glu Gln Thr Pro Asp Glu Leu Glu Met Glu Asp Gly Asp Glu
            100                 105                 110

Ile Asp Ala Met Leu His Gln Thr Gly Gly Gly Ser Lys Gly Glu Glu
            115                 120                 125

Leu Phe Thr Gly Thr Val Pro Ile Lys Val Glu Leu Asp Gly Asp Val
130                 135                 140

Asn Gly His Lys Phe Ser Val Arg Gly Glu Gly Gly Asp Ala Thr
145                 150                 155                 160

Glu Gly Lys Leu Thr Leu Lys Phe Ile Cys Thr Thr Gly Lys Leu Pro
                165                 170                 175

Val Pro Trp Pro Thr Leu Val Thr Thr Leu Thr Tyr Gly Val Gln Cys
            180                 185                 190

Phe Ser Arg Tyr Pro Asp His Met Lys Arg His Asp Phe Phe Lys Ser
        195                 200                 205

Ala Met Pro Glu Gly Tyr Val Gln Glu Arg Thr Ile Glu Phe Lys Asp
    210                 215                 220

Asp Gly Thr Tyr Lys Thr Arg Ala Glu Val Lys Phe Glu Gly Asp Thr
225                 230                 235                 240

Leu Val Asn Arg Ile Glu Leu Lys Gly Asn Asp Phe Lys Glu Asp Gly
                245                 250                 255

Asn Ile Leu Gly His Lys Leu Glu Tyr Asn His Asn Ser His Asn Val
            260                 265                 270

Arg Ile Glu Ala Asp Lys Gln Lys Asn Gly Ile Lys Ala Asn Phe Lys
        275                 280                 285

Ile Arg His Asn Val Glu Asp Gly Ser Gln Gln Glu Ala Asp His Lys
    290                 295                 300

Gln Gln Asn Thr Pro Ile Gly Asp Gly Pro Val Arg Leu Pro Asp Asn
305                 310                 315                 320

His Tyr Leu Ser Thr Gln Thr Thr Leu Ser Lys Asp Pro Asn Glu Lys
                325                 330                 335

Arg Asp His Met Val Leu Lys Glu Phe Val Thr Ala Ala Gly Ile Thr
            340                 345                 350

Lys Gly Glu Asp Glu Arg Asp Lys Gly Ser Gly Asn Ser Asp Gly Pro
        355                 360                 365

Ser Arg Leu Glu Glu Glu Leu Arg Arg Leu Thr Glu
    370                 375                 380

<210> SEQ ID NO 193
<211> LENGTH: 382
<212> TYPE: PRT
<213> ORGANISM: Artificial Sequence
<220> FEATURE:
<223> OTHER INFORMATION: fusion protein

<400> SEQUENCE: 193

Met Ser Lys His His His His Ser Asn His Arg His Asn His His
1               5                   10                  15

His His Ser Gly Asn His His Ser Gly Ser Ala Ala Gly Gly Glu
          20                  25                  30

Glu Asp Lys Lys Pro Ala Gly Gly Glu Gly Gly Ala His Ile Asn
         35                  40                  45

Leu Lys Val Lys Gly Gln Asp Gly Asn Glu Val Phe Phe Arg Ile Lys
 50                  55                  60

Arg Ser Thr Gln Leu Lys Lys Leu Met Asn Ala Tyr Cys Asp Arg Gln
65                  70                  75                  80

Ser Val Asp Met Thr Ala Ile Ala Phe Leu Phe Asp Gly Arg Arg Leu
                 85                  90                  95

Arg Ala Glu Gln Thr Pro Asp Glu Leu Glu Met Glu Asp Gly Asp Glu
            100                 105                 110

Ile Asp Ala Met Leu His Gln Thr Gly Gly Gly Ser Lys Gly Glu Glu
        115                 120                 125

Leu Phe Thr Gly Thr Val Pro Ile Lys Val Glu Leu Asp Gly Asp Val
    130                 135                 140

Asn Gly His Lys Phe Ser Val Arg Gly Glu Gly Glu Gly Asp Ala Thr
145                 150                 155                 160

Glu Gly Lys Leu Thr Leu Lys Phe Ile Cys Thr Thr Gly Lys Leu Pro
                165                 170                 175

Val Pro Trp Pro Thr Leu Val Thr Thr Leu Thr Tyr Gly Val Gln Cys
            180                 185                 190

Phe Ser Arg Tyr Pro Asp His Met Lys Arg His Asp Phe Phe Lys Ser
        195                 200                 205

Ala Met Pro Glu Gly Tyr Val Gln Glu Arg Thr Ile Glu Phe Lys Asp
    210                 215                 220

Asp Gly Thr Tyr Lys Thr Arg Ala Glu Val Lys Phe Glu Gly Asp Thr
225                 230                 235                 240

Leu Val Asn Arg Ile Glu Leu Lys Gly Asn Asp Phe Lys Glu Asp Gly
                245                 250                 255

Asn Ile Leu Gly His Lys Leu Glu Tyr Asn His Asn Ser His Asn Val
        260                 265                 270

Arg Ile Glu Ala Asp Lys Gln Lys Asn Gly Ile Lys Ala Asn Phe Lys
    275                 280                 285

Ile Arg His Asn Val Glu Asp Gly Ser Gln Gln Glu Ala Asp His Lys
290                 295                 300

Gln Gln Asn Thr Pro Ile Gly Asp Gly Pro Val Arg Leu Pro Asp Asn
305                 310                 315                 320

His Tyr Leu Ser Thr Gln Thr Thr Leu Ser Lys Asp Pro Asn Glu Lys
                325                 330                 335

Arg Asp His Met Val Leu Lys Glu Phe Val Thr Ala Ala Gly Ile Thr
        340                 345                 350

Lys Gly Glu Asp Glu Arg Asp Lys Gly Ser Gly Asn Ser Asp Gly Met
    355                 360                 365

Ser Gly Arg Leu Glu Glu Glu Leu Arg Arg Leu Ser Pro
370                 375                 380

<210> SEQ ID NO 194
<211> LENGTH: 382
<212> TYPE: PRT
<213> ORGANISM: Artificial Sequence
<220> FEATURE:
<223> OTHER INFORMATION: fusion protein

<400> SEQUENCE: 194

```
Met Ser Lys His His His Ser Asn His Arg His Asn His His
 1               5                  10                  15

His His Ser Gly Asn His His Ser Gly Ser Ala Ala Gly Gly Glu
            20                  25                  30

Glu Asp Lys Lys Pro Ala Gly Gly Glu Gly Gly Gly Ala His Ile Asn
        35                  40                  45

Leu Lys Val Lys Gly Gln Asp Gly Asn Glu Val Phe Phe Arg Ile Lys
    50                  55                  60

Arg Ser Thr Gln Leu Lys Lys Leu Met Asn Ala Tyr Cys Asp Arg Gln
65                  70                  75                  80

Ser Val Asp Met Thr Ala Ile Ala Phe Leu Phe Asp Gly Arg Arg Leu
                85                  90                  95

Arg Ala Glu Gln Thr Pro Asp Glu Leu Glu Met Glu Asp Gly Asp Glu
                100                 105                 110

Ile Asp Ala Met Leu His Gln Thr Gly Gly Ser Gly Asp Ala Ser Asp
            115                 120                 125

Ser Pro Ser Arg Leu Glu Glu Leu Arg Arg Leu Thr Glu Pro
    130                 135                 140

Ser Lys Gly Glu Glu Leu Phe Thr Gly Thr Val Pro Ile Lys Val Glu
145                 150                 155                 160

Leu Asp Gly Asp Val Asn Gly His Lys Phe Ser Val Arg Gly Glu Gly
                165                 170                 175

Glu Gly Asp Ala Thr Glu Gly Lys Leu Thr Leu Lys Phe Ile Cys Thr
            180                 185                 190

Thr Gly Lys Leu Pro Val Pro Trp Pro Thr Leu Val Thr Thr Leu Thr
        195                 200                 205

Tyr Gly Val Gln Cys Phe Ser Arg Tyr Pro Asp His Met Lys Arg His
    210                 215                 220

Asp Phe Phe Lys Ser Ala Met Pro Glu Gly Tyr Val Gln Glu Arg Thr
225                 230                 235                 240

Ile Glu Phe Lys Asp Asp Gly Thr Tyr Lys Thr Arg Ala Glu Val Lys
                245                 250                 255

Phe Glu Gly Asp Thr Leu Val Asn Arg Ile Glu Leu Lys Gly Asn Asp
            260                 265                 270

Phe Lys Glu Asp Gly Asn Ile Leu Gly His Lys Leu Glu Tyr Asn His
        275                 280                 285

Asn Ser His Asn Val Arg Ile Glu Ala Asp Lys Gln Lys Asn Gly Ile
    290                 295                 300

Lys Ala Asn Phe Lys Ile Arg His Asn Val Glu Asp Gly Ser Gln Gln
305                 310                 315                 320

Glu Ala Asp His Lys Gln Gln Asn Thr Pro Ile Gly Asp Gly Pro Val
                325                 330                 335

Arg Leu Pro Asp Asn His Tyr Leu Ser Thr Gln Thr Leu Ser Lys
            340                 345                 350

Asp Pro Asn Glu Lys Arg Asp His Met Val Leu Lys Glu Phe Val Thr
        355                 360                 365

Ala Ala Gly Ile Thr Lys Gly Glu Asp Glu Arg Asp Lys Ala
    370                 375                 380

<210> SEQ ID NO 195
<211> LENGTH: 382
<212> TYPE: PRT
<213> ORGANISM: Artificial Sequence
<220> FEATURE:
<223> OTHER INFORMATION: fusion protein
```

<400> SEQUENCE: 195

Met Ser Lys His His His Ser Asn His Arg His Asn His His
1               5                   10                  15

His His Ser Gly Asn His His Ser Gly Ser Ala Ala Gly Gly Glu
            20                  25                  30

Glu Asp Lys Lys Pro Ala Gly Gly Glu Gly Gly Gly Ala His Ile Asn
        35                  40                  45

Leu Lys Val Lys Gly Gln Asp Gly Asn Glu Val Phe Phe Arg Ile Lys
    50                  55                  60

Arg Ser Thr Gln Leu Lys Lys Leu Met Asn Ala Tyr Cys Asp Arg Gln
65                  70                  75                  80

Ser Val Asp Met Thr Ala Ile Ala Phe Leu Phe Asp Gly Arg Arg Leu
                85                  90                  95

Arg Ala Glu Gln Thr Pro Asp Glu Leu Glu Met Glu Asp Gly Asp Glu
            100                 105                 110

Ile Asp Ala Met Leu His Gln Thr Gly Gly Ser Gly Asp Ala Ser Asp
        115                 120                 125

Ser Met Ser Gly Arg Leu Glu Glu Glu Leu Arg Arg Arg Leu Ser Pro
130                 135                 140

Ser Lys Gly Glu Glu Leu Phe Thr Gly Thr Val Pro Ile Lys Val Glu
145                 150                 155                 160

Leu Asp Gly Asp Val Asn Gly His Lys Phe Ser Val Arg Gly Glu Gly
                165                 170                 175

Glu Gly Asp Ala Thr Glu Gly Lys Leu Thr Leu Lys Phe Ile Cys Thr
            180                 185                 190

Thr Gly Lys Leu Pro Val Pro Trp Pro Thr Leu Val Thr Thr Leu Thr
        195                 200                 205

Tyr Gly Val Gln Cys Phe Ser Arg Tyr Pro Asp His Met Lys Arg His
    210                 215                 220

Asp Phe Phe Lys Ser Ala Met Pro Glu Gly Tyr Val Gln Glu Arg Thr
225                 230                 235                 240

Ile Glu Phe Lys Asp Asp Gly Thr Tyr Lys Thr Arg Ala Glu Val Lys
                245                 250                 255

Phe Glu Gly Asp Thr Leu Val Asn Arg Ile Glu Leu Lys Gly Asn Asp
            260                 265                 270

Phe Lys Glu Asp Gly Asn Ile Leu Gly His Lys Leu Glu Tyr Asn His
        275                 280                 285

Asn Ser His Asn Val Arg Ile Glu Ala Asp Lys Gln Lys Asn Gly Ile
    290                 295                 300

Lys Ala Asn Phe Lys Ile Arg His Asn Val Glu Asp Gly Ser Gln Gln
305                 310                 315                 320

Glu Ala Asp His Lys Gln Gln Asn Thr Pro Ile Gly Asp Gly Pro Val
                325                 330                 335

Arg Leu Pro Asp Asn His Tyr Leu Ser Thr Gln Thr Thr Leu Ser Lys
            340                 345                 350

Asp Pro Asn Glu Lys Arg Asp His Met Val Leu Lys Glu Phe Val Thr
        355                 360                 365

Ala Ala Gly Ile Thr Lys Gly Glu Asp Glu Arg Asp Lys Ala
    370                 375                 380

<210> SEQ ID NO 196
<211> LENGTH: 222
<212> TYPE: PRT

<213> ORGANISM: Artificial Sequence
<220> FEATURE:
<223> OTHER INFORMATION: fusion protein

<400> SEQUENCE: 196

```
Met Glu Ile Tyr Glu Asn Glu Asn Asp Gln Val Glu Ala Val Lys Arg
1               5                   10                  15

Phe Phe Ala Glu Asn Gly Lys Ala Leu Ala Val Gly Val Ile Leu Gly
                20                  25                  30

Val Gly Ala Leu Ile Gly Trp Arg Tyr Trp Asn Ser His Gln Val Asp
            35                  40                  45

Ser Ala Arg Ser Ala Ser Leu Ala Tyr Gln Asn Ala Val Thr Ala Val
50                  55                  60

Ser Glu Gly Lys Pro Asp Ser Ile Pro Ala Ala Glu Lys Phe Ala Ala
65                  70                  75                  80

Glu Asn Lys Asn Thr Tyr Gly Ala Leu Ala Ser Leu Glu Leu Ala Gln
                85                  90                  95

Gln Phe Val Asp Lys Asn Glu Leu Glu Lys Ala Ala Gln Leu Gln
                100                 105                 110

Gln Gly Leu Ala Asp Thr Ser Asp Glu Asn Leu Lys Ala Val Ile Asn
            115                 120                 125

Leu Arg Leu Ala Arg Val Gln Val Gln Leu Lys Gln Ala Asp Ala Ala
130                 135                 140

Leu Lys Thr Leu Asp Thr Ile Lys Gly Glu Gly Trp Ala Ala Ile Val
145                 150                 155                 160

Ala Asp Leu Arg Gly Glu Ala Leu Leu Ser Lys Gly Asp Lys Gln Gly
                165                 170                 175

Ala Arg Ser Ala Trp Glu Ala Gly Val Lys Ser Asp Val Thr Pro Ala
            180                 185                 190

Leu Ser Glu Met Met Gln Met Lys Ile Asn Asn Leu Ser Ile Gly Ser
            195                 200                 205

Pro Ser Arg Leu Glu Glu Leu Arg Arg Leu Thr Glu
210                 215                 220
```

<210> SEQ ID NO 197
<211> LENGTH: 222
<212> TYPE: PRT
<213> ORGANISM: Artificial Sequence
<220> FEATURE:
<223> OTHER INFORMATION: fusion protein

<400> SEQUENCE: 197

```
Met Glu Ile Tyr Glu Asn Glu Asn Asp Gln Val Glu Ala Val Lys Arg
1               5                   10                  15

Phe Phe Ala Glu Asn Gly Lys Ala Leu Ala Val Gly Val Ile Leu Gly
                20                  25                  30

Val Gly Ala Leu Ile Gly Trp Arg Tyr Trp Asn Ser His Gln Val Asp
            35                  40                  45

Ser Ala Arg Ser Ala Ser Leu Ala Tyr Gln Asn Ala Val Thr Ala Val
50                  55                  60

Ser Glu Gly Lys Pro Asp Ser Ile Pro Ala Ala Glu Lys Phe Ala Ala
65                  70                  75                  80

Glu Asn Lys Asn Thr Tyr Gly Ala Leu Ala Ser Leu Glu Leu Ala Gln
                85                  90                  95

Gln Phe Val Asp Lys Asn Glu Leu Glu Lys Ala Ala Gln Leu Gln
                100                 105                 110
```

```
Gln Gly Leu Ala Asp Thr Ser Asp Glu Asn Leu Lys Ala Val Ile Asn
            115                 120                 125

Leu Arg Leu Ala Arg Val Gln Val Gln Leu Lys Gln Ala Asp Ala Ala
        130                 135                 140

Leu Lys Thr Leu Asp Thr Ile Lys Gly Glu Gly Trp Ala Ala Ile Val
145                 150                 155                 160

Ala Asp Leu Arg Gly Glu Ala Leu Leu Ser Lys Gly Asp Lys Gln Gly
                165                 170                 175

Ala Arg Ser Ala Trp Glu Ala Gly Val Lys Ser Asp Val Thr Pro Ala
            180                 185                 190

Leu Ser Glu Met Met Gln Met Lys Ile Asn Asn Leu Ser Ile Gly Ser
        195                 200                 205

Met Ser Gly Arg Leu Glu Glu Glu Leu Arg Arg Arg Leu Ser
210                 215                 220

<210> SEQ ID NO 198
<211> LENGTH: 206
<212> TYPE: PRT
<213> ORGANISM: Artificial Sequence
<220> FEATURE:
<223> OTHER INFORMATION: YfgM

<400> SEQUENCE: 198

Met Glu Ile Tyr Glu Asn Glu Asn Asp Gln Val Glu Ala Val Lys Arg
1               5                   10                  15

Phe Phe Ala Glu Asn Gly Lys Ala Leu Ala Val Gly Val Ile Leu Gly
            20                  25                  30

Val Gly Ala Leu Ile Gly Trp Arg Tyr Trp Asn Ser His Gln Val Asp
        35                  40                  45

Ser Ala Arg Ser Ala Ser Leu Ala Tyr Gln Asn Ala Val Thr Ala Val
    50                  55                  60

Ser Glu Gly Lys Pro Asp Ser Ile Pro Ala Ala Glu Lys Phe Ala Ala
65                  70                  75                  80

Glu Asn Lys Asn Thr Tyr Gly Ala Leu Ala Ser Leu Glu Leu Ala Gln
                85                  90                  95

Gln Phe Val Asp Lys Asn Glu Leu Glu Lys Ala Ala Ala Gln Leu Gln
            100                 105                 110

Gln Gly Leu Ala Asp Thr Ser Asp Glu Asn Leu Lys Ala Val Ile Asn
        115                 120                 125

Leu Arg Leu Ala Arg Val Gln Val Gln Leu Lys Gln Ala Asp Ala Ala
    130                 135                 140

Leu Lys Thr Leu Asp Thr Ile Lys Gly Glu Gly Trp Ala Ala Ile Val
145                 150                 155                 160

Ala Asp Leu Arg Gly Glu Ala Leu Leu Ser Lys Gly Asp Lys Gln Gly
                165                 170                 175

Ala Arg Ser Ala Trp Glu Ala Gly Val Lys Ser Asp Val Thr Pro Ala
            180                 185                 190

Leu Ser Glu Met Met Gln Met Lys Ile Asn Asn Leu Ser Ile
        195                 200                 205

<210> SEQ ID NO 199
<211> LENGTH: 260
<212> TYPE: PRT
```

```
<213> ORGANISM: Artificial Sequence
<220> FEATURE:
<223> OTHER INFORMATION: fusion protein

<400> SEQUENCE: 199

Met Ser Lys His His His His Ser Asn His His Arg His Asn His His
1               5                   10                  15

His His Ser Gly Asn His His Ser Gly Ser Ala Ala Gly Gly Glu
            20                  25                  30

Glu Asp Lys Lys Pro Ala Gly Gly Glu Gly Gly Gly Ala His Ile Asn
            35                  40                  45

Leu Lys Val Lys Gly Gln Asp Gly Asn Glu Val Phe Phe Arg Ile Lys
50                      55                      60

Arg Ser Thr Gln Leu Lys Lys Leu Met Asn Ala Tyr Cys Asp Arg Gln
65                  70                      75                  80

Ser Val Asp Met Thr Ala Ile Ala Phe Leu Phe Asp Gly Arg Arg Leu
                85                      90                      95

Arg Ala Glu Gln Thr Pro Asp Glu Leu Glu Met Glu Asp Gly Asp Glu
                100                     105                     110

Ile Asp Ala Met Leu His Gln Thr Gly Gly Ala Cys Ala Trp Ser His
            115                     120                     125

Pro Gln Phe Glu Lys Gly Gly Gly Ser Gly Gly Ser Ser Gly Gly Ser
130                     135                     140

Ala Trp Ser His Pro Gln Phe Glu Lys Gly Ser Gly Ser Ala Glu Ser
145                     150                     155                     160

Glu Ala Ala Ser Ser Thr Met Ile Lys Val Lys Thr Leu Thr Gly Lys
                165                     170                     175

Glu Ile Glu Ile Asp Ile Glu Pro Thr Asp Thr Ile Asp Arg Ile Lys
            180                     185                     190

Glu Arg Val Glu Glu Lys Glu Gly Ile Pro Pro Val Gln Gln Arg Leu
        195                     200                     205

Ile Tyr Ala Gly Lys Gln Leu Ala Asp Asp Lys Thr Ala Lys Asp Tyr
        210                     215                     220

Asn Ile Glu Gly Gly Ser Val Leu His Leu Val Leu Ala Leu Arg Gly
225                     230                     235                     240

Gly Ala Thr Gly Thr Ala Ser Thr Arg Leu Glu Glu Glu Leu Arg Arg
                245                     250                     255

Arg Leu Ala Ser
            260
```

EPITOPE TAGS RECOGNIZED BY SPECIFIC BINDERS

FIELD OF THE INVENTION

The present invention provides peptides useful as epitope tags, which may be fused to a polypeptide of interest, as well as antibodies that specifically bind to these peptides. The peptides and/or antibodies can be used for detecting, immobilizing, isolating or purifying a molecule that is conjugated to such a peptide and/or antibody.

BACKGROUND

Epitope tags play an important role in virtually every aspect of life sciences. They are, e.g., used in biotechnological applications in order to facilitate expression and purification of recombinant proteins (Waugh, D. S. Making the most of affinity tags. *Trends Biotechnol* 23, 316-320 (2005)). In cell biology, epitope tags are often used to monitor the biogenesis or topology of a given protein of interest (POI) (Nooh, M. M. & Bahouth, S. W. Visualization and quantification of GPCR trafficking in mammalian cells by confocal microscopy. *Methods Cell Biol.* 142, 67-78 (2017); Kocaoglu, 0. & Carlson, E. E. Progress and prospects for small-molecule probes of bacterial imaging. *Nat Chem Biol* 12, 472-478 (2016)). Tags have also been instrumental in immuno-precipitation of protein complexes to be studied with mass spectrometry techniques (Shi, Y. et al. A strategy for dissecting the architectures of native macromolecular assemblies. *Nat Methods* 12, 1135-1138 (2015); Smits, A. H. & Vermeulen, M. Characterizing Protein-Protein Interactions Using Mass Spectrometry: Challenges and Opportunities. *Trends Biotechnol* 34, 825-834 (2016). Over the years, at least a dozen of different tags evolved providing researchers with multiple tools for most scientific scenarios (Waugh, D. S. Making the most of affinity tags. *Trends Biotechnol* 23, 316-320 (2005); Brizzard, B. Epitope tagging. *BioTechniques* 44, 693-695 (2008)). A given tag might, however, perform extraordinarily well in a specific application while failing completely in others. As a result, most researchers rely on a variety of tags to cover the range of required applications.

It seems that a truly universal tag does not exist so far. One explanation could be the fact that most tags were found as byproducts while screening for binders (typically monoclonal antibodies) against naturally occurring proteins. This is, for example, true for the c-myc-tag (Evan, G. I., Lewis, G. K., Ramsay, G. & Bishop, J. M. Isolation of monoclonal antibodies specific for human c-myc proto-oncogene product. *Mol Cell Biol* 5, 3610-3616 (1985)), the HA-tag (Field, J. et al. Purification of a RAS-responsive adenylyl cyclase complex from *Saccharomyces cerevisiae* by use of an epitope addition method. *Mol Cell Biol* 8, 2159-2165 (1988)) or the Spot-Tag® (Virant, D. et al. A peptide tag-specific nanobody enables high-quality labeling for dSTORM imaging. *Nat Commun* 1-14 (2018). doi:10.1038/s41467-018-03191-2, Braun, M. B. et al. Peptides in headlock a novel high-affinity and versatile peptide-binding nanobody for proteomics and microscopy. *Sci Rep* 6, 19211 (2016)). Typically, the tag is thus by default the minimal peptide that is efficiently recognized by the respective binder. As a consequence, the properties of such tags are predominantly defined by chance depending on the selected binder and they generally cannot be re-adjusted to the specific experimental needs or conditions. Alternatively, some tags have also been rationally designed for one specific application. For instance, the His-tag is ideally suited for a crude initial purification of recombinantly expressed proteins on metal ion chelate resins, which was the purpose it was developed for (Hochuli, E., Döbeli, H. & Schacher, A. New metal chelate adsorbent selective for proteins and peptides containing neighbouring histidine residues. *J. Chromatogr.* 411, 177-184 (1987)). However, due to the lack of high-affinity binders, the His-tag has so far not been used extensively for microscopic applications in cell biology.

It is object of the invention to provide improved epitope tags and specific binding molecules thereto.

SUMMARY OF THE INVENTION

The present invention relates to fusion protein comprising: (a) a peptide comprising the sequence of X1-X2-X3-X4-X5-X6-X7-X8-X9-R-L-X12-X13 (SEQ ID NO: 01), wherein X1 is G or S or T or P, X2 is R or G or A or E or P, X3 is L or V, X4 is E or Q, X5 is E or Q, X6 is E or Q, X7 is L or I or V, X8 is R or A or Qor E, X9 is R or A or Q or E, X12 is S or T or D or E or P or A or no amino acid, and wherein X13 is E or K or P or S or A or D or no amino acid; and (b) a polypeptide.

The present invention also relates to an antibody that specifically binds to the peptide comprised in the fusion protein of the invention.

The present invention also relates to a fusion protein comprising a peptide that the antibody of the invention binds to.

The present invention also relates to a complex comprising a fusion protein of the invention and an antibody of the invention.

The present invention also relates to a nucleic acid encoding a fusion protein of the invention or an antibody of the invention.

The present invention also relates to a vector comprising the nucleic acid of the invention.

The present invention also relates to a host cell comprising a nucleic acid of the invention or a vector of the invention or expressing a fusion protein of the invention or the antibody of the invention.

The present invention also relates to a use of an antibody of the invention for the detection, immobilization, isolation, or purification of a fusion protein of the invention.

The present invention also relates to a method of detecting a fusion protein of the invention, comprising contacting the fusion protein with an antibody of the invention.

The present invention also relates to a method of isolating the fusion protein of the invention, comprising contacting the fusion protein with an antibody of the invention.

Where the fusion protein of the invention comprises an antibody moiety, the present invention also relates to a method of isolation of a specific target of the antibody moiety.

The present invention also relates to a kit comprising a nucleic acid or a nucleic acid expression construct encoding a peptide as comprised in a fusion protein of the invention and optionally an antibody of the invention.

A, Sketch of proteins used for ALFA binding assays. In this figure, the ALFA tag used in shGFP2 fusions can either be ALFA$^{ST}$ (SEQ ID NOs: 05-07) or ALFA$^{PE}$ (SEQ ID NO: 33). B, 20 µl ALFA Selector$^{ST}$ resin presenting NbALFA$^{ST}$ (SEQ ID NO: 133) was saturated with a GFP variant (shGFP2, Frey and Görlich; Cell. 2018 Jun. 28; 174(1):202-217.e9. doi: 10.1016/j.cell.2018.05.045) fused to ALFA$^{ST}$ or ALFA$^{PE}$ at different locations (internal (left); N-terminus (middle) or C-terminus (right)). After washing 4 times with PBS, the beads were suspended in a 10-fold excess of PBS containing 200 µM ALFA$^{ST}$ peptide (Ac-PSR-LEEELRRRLTEP-Amide, SEQ ID NO: 179) and gently mixed at room temperature. At indicated time points, specific elution from the beads was quantified using the GFP fluorescence released into the supernatant. Shown are mean fluorescence values from three independent experiments performed in parallel and standard deviations for each time point. Efficient peptide elution of ALFA$^{PE}$ fusions is observed already after 20-30 min at room temperature. In contrast, all GFP variants fused to ALFA$^{ST}$ remained tightly bound to the resin. Note that the elution kinetics is largely independent of the localization of the respective ALFA tag variant within the fusion protein. C, 10 µl of ALFA Selector$^{ST}$ resin saturated with either ALFA$^{ST}$-shGFP2 (top row) or ALFA$^{PE}$-shGFP2 (bottom row) were transferred into 8-well PCR strips. After removing remaining liquid, the beads were incubated with 10 µl of the indicated substances for 60 min at room temperature. Photos were taken after sedimentation of the beads. Asterisks (*) indicate conditions known to lead to a partial or complete loss of GFP fluorescence.

Figure 2D:
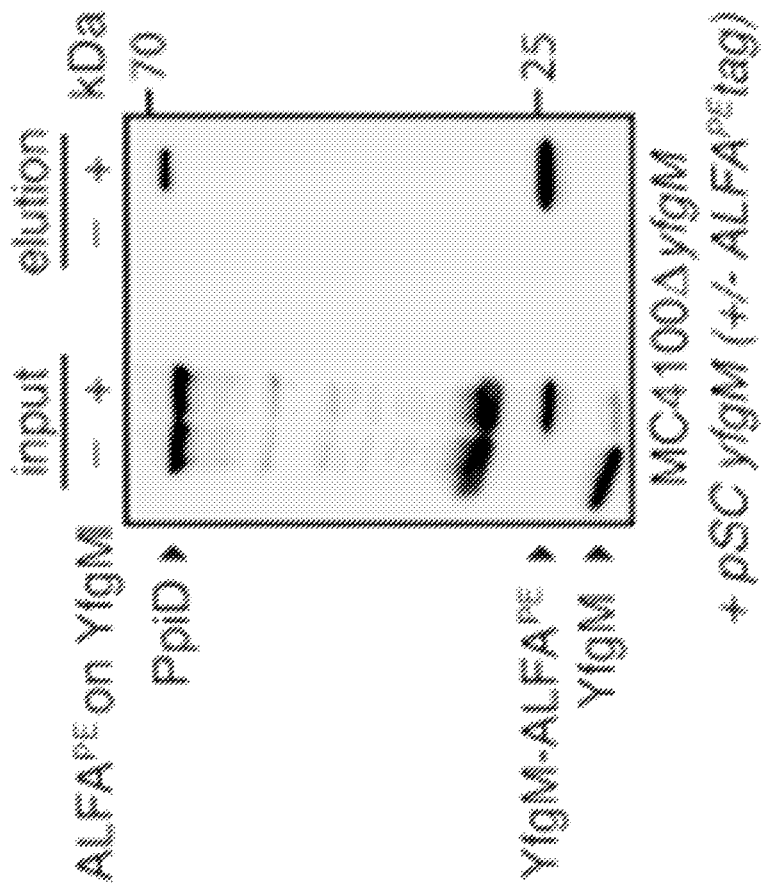
Figure 2D:
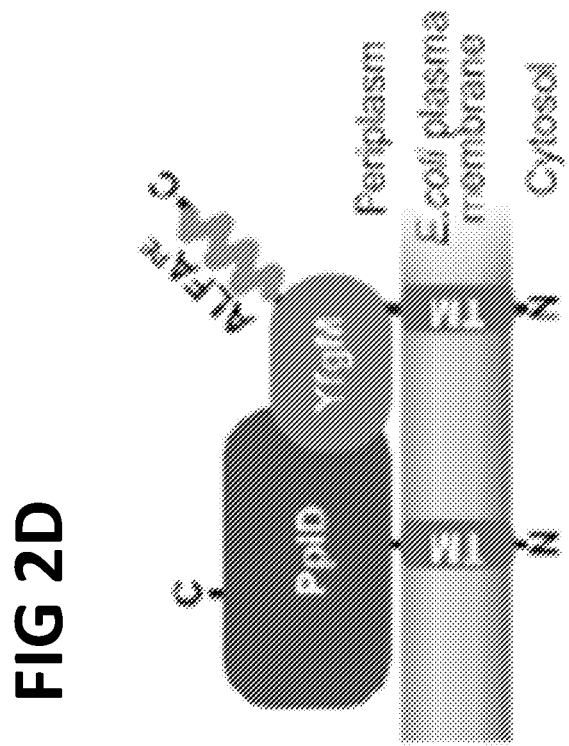

FIG. 2 Pull-down of ALFA-tagged target proteins and protein complexes from complex lysates using ALFA Selector$^{ST}$.

A, shGFP2 N-terminally fused to ALFA$^{ST}$ (SEQ ID NO: 07; ALFA$^{ST}$-sfGFP2, left) or ALFA$^{PE}$ (SEQ ID NO: 33; ALFA$^{PE}$-GFP, right). Proteins were over-expressed in E. coli and purified by Nickel-affinity chromatography via their C-terminal His$_6$-tag followed by gel filtration on a Superdex 75 size exclusion column. B+C, To obtain defined input material for one-step affinity purifications using the ALFA Selector$^{ST}$, E. coli (B) or HeLa (C) mock extracts were blended with 3 µM of the respective substrate. Mock lysate served as a specificity control. 1 mL of each lysate/substrate mixture was incubated with 25 µl of ALFA-Selector$^{ST}$ comprising the NbALFA$^{ST}$ (SEQ ID NO: 133) for 1 h at 4° C. After washing 4 times with 1 mL of PBS, bound proteins were eluted two times for 10 min with 25 µl of 200 µM of ALFA$^{ST}$ peptide (SEQ ID NO: 179) in PBS at room temperature. Proteins remaining on the beads were afterwards eluted with SDS sample buffer. 0.5 µL (B) or 1.5 µL (C) of input and non-bound fractions were analyzed by SDS-PAGE (12%) and Coomassie staining. Shown eluate fractions correspond to the material eluted from 1 µl of ALFA Selector$^{ST}$ resin. Note that protein tagged with either ALFA$^{ST}$ tag or ALFA$^{PE}$ tag can be specifically pulled down under native conditions using ALFA Selector$^{ST}$. Highly efficient and specific elution of proteins fused to the ALFA$^{PE}$ tag can be accomplished under native conditions by competition with free ALFA$^{ST}$ peptide. Further note that the proteins purified from either lysate using the ALFA Selector$^{ST}$ resin contain significantly less impurities than the respective substrate proteins purified by conventional two-step chromatography.

D, Left: Sketch of the YfgM-PpiD complex. Right: Non-tagged (-) (SEQ ID NO: 198) or C-terminally ALFA$^{PE}$ tagged YfgM (+) (SEQ ID NO: 197) was expressed in a yfgM deletion stain. Membrane protein complexes were solubilized using 1% DDM from total lysate. YfgM-ALFA$^{PE}$-containing complexes were purified in a single step using the ALFA Selector$^{ST}$ affinity resin comprising the nanobody of SEQ ID NO: 133. A serum raised against the YfgM-PpiD complex recognized both, PpiD and YfgM, in the input fractions. ALFA Selector$^{ST}$ specifically immunoprecipitated the native protein complex of YfgM-ALFA$^{PE}$ and its interaction partner PpiD.

FIG. 3: Nanobody-based detection of ALFA$^{ST}$-tagged proteins in immunofluorescence applications A: Sketch of NbALFA$^{ST}$ bound to ALFA$^{ST}$ tags (left) or ALFA$^{PE}$ tags (right). Given are ALFA tag sequences used for tagging at various positions (N-terminal ALFA$^{ST}$ tag: SEQ ID NO: 05, internal ALFA$^{ST}$ tag: SEQ ID NO: 06, C-terminal ALFA$^{ST}$ tag: SEQ ID NO: 07)

B: Sequence of NbALFA$^{ST}$ (NbALFA clone 1G5; SEQ ID NO: 133). Grey boxes indicate CDRs 1-3 (AbM definition, SEQ ID NOs: 115-117).

C: COS-7 cells transfected with Tom70-EGFP-ALFA$^{ST}$ (upper row) or Tom70-EGFP-ALFA$^{PE}$ (lower row) were fixed with 4% paraformaldehyde. Staining with NbALFA$^{ST}$ coupled to AbberiorStar635P (FluoTag-X2 anti-ALFA AbberiorStar635P) was performed after permeabilization. First column: FluoTag-X2 anti-ALFA; second column: target detection using the intrinsic EGFP fluorescence; third column: overlay incl. DAPI stain; fourth column: Sketch of target proteins detected by fluorescently labeled NbALFA$^{ST}$ All scale bars: 20 µm.

D: N-terminally ALFA$^{ST}$-tagged Vimentin (upper row) or ALFA$^{PE}$_tagged Vimentin (lower row) was detected with FluoTag-X2 anti-ALFA AbberiorStar635P after fixation with 4% paraformaldehyde (PFA), 2% glutaraldehyde (GA), or 100% Methanol (MeOH). Right column: Sketch of ALFA-tagged vimentins detected by fluorescently labeled NbALFA$^{ST}$.

E: Intrabody-based detection of ALFA$^{ST}$-tagged proteins. COS-7 cells were co-transfected with an NbALFA$^{ST}$-mScarlet-I fusion and ALFA$^{ST}$_tagged target proteins. Target proteins were detected via EGFP fluorescence (for TOM70-EGFP-ALFA$^{ST}$) or immunofluorescence using FluoTag anti-ALFA AbberiorStar635P (for ALFA$^{ST}$-FLAG-Vimentin). In parallel, NbALFA$^{ST}$-mScarlet-I was detected by the red mScarlet-I fluorescence. Note the excellent co-localization between the target protein (left column) and the mScarlet-I signal (middle column).

Figures 4A, 4B:
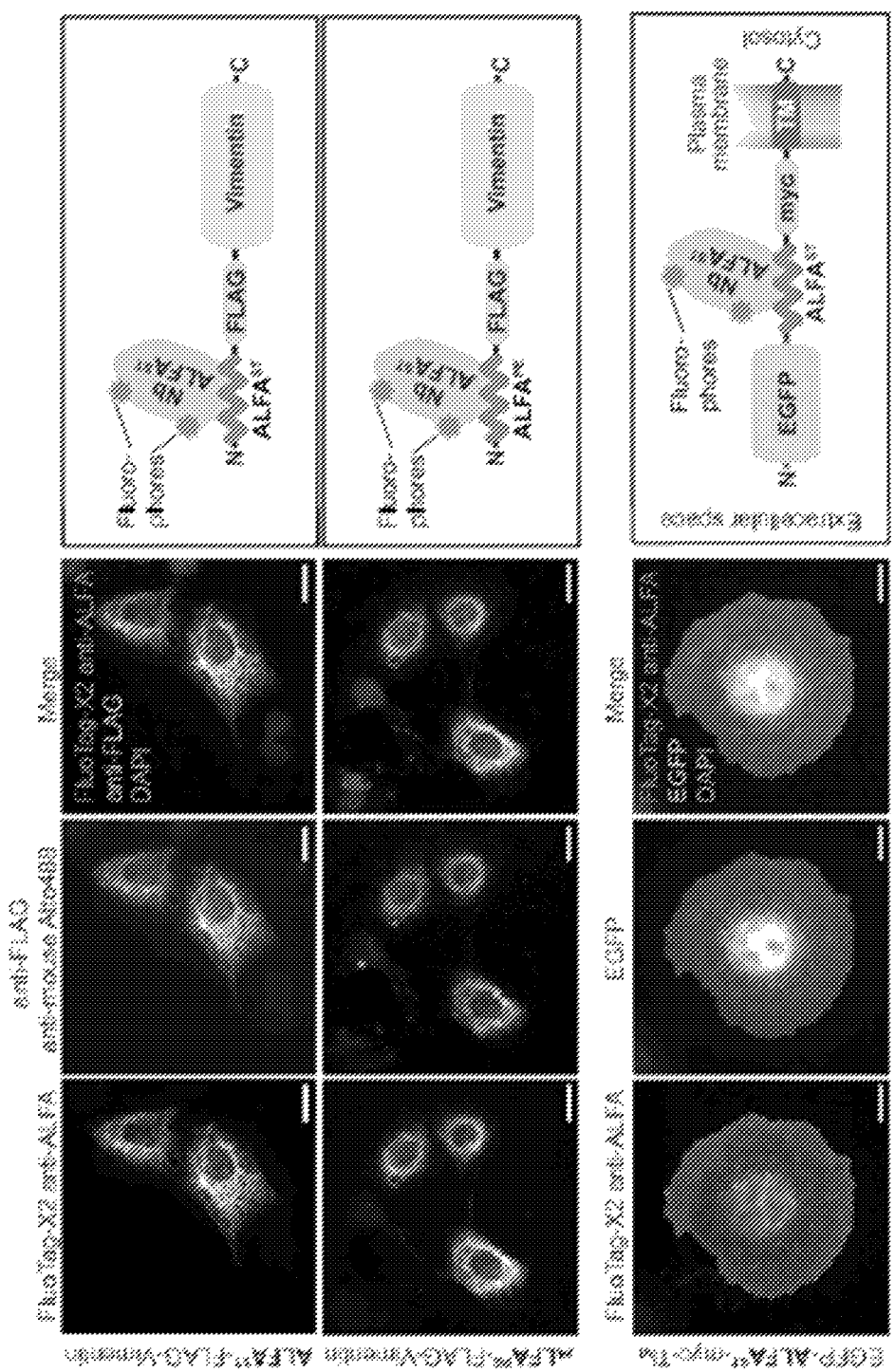

FIG. 4: ALFA-tagged proteins can be detected by fluorescently labeled NbALFA$^{ST}$ regardless of its localization within the fusion protein COS-7 cells were transfected with constructs encoding proteins fused to an ALFA tag at their N-termini (ALFA$^{ST}$-FLAG-Vimentin or ALFA$^{PE}$-FLAG-Vimentin; A), or within individual protein-domains (EGFP-ALFA$^{ST}$-myc-TM; B). Cells were fixed with 4% PFA and stained as indicated. For A and B, cells were permeabilized with 0.1% TritonX-100; for C, cells were stained under non-permeabilizing conditions. TM: transmembrane domain. Sketches illustrate the topology of substrates and detection by fluorescently labeled NbALFA$^{ST}$ (FluoTag-X2 anti-ALFA).

Figure 5:
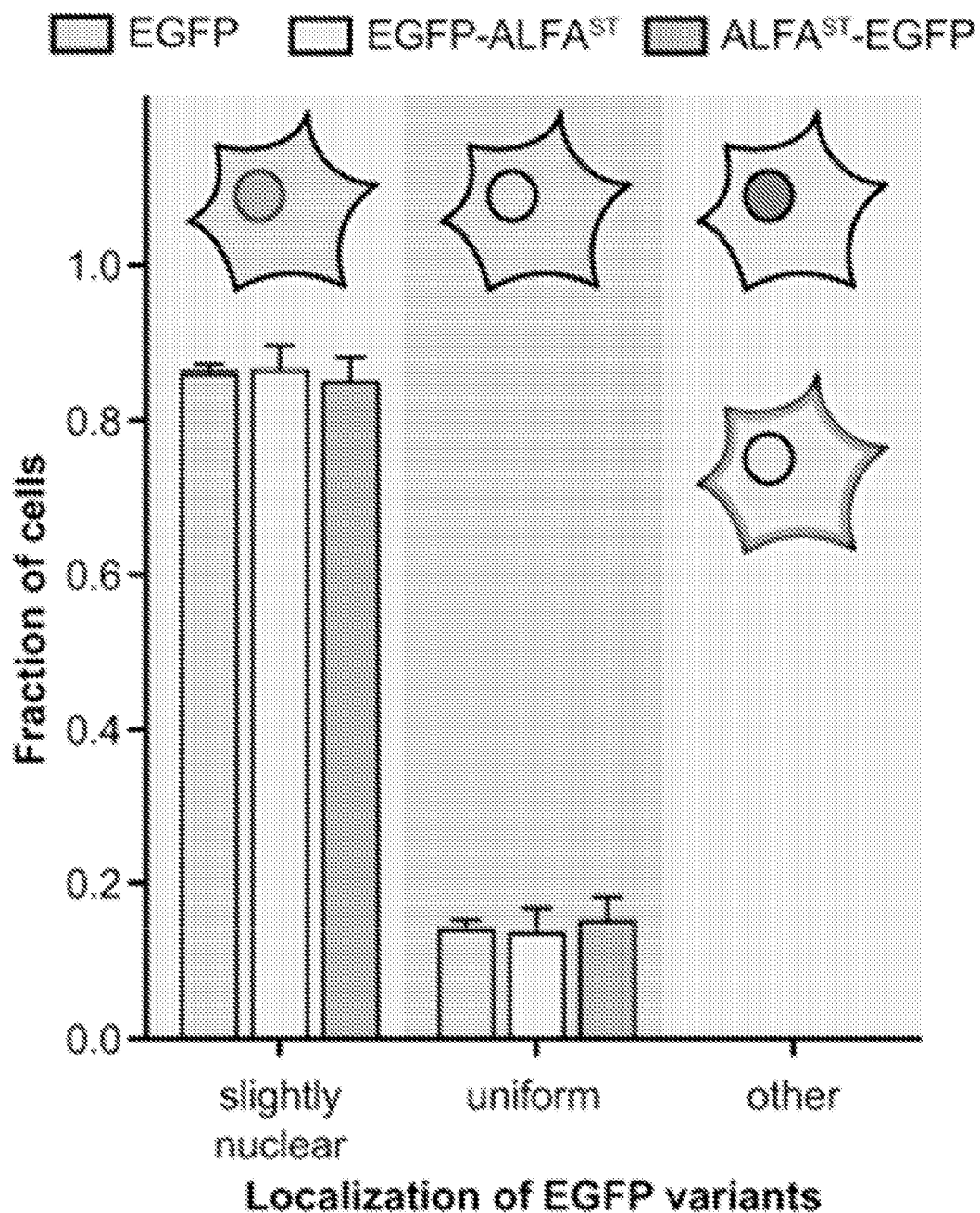

FIG. 5: GFP fused to N- or C-terminal ALFA$^{ST}$ tags show normal intracellular localization 3T3 cells were transiently transfected with EGFP fusions harboring N- or C-terminal ALFA$^{ST}$ tags. Non-tagged EGFP from pEGFP-N1 served as a control. The localization of the respective EGFP variants was analyzed on 6-7 individual images for each construct. Together 120-130 cells were imaged per construct and the localization of EGFP was analyzed. In general, each EGFP construct displayed a distribution across the cytosol and the nucleus. Cells were distributed into three groups ("slightly nuclear", "uniform" and "other") according to the observed nucleocytoplasmic localization of EGFP. Standard deviations were deduced from values obtained from individual images. Differences between the localizations of tagged and non-tagged EGFP variants were statistically insignificant (Student's t-test).

FIG. 6: Western-blot and dot-blot detection of ALFA-tagged target proteins using fluorescently labeled NbAL-FA$^{ST}$ (FluoTag-X2 anti-ALFA)

A, COS-7 cells transfected with ALFA$^{ST}$-FLAG-Vimentin or ALFA$^{PE}$-FLAG-Vimentin were lysed in SDS buffer. Cells transfected with an irrelevant plasmid served as a control. Lysates corresponding to the same number of cells were analyzed by SDS-PAGE and Western-Blot. The vimentin fusion proteins were visualized with NbALFA$^{ST}$ coupled to IRDye800 (FluoTag-X2 anti-ALFA IRDye800). Tubulin served as a loading control and was detected by a mouse anti-Tubulin followed by a FluoTag-X2 anti-Mouse coupled to IRDye680. Complete lanes are shown in FIG. 7A.

B, Sketch of recombinant *E. coli* maltose-binding protein (MBP) harboring multiple epitope tags (FLAG, HA, myc and ALFA$^{ST}$) used for experiment shown in C and D.

C, Dilution series of the protein sketched in B were spotted onto nitrocellulose membranes. Established monoclonal antibodies (anti-FLAG M2—Sigma #F1804, anti-myc 9E10—SynapticSystems #343 011, anti-HA F-7—SantaCruz #sc-7392) were used in combination with a secondary anti-mouse IgG IRDye800CW (Li-Cor #925-32210, dilution 1:1000) to detect FLAG, myc and HA-tag, respectively. The ALFA$^{ST}$ tag was detected using a FluoTag-X2 anti-ALFA directly coupled to IRDye800CW. The nanobody and all primary antibodies were used at 2.7 nM final concentration, which is well within the range recommended by the suppliers. The complete experiment including internal controls is shown in FIG. 7B.

D, Quantification of signals obtained in C, displayed in a double logarithmic plot. Lines represent linear fits to the obtained values. Even without signal amplification by a secondary antibody, signals obtained by NbAL-FA$^{ST}$ were 3- to >10-times stronger than by established reagents recognizing epitope tags. At the same time, detection with NbALFA$^{ST}$ was 10-fold more sensitive and showed an excellent linearity over ~3 orders of magnitude.

FIG. 7: Highly sensitive Western-blot and dot-blot detection of ALFA-tagged target proteins using fluorescently labeled NbALFA$^{ST}$ (FluoTag-X2 anti-ALFA)

Figure 6A:
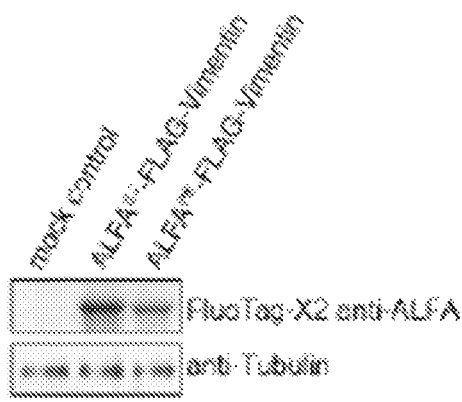

A, Same experiment as shown in FIG. 6A. Here, however, complete lanes are shown. Note that in the absence of any vector encoding an ALFA$^{ST}$ tagged protein, only very minor bands (*) can be detected using fluorescently labeled NbALFA (FluoTag-X2 anti-ALFA).

Figure 6B:
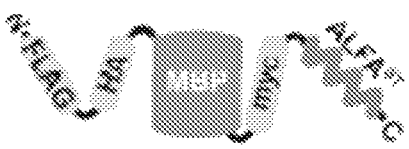
Figure 6C:
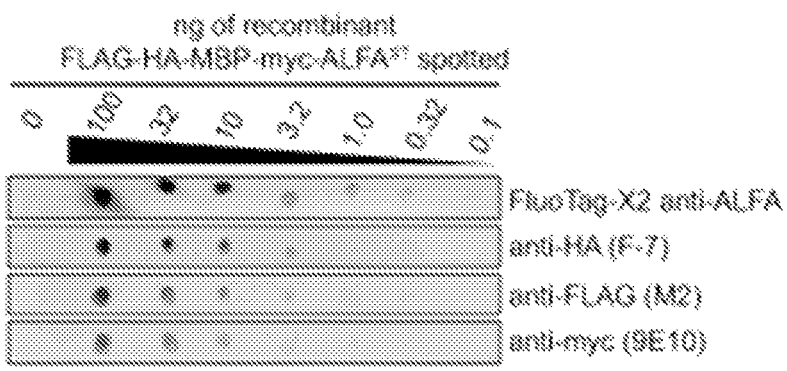
Figure 6D:
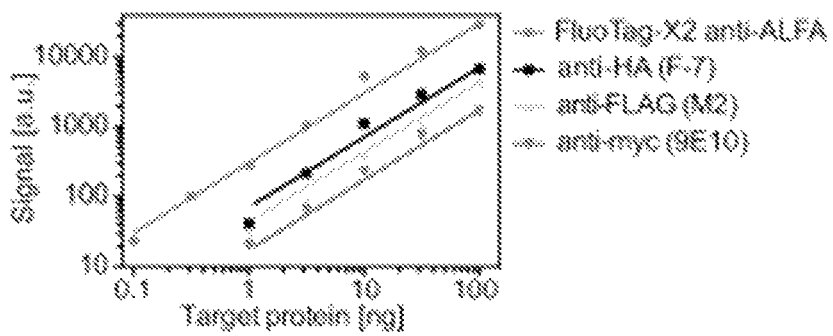

B, Same experiment as shown in FIG. 6C. In addition to the data presented in FIG. 6C, detection of MBP by a combination of rabbit polyclonal serum recognizing MBP (SynapticSystems) and an anti-rabbit IgG IRDye680RD (Li-Cor #925-68071) is shown as an internal loading control. Overlays show MBP signals in red and signals corresponding to epitope tags in green.

FIG. 8: Interaction of ALFA$^{ST}$-tagged proteins with ALFA Selector$^{ST}$ and ALFA Selector$^{PE}$ resins.

A; Sketch of ALFA Selector resins bound to shGFP2-ALFA$^{ST}$. In this sketch, the ALFA Selector resin could be ALFA Selector$^{ST}$ or ALFA Selector$^{PE}$.

B and C; Peptide elution from NbALFA-coupled affinity resins. Agarose-based resins coupled to NbALFA$^{ST}$ (SEQ ID NO: 133; ALFA Selector$^{ST}$, left) or an NbAL-FA$^{PE}$ mutant (SEQ ID NO: 134; ALFA Selector$^{PE}$, right) were charged with shGFP2 harboring a C-terminal ALFA$^{ST}$ tag. To estimate off-rates, the resins were suspended PBS containing an excess of free ALFA$^{ST}$ peptide and incubated at 25° C. Control reactions were carried out without peptide. At indicated time points, shGFP2 released from the resin was quantified. B shows mean fluorescence readings of three experiments as well as standard deviations for each time point. Lines represent fits to a single exponential. Efficient peptide elution of shGFP2-ALFA$^{ST}$ from ALFA Selector$^E$ was observed already after 15-20 min at room temperature. In contrast, peptide elution from ALFA Selector$^{ST}$ was inefficient even after prolonged incubation. In the absence of free ALFA$^{ST}$ peptide during elution, the ALFA$^{ST}$-tagged target protein remained tightly bound to both resins. A photo was taken upon UV illumination after 3 h of elution (C).

D; Resistance towards stringent washing steps. ALFA Selector variants described in B were charged with either ALFA$^{ST}$-shGFP2 or shGFP2-ALFA$^{ST}$ and incubated with a 10-fold volume of the indicated substances for 1 h at 25° C. with shaking. Without further washing steps, photos were taken upon UV illumination after sedimentation of the beads.

E; Resistance towards non-physiological pH. Similar to D. Here, however, the resin was washed to remove non-bound material after incubating at indicated pH for 30 min. Photos were taken after re-equilibration in PBS to allow for recovery of the GFP fluorescence.

FIG. 9: Pull-down of ALFA$^{ST}$-tagged target proteins and protein complexes from complex lysates using ALFA Selector$^{ST}$ and ALFA Selector$^{PE}$.

A; Input protein used for experiments described in (B and C).

B and C; One-step affinity purifications using the ALFA Selector Resins. *E. coli* (A) or HeLa (B) lysates blended with 3 µM purified ALFA$^{ST}$-tagged shGFP2 (A) were incubated with ALFA Selector$^{ST}$, ALFA Selector$^{PE}$ or an analogous resin without immobilized sdAb (Selector Control). After washing with PBS, the resins were incubated with 200 µM ALFA$^{ST}$ peptide for 20 min. Proteins remaining on the beads were eluted with SDS sample buffer. Indicated fractions were analyzed by SDS-PAGE and Coomassie staining. Shown eluate fractions correspond to the material eluted from 1 µl of resin.

D; Pull-down of a native *E. coli* YfgM-PpiD inner membrane protein complex using the ALFA Selector$^{PE}$. Left: Sketch of the YfgM-PpiD membrane protein complex. Right: A yfgM deletion strain was complemented with either C-terminally ALFA$^{ST}$_tagged (left panel) or untagged YfgM (right panel; control reaction) expressed from a low-copy vector. Membrane protein complexes were solubilized from total lysate using DDM. Complexes containing YfgM-ALFA$^{ST}$ were purified in a single step using ALFA Selector$^{PE}$ affinity resin and eluted under native conditions using 200 µM ALFA$^{ST}$ peptide. Samples corresponding to 1/800 of the input and non-bound material or 1/80 of eluate fractions were resolved by SDS page and analyzed by Western-blot. A rabbit serum raised against the YfgM-PpiD complex (Götzke et al., YfgM is an ancillary subunit of the SecYEG translocon in *Escherichia coli*. *J Biol Chem* 289, 19089-19097 (2014)) recognized both, PpiD and YfgM, in the input fractions. ALFA Selector$^{PE}$ specifically immunoprecipitated the native protein complex comprising ALFA$^{ST}$-tagged YfgM and its interaction partner PpiD. In the control reaction (no ALFA$^{ST}$ tag on YfgM), both proteins were absent in the eluate.

FIG. 10: Peptide elution of ALFA$^{ST}$-tagged GFPs from ALFA Selector resins.

Figures 10A, 10B, 10C:
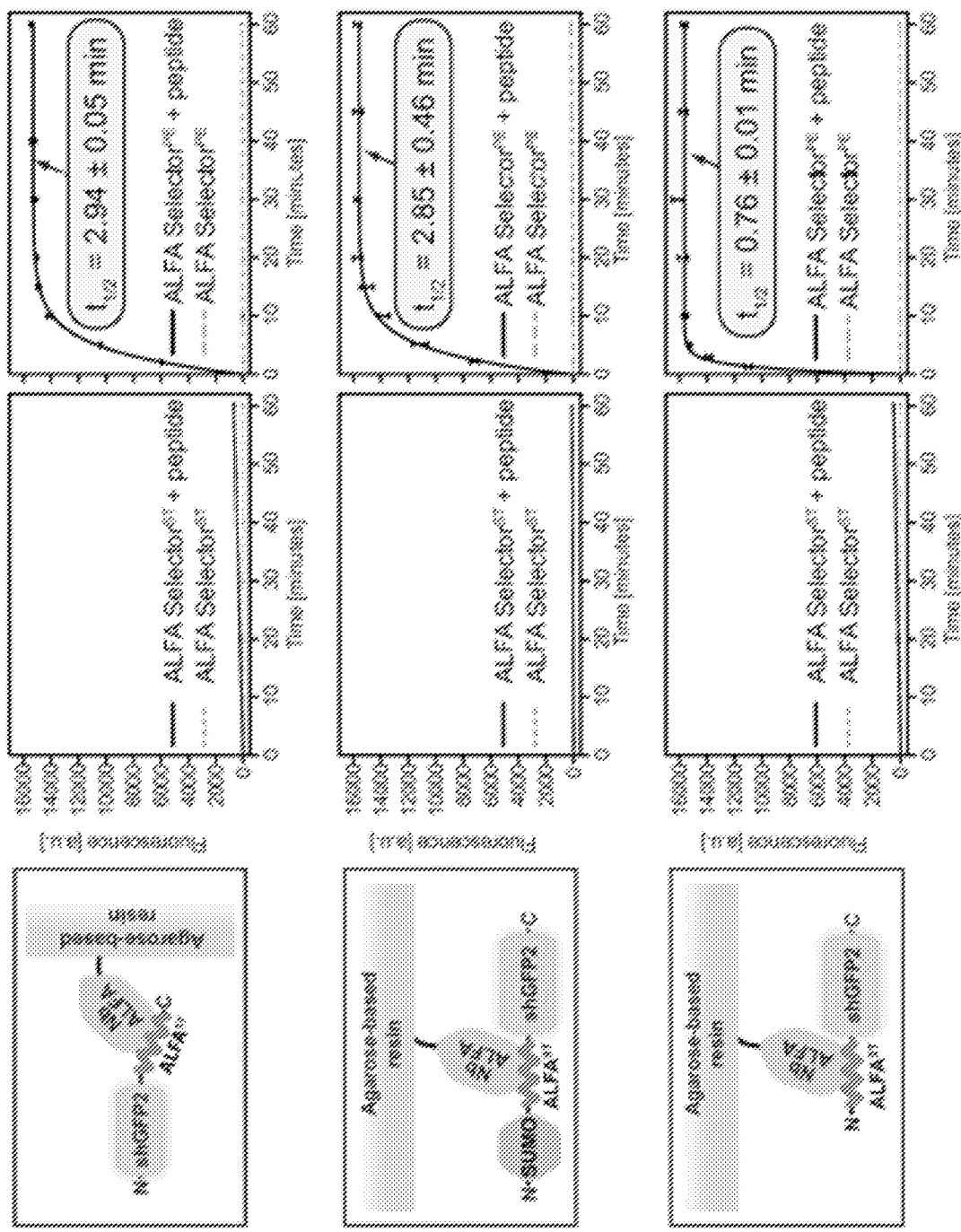

20 µl ALFA Selector$^{ST}$ (presenting NbALFA$^{ST}$, SEQ ID NO: 133) or ALFA Selector$^{PE}$ (presenting NbALFA$^{PE}$, SEQ ID NO: 134) were charged with shGFP2-ALFA$^{ST}$ (A), bdSUMO-ALFA$^{ST}$-shGFP2 (B) or ALFA$^{ST}$-shGFP2 (C). After washing with PBS, the beads were suspended in a 10-fold excess of PBS containing 200 µM free ALFA$^{ST}$ peptide and gently mixed at 25° C. Control reactions were carried out without peptide. At indicated time points, specific elution from the beads was quantified using the GFP fluorescence released into the supernatant. Shown are mean fluorescence readings of three experiments as well as standard deviations for each time point. Lines represent fits to a single exponential. Half times are given for peptide elution from ALFA Selector$^{PE}$ only. For all substrate proteins, peptide elution from ALFA Selector$^{ST}$ was inefficient even after prolonged incubation. In the absence of ALFA$^{ST}$ peptide, the ALFA$^{ST}$_tagged target proteins remained tightly bound to both resins. FIG. 10A recapitulates data shown in FIG. 8B and is repeated here to allow for a direct comparison. Left panels: Sketch illustrating the experimental setup. The ALFA Selector resin could be ALFA Selector$^{ST}$ or ALFA Selector$^{PE}$; middle panels: Experiments performed with ALFA Selector$^{ST}$; right panel: Experiments performed with ALFA Selector$^{PE}$.

Figure 11D:
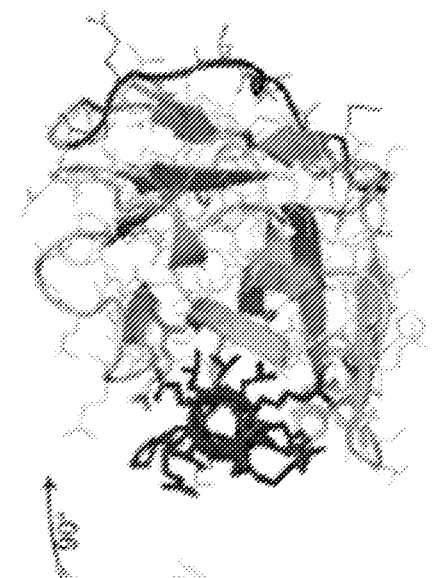
Figure 11D:
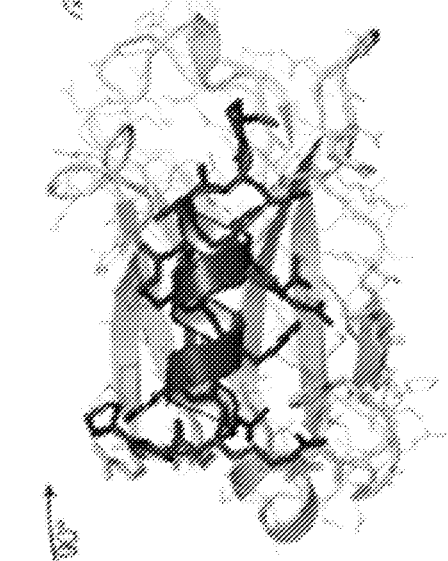
Figure 11D:
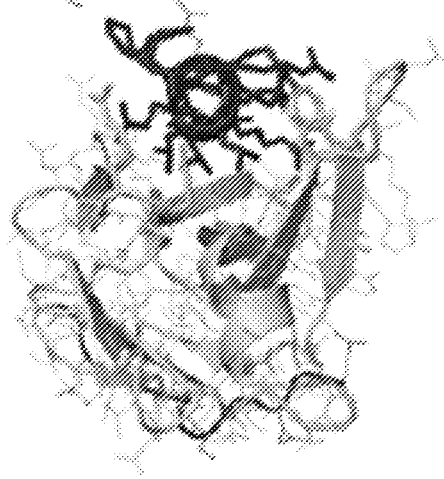

FIG. 11: X-ray structure of NbALFA$^{ST}$ bound to ALFA$^{ST}$ peptide

A-C; Views on the NbALFA$^{ST}$-ALFA$^{ST}$ peptide structure. A, view on the N-terminus of the ALFA$^{ST}$ peptide; B, side view on the ALFA$^{ST}$ peptide; C, view on the C-terminus of the ALFA$^{ST}$ peptide. NbALFA$^{ST}$ is illustrated in light grey with side chains represented as lines. Residues contacting the ALFA$^{ST}$ peptide are represented by sticks. The ALFA$^{ST}$ peptide is depicted in dark grey with side chains shown as sticks. The ALFA$^{ST}$ peptide was used with N-terminal acetylation and C-terminal amidation (SEQ ID NO: 179).

D; Sequence of NbALFA$^{ST}$ (SEQ ID NO: 133). As in FIG. 3B, boxes indicate CDRs 1-3 (SEQ ID NOs:115-117). Residues directly contacting the ALFA$^{ST}$ peptide are boxed. Residues in filled boxes were mutated to reduce the affinity for the ALFA$^{ST}$ peptide.

FIG. 12: Isolation of naïve lymphocytes using an ALFA-tagged nanobody recognizing CD62L.

Total human PBMCs were left untreated (before sorting) or isolated using an ALFA Selector$^{PE}$ resin loaded with an ALFA-tagged anti-human CD62L nanobody (after sorting). A sketch of the affinity purification strategy is shown in (a). Cells were stained with an anti-CD62L antibody and analyzed by flow cytometry (b). The same cells as in (b) were stained with antibodies directed against CD3, CD19 and CD62L, and analyzed by flow cytometry (c). A forward scatter/side scatter gate was set on lymphocytes in all analyses.

DETAILED DESCRIPTION

In order to overcome some of the shortcomings of the state of the art, the inventors of the present application created a small epitope tag recognized by a high-affinity nanobody. Such system may allow analysis of a protein's function in multiple aspects comprising but not limited to the analysis of its localization, analysis of its interaction partners by purification from lysates or in-vivo manipulations including induced protein mislocalization or depletion using a minimal set of recombinant constructs and cell lines without unintended interference with the protein of interest's physiological function.

In view of the limitations on the current epitope tags, the inventors of the present application decided to address the problem and find the features that an ideal epitope tag system should posses. A truly versatile tag should be small to minimize the potential side effect (Kocaoglu, 0. & Carlson, E. E. Progress and prospects for small-molecule probes of bacterial imaging. *Nat Chem Biol* 12, 472-478 (2016)). It is preferably monomeric in order to minimize artifactual oligomerization of the tagged proteins. It should also be electroneutral to avoid adding net charges to the tagged proteins; at the same time it should be soluble (Esposito, D. & Chatterjee, D. K. Enhancement of soluble protein expression through the use of fusion tags. *Curr. Opin. Biotechnol.* 17, 353-358 (2006)). An ideal tag should not affect the native structure, topology or localization of the tagged protein (Stadler, C. et al. Immunofluorescence and fluorescent-protein tagging show high correlation for protein localization in mammalian cells. *Nat Methods* 10, 315-323 (2013); Hoffmann, C. et al. A FlAsH-based FRET approach to determine G protein-coupled receptor activation in living cells. *Nat Methods* 2, 171-176 (2005)). In addition, the tag should be well expressed in eukaryotic and prokaryotic hosts and should be resistant towards proteolytic degradation. Ideally, it should be resistant to fixation and its sequence should be absent in common model organisms to avoid non-intended detection of endogenous host proteins.

Similar than for an ideal epitope tag, its corresponding binder should also have several characteristic to make the tag detection ideal. For example, the binder should be small in order to have easy access to crowded regions and provide the best binding affinity for the different applications. Current sophisticated applications (e.g. live in-vivo imaging) need a specific and genetically accessible probe with high affinity to the tag, which should be able to autonomously fold in vivo in various host organisms. For biochemical applications, however, the preferred binder should preferentially have intermediate affinity in order to allow for a competitive elution of the immuno-precipitated material under native conditions. When assessing commonly used epitope tags existing thus far, one applying the state of the art will ultimately need to sacrifice at least one of the mentioned features (see Table 1 below). To manufacture an epitope tag with ultimate versatility fulfilling all of the mentioned boundary conditions, the inventors of the present application have recognized

TABLE 1

Properties of common epitope tag systems

|  |  | FLAG-tag[10] | HA-tag[11] | myc-tag[12] | Twin-Strep-tag[8] | polyHis-tag[9] | Spot-tag[13] | Epitope tag of the present invention comprising the core sequence of SEQ ID NO: 4 |
|---|---|---|---|---|---|---|---|---|
| Properties of tag | Size (amino acids) | 8 | 9 | 10 | 28 | 3-10 | 12 | 13-15 |
|  | Mass (kDa) | 1.1 | 1.1 | 1.2 | 2.9 | 0.4-1.4 | 1.4 | ~1.8 |
|  | Charge at pH 7.0 | −3 | −2 | −3 | 0.2 | 0.3-1 | 1.1 | 0 |
|  | pKi | 3.5 | 0 | 3.5 | 8.4 | 14 | 12.1 | 8.1 |
|  | Physical size (nm) | 2.2 | 2.5 | 2.8 | >6 | 0.8-2.8 | 3.3 | 2.0 |
|  | Water solubility | + | poor | + | + | poor | + | + |
|  | Structured in solution | − | − | − | − | − | − | +[14] |
|  | Stable | (+)[15] | (+)[16] | + | + | + | + | + |
|  | Fixation resistant[7] | − | + | − | − | + | + | + |
|  | Unique within model organisms | + | − | − | (+)[2] | (−)[3] | (−)[5] | + |
|  | Possible localizations[18] | N, M, C | N, M, C | N, M, C | N, C | N, C | N, C | N, M, C |
| Properties of binder | Name | M1, M2, M5 | F-7, 1012CA | 9E10 | StrepTactin-XT | Ni$^{2+}$/Co$^{2+}$-chelate | Spot-nanobody | NbALFA$^{ST}$ |
|  | Type | mAb | mAb | mAb | Protein | Inorganic | sdAb | sdAb |
|  | Size (kDa) | ~150 | ~150 | ~150 | ~60 | n.a. | ~15/30[6] | ~15 |
|  | No. of polypeptides | 4 | 4 | 4 | 4 | n.a. | 1 | 1 |
|  | No of binding sites | 2 | 2 | 2 | 2 | 1 | 1-2[6] | 1 |
|  | Affinity | n.d. | n.d. | n.d. | ~60 pM[17] | n.d.[4] | ~6 nM | ~10 pM |
|  | Genetically accessible | − | − | − | + | − | + | + |
| Applications | Protein purification | + | + | + | + | + | + | + |
|  | Imaging | +[1] | +[1] | +[1] | n.d. | − | (+)[6] | + |
|  | In-vivo applications | − | − | − | − | − | − | + | n.a.: not applicable
n.d.: no data available
mAb: monoclonal antibody
sdAb: single-domain antibody

[1]Multiple tags are often used in tandem for optimal performance (Hernan, R., Heuermann, K. & Brizzard, B. Multiple epitope tagging of expressed proteins for enhanced detection. *BioTechniques* 28, 789-793 (2000); Ross-Macdonald, P., Sheehan, A., Roeder, G. S. & Snyder, M. A multipurpose transposon system for analyzing protein production, localization, and function in *Saccharomyces cerevisiae*. Proc Natl Acad Sci USA, 94, 190-195 (1997); Sharrock, R. A. & Clack, T. Heterodimerization of type II phytochromes in *Arabidopsis*. *Proc Natl Acad Sci USA* 101, 11500-11505 (2004); Grumann, J. et al. Applicability of tandem affinity purification MudPIT to pathway proteomics in yeast. Mol. Cell Proeomics 3, 226-237 (2004))

[2]Binder also recognizes biotinylated proteins

[3]Binder recognizes endogenous proteins with multiple accessible histidines.

[4]Depends on chelate and polyHis-tag used

[5]Binder also recognizes endogenous beta-catenin

[6]Binder needs to be dimerized for high-profile imaging applications (Virant, D. et al. A peptide tag-specific nanobody enables high-quality labeling for dSTORM imaging. *Nat Commun* 1-14 (2018). doi:10.1038/s41467-018-03191-2)

[7]Fixation by amine-reactive fixatives and cross-linkers; deduced from sequence

[8]Schmidt, T. G. M. etal. Development of the Twin-Strep-tag ® and its application for purification of recombinant proteins from cell culture supernatants. *Protein Expr. Purif* 92, 54-61 (2013)

[9]Porath, J., Carlsson, J., Olsson, I. & Belfrage, G. Metal chelate affinity chromatography, a new approach to protein fractionation. *Nature* 258, 598-599 (1975); Hochuli, E., Döbeli, H. & Schacher, A. New metal chelate adsorbent selective for proteins and peptides containing neighbouring histidine residues. *J. Chromatogr.* 411, 177-184 (1987)

[10]Hopp, T. P. et al. A Short Polypeptide Marker Sequence Useful for Recombinant Protein Identification and Purification. *Nat Biotechnol* 6, 1204-1210 (1988)

[11]Wilson, I. A. etal. The structure of an antigenic determinant in a protein. *Cell* 37, 767-778 (1984)

[12]Evan, G. I., Lewis, G. K., Ramsay, G. & Bishop, J. M. Isolation of monoclonal antibodies specific for human c-myc proto-oncogene product. *Mol Cell Biol* 5, 3610-3616 (1985)

[13]Virant, D. et al. A peptide tag-specific nanobody enables high-quality labeling for dSTORM imaging. *Nat Commun* 1-14 (2018). doi:10.1038/s41467-018-03191-2; Braun, M. B. etal. Peptides in headlock - a novel high-affinity and versatile peptide-binding nanobody for proteomics and microscopy. *Sci Rep* 6, 19211 (2016)

[14]Petukhov, M. et al. Design of stable alpha-helices using global sequence optimization. *J. Pept. Sci.* 15, 359-365 (2009)

[15]Hunter, M. R., Grimsey, N. L. & Glass, M. Sulfation of the FLAG epitope is affected by co-expression of G protein-coupled receptors in a mammalian cell model. *Sci Rep* 6, 2 7316 (2016)

[16]Schembri, L. et al. The HA tag is cleaved and loses immunoreactivity during apoptosis. *Nat Methods* 4, 107-108 (2007)

[17]https://www.iba-lifesciences.com/tl files/ProteinProductionAssays/5-Immobilization/DynamicBiosensors-Application-Note-StrepTactinXT-switchSENSE.pdf

[18]N: N-terminus; M: in between two folded domains; C: C-terminus.

With this clear objective inventors of the present application designed the epitope tags described herein. The epitope tags of the invention preferably consist about 8 to 25 amino acids and are collectively called ALFA tags.

The inventors of the application decided to take a de-novo approach for generating a new epitope tag. The epitope tag according to the invention is a small, monomeric epitope tag of preferably ≤15aa with minimal size. The sequence is preferably uncharged and hydrophilic at physiological pH and most preferably, it is devoid of residues prone to be modified by amine-reactive fixatives and cross-linkers. The size stands in contrast to larger tags, such as, e.g., a FLAG tag trimer, which is commonly used in a 3× tandem in order to increase avidity, or even larger fluorescent protein. Further, the epitope tag of the present invention has no counterpart in eukaryotic or prokaryotic sequence databanks, which minimizes the risk of cross-binding to native structures. This stands e.g. in contrast to the SPOT-Tag®, which is described in WO 2017/085086 A1.

A further advantage of the epitope tag of the invention is that it is compatible to common amine-reactive fixatives (paraformaldehyde (PFA), glutaraldehyde (GA)), unlike e.g. the Myc tag. It is also compatible with methanol fixation. A further advantage of the epitope tag of the present invention is that it is not restricted in terms of localization (N, C or in between proteins), unlike the EPEA tag, which is described in WO 2011/147890 A1.

Without wishing to be bound by theory, it is believed that the epitope tag according to the invention forms a stable alpha-helical structure. Formation of a stable alpha helix is believed to be advantageous over differently folded, non-folded or non-stably folded structures, because certain antibodies, such as single domain antibodies (sdAb) or nanobodies are believed to prefer defined three-dimensional surfaces for binding. In the past, it has been very hard to generate single domain antibodies binding to natively unfolded peptides, which resulted in sdAb with weak to moderate binding affinities only. The inventors of the present application therefore focused on providing epitope tags that are believed to form small alpha-helices that are stably folded in solution, because such structures are the smallest entities forming stable secondary structures as a monomer. Without wishing to be bound by theory, it is believed that the alpha-helical structure efficiently and spontaneously refolds even after exposure to harsh chemical treatment. Further it is believed that due to its helical structure, the tag is smaller than most unstructured linear epitope tags. In addition, the epitope tags of the invention can be placed at the N- or C-terminus of a target protein or even in between two folded protein domains without compromising proper targeting and folding of target proteins.

Finding the ideal binder(s), however, proved to be challenging. While conventional antibodies would indeed fulfill most requirements, their large size makes them suboptimal for the current super-resolution microscopy (Fornasiero, E. F. & Opazo, F. Super-resolution imaging for cell biologists: Concepts, applications, current challenges and developments. *Bioessays* 37, 436-451 (2015); Mikhaylova, M. et al. Resolving bundled microtubules using anti-tubulin nanobodies. *Nat Commun* 6, 7933 (2015) and cannot be encoded genetically to target intracellular targets in living cells. The inventors of the present application therefore chose to develop a camelid single-domain antibody (sdAb, also know as nanobody (Muyldermans, S. Nanobodies: Natural Single-Domain Antibodies. *Annu Rev Biochem* (2013). doi: 10.1146/annurev-biochem-063011-092449) fulfilling the set criteria. For this, a novel in-house selection method called "Celline" allowed the inventors to generate alpaca-derived sdAb with exceedingly high affinity in a very timely manner. The antibodies of the invention in combination with the epitope tags of the invention proved to be ideal for imaging and intracellular detection of ALFA$^{ST}$-tagged target proteins and allowed very efficient and clean immuno-precipitations.

The present invention also provides high-affinity antibodies for the epitope tag of the invention. Some of the antibodies are monovalent sdAb-based binders. Monovalent binding stands in contrast to epitope tags that are bound by conventional antibodies. While the SPOT-Tag® is bound by an sdAb, the SPOT-Tag®-binding sdAb is employed as a dimer for some applications of the SPOT-Tag® in order to increase avidity. Utilization of monovalent antibodies has the advantage that cluster formation can be prevented. It is further believed that due to the alpha-helical structure of the epitope tag, the inventors of the present invention were able to generate single domain antibodies that bind to the epitope tag of the invention with a $K_d$ in the range of about 10 pM, which is approximately a ~1000-fold higher affinity than comparable epitope tag/sdAb systems, as e.g. described in WO 2017/085086 A1 or WO 2011/147890 A1.

For some of the epitope tags of the present invention, such as SEQ ID NOs:05-07, it was virtually impossible to efficiently separate the antibody comprising the sequence of SEQ ID NO:133 from the tag under native conditions. In some cases, this might be limiting for the application of SEQ ID NOs:05-07 for purification of native proteins and their interacting partners. Solving the crystal structure of the high affinity complex of the antibody of SEQ ID NO: 133 and the peptide of SEQ ID NO: 179 allowed the inventors to map the interaction determinants in detail and to engineer a new versions of the single-domain antibody that allows a competitive elution of ALFA$^{ST}$_tagged target proteins and interacting partners under native conditions. An exemplary antibody for this purpose comprises the amino acid sequence of SEQ ID NO: 134.

The epitope tag and antibody system presented here is suited for an exceptionally broad range of applications ranging from biotechnology to cell biology. A single tag can therefore simultaneously replace a great variety of traditional epitope tags.

The present invention therefore relates to a fusion protein comprising (a) a peptide comprising the sequence of X1-X2-X3-X4-X5-X6-X7-X8-X9-R-L-X12-X13 (SEQ ID NO: 01), wherein X1 is G or S or T or P, X2 is R or G or A or E or P, X3 is L or V, X4 is E or Q, X5 is E or Q, X6 is E or Q, X7 is L or I or V, X8 is R or A or Q or E, X9 is R or A or Q or E, X12 is S or T or D or E or P or A or no amino acid, and wherein X13 is E or K or P or S or A or D or no amino acid; and (b) a polypeptide. In the fusion protein of the invention, the peptide may serve the purpose of an epitope tag.

The term "peptide" as used herein refers to a linear series of amino acids connected one to the other preferably by peptide bonds between the alpha-amino and carboxy groups of adjacent residues. As used herein the term "amino acid" refers to either natural and/or unnatural or synthetic amino acids, including glycine and both the D or L optical isomers, and amino acid analogs and peptidomimetics, with proteogenic amino acids being preferred. A "proteinogenic amino acid" is an amino acid that can be incorporated biosynthetically into proteins during translation. Currently, there are 22 known genetically encoded (proteinogenic) amino acids, 20 in the standard genetic code and an additional 2 that can be incorporated by special translation mechanisms. The "peptide" as used herein preferably comprises no more than about 50 amino acids.

The term "polypeptide" as used herein usually refers to a peptide having at least about 30, at least about 40, or at least about 50 amino acids. The term "protein" as used herein comprises one or more polypeptides.

The term "fusion protein" as used herein refers to a polypeptide or protein comprising two or more subunits. At least one of the subunits is preferably a protein or polypeptide, and at least one of the subunits is preferably a peptide. Within the fusion protein, these subunits may be linked by covalent or non-covalent linkage. Preferably, the fusion protein is a translational fusion between the two or more subunits. The translational fusion may be generated by genetically engineering the coding nucleotide sequence for one subunit in a reading frame with the coding nucleotide sequence of a further subunit. Subunits may be interspersed by a linker.

If one or more of the subunits is part of a protein (complex) that consists of more than one polypeptide chain, the term "fusion protein" may also refer to the protein comprising the fused sequences and all other polypeptide chain(s) of the protein (complex).

As used herein, an "epitope tag" refers to a stretch of amino acids to which a specific antibody or proteinaceous molecule with antibody-like function can be raised. Such an epitope tag may allow for specifically identifying and/or tracking of the tagged polypeptide or protein that may be present in a living organism or cultured cells. Detection of the tagged molecule can be achieved using a number of different techniques. Examples of such techniques include: immunohistochemistry, immunoprecipitation, flow cytometry, immunofluorescence microscopy, electron microscopy, ELISA, immunoblotting ("Western blot"), and affinity chromatography. The epitope tag adds a known epitope (antibody binding site) on the subject polypeptide, to provide binding of a known and often high-affinity antibody. An epitope tag may also be used for isolation and/or purification of the tagged molecule, e.g. by pull-down applications.

In the fusion protein of the invention, the peptide, i.e. the epitope tag, may be located at any position of the fusion protein. The peptide may be fused to the N-terminus or the C-terminus of the polypeptide. Alternatively, the peptide may be fused to the polypeptide at a position between the N-terminus and the C-terminus of the polypeptide. As an illustrative example, the peptide may be fused in between two domains of the polypeptide.

The polypeptide comprised in the fusion protein may have a stable fold that is independent from the presence or absence of the peptide. This means that the peptide preferably does not alter or interfere with the native structure of the polypeptide.

The peptide itself has preferably an alpha-helical structure. A solved crystal structure of an antibody having the sequence of SEQ ID NO: 133 in complex with the ALFA$^{ST}$ peptide comprising the sequence of Ac-PSR-LEEELRRRLTEP-Amide (SEQ ID NO: 179) shows that the epitope tag binds to the nanobody as a stably folded alpha helix. The structure is believed to explain the extraordinarily tight binding. An "alpha helical structure" as used herein refers to a secondary structure in the form of an alpha helix. It is preferred that the alpha helical secondary structure of the peptide is independent from a fusion partner. This means that the peptide is preferably capable of forming an alpha helical secondary structure in physiological buffers if the peptide is in form of an isolated peptide and also if the peptide is part of the fusion protein.

The peptide may be specifically recognized by a camelid VHH domain comprising the CDR sequences GVTISAL-NAMAMG (SEQ ID NO: 115), AVSERGNAM (SEQ ID NO: 116), and LEDRVDSFHDY (SEQ ID NO: 117). The peptide may further be specifically recognized by other antibodies described herein.

In the fusion protein of the invention, the peptide may be fused to the polypeptide either by direct fusion or through a linker. A "linker" as used herein joins together two or more subunits of a fusion protein as described herein. The linkage can be covalent. A preferred covalent linkage is via a peptide bond, such as a peptide bond between amino acids. A preferred linker is a peptide linker. Said linker preferably comprises one or more amino acids, such as 1, 2, 3, 4, 5, 6, 7, 8, 9, 10, 11, 12, 13, 14, 15, 16, 17, 18, 19, 20 or more amino acids. Preferred peptide linkers include glycine-serine (GS) linkers, glycosylated GS linkers, and proline-alanine-serine polymer (PAS) linkers. A GS linker may be a $(G_4S)_3$ linker as described in SEQ ID NO: 159.

The polypeptide comprised in the fusion protein of the invention may comprise at least one protein domain. A "protein domain" as used herein refers to a part of a given protein sequence and (tertiary) structure that can function and/or exist independently of the rest of the protein chain. The protein domain preferably forms a compact three-dimensional structure and often can be independently stable and folded. A protein domain may further form a functional unit. The polypeptide comprised in the fusion protein may comprise more than one protein domain, such as 2, 3, 4, or even more protein domains. A preferred location for the peptide may be outside of the protein domain. This can be N-terminal or C-terminal of the at least one protein domain of the polypeptide, or in between two protein domains of the polypeptide. The polypeptide comprised in the fusion protein of the invention may be a globular protein, and membrane protein, a fibrous protein, or a natively unfolded protein, or a subunit or domain of the globular protein, membrane protein, fibrous protein, or natively unfolded protein.

The peptide comprised in the fusion protein of the invention may have a length of about 8 to about 25 amino acids, preferably about 10 to about 18 amino acids, preferably about 12 to about 17 amino acids, preferably 12 to 15 amino acids. The polypeptide comprised in the fusion protein of the invention may have a length of at least 3, 4, 5, 6, 7, 8, 9, 10, 15, 20, 25, 30, 40, 50, 60, 70, 80, 90, or 100 amino acids. The polypeptide may be polypeptide or protein that naturally occurs in a cell that expresses the fusion protein of the invention.

The fusion protein of the invention may comprise a peptide comprising the sequence of X1-X2-L-E-X5-E-X7-R-R-R-L-X12-X13 (SEQ ID NO: 02), wherein X1 is G or S or P or T, X2 is R or G or P, X5 is E or Q, X7 is L or I, X12 is S or T or P or A or D or E, and wherein X13 is P or A or S or A or D or E or no amino acid. This sequence defines the core structure of the peptide and may further comprise up to two additional amino acids at the N terminus and up to two additional amino acids at the C terminus. Such additional amino acids at the ends of the core structure of the peptide usually do not necessarily influence the secondary structure of the of the peptide or specific binding of the peptide to an antibody specific for the peptide, but may serve as linker structures in the fusion protein. Accordingly, type and number of the additional amino acids may depend on the location of the peptide in the fusion protein and may vary depending on whether the peptide is located N-terminal or C-terminal or somewhere in between of the polypeptide. A peptide comprising the sequence of SEQ ID NO: 02 may have a $T_{1/2}$ of at least about 2 min for dissociation from a single domain antibody comprising the sequence of SEQ ID NO: 133, e.g. when measured in an assay as essentially described in Example 1. The peptide may have a $K_d$ of about 30 nM or less for the binding to the single domain antibody comprising the sequence of SEQ ID NO: 133.

The peptide comprised in the fusion protein of the invention may comprise N-terminal of X1 the amino acids Xa-Xb, wherein Xa is D or S or G or M or P or no amino acid and Xb is S or D or P or M or R or G no amino acid.

The peptide comprised in the fusion protein of the invention may comprise C-terminal of X13 the amino acids Xy-Xz, wherein Xy is G or S or P or D or A or E or K or no amino acid, and Xz is S or P or no amino acid.

The fusion protein of the invention may comprise a peptide comprising as a core structure the sequence of X1-X2-L-E-X5-E-L-R-R-L-X12-X13 (SEQ ID NO: 03), wherein X1 is S or T, X2 is R or G, X5 is E or Q, X12 is T or D or E, and wherein X13 is A or D or E or no amino acid. Such a peptide may have a T1/2 of at least about 100 min for dissociation from a single domain antibody comprising the sequence of SEQ ID NO: 133, e.g. when measured in an assay as essentially described in Example 1. The peptide may have a $K_d$ of about 1 nM or less for the binding to the single domain antibody comprising the sequence of SEQ ID NO: 133. Such a peptide may comprise the sequence of S-R-L-E-E-E-L-R-R-L-T-E (SEQ ID NO: 04) or a variant thereof, wherein the variant has as compared to (SEQ ID NO: 04) 1 to 5 mutations selected from the group consisting of: S1→T, R2→G, E5→Q, T12→D, and T12→E, E13→A, E13→D, and deletion of E13. The variant may have as compared to SEQ ID NO: 04 following mutations: (a) S1→T and E13→A; (b) R2→G; (c) R2→G and E5→Q; (d) R2→G, E5→Q and E13→A; (e) R2→G, E5→Q, and T12→D, and E13→A; (f) R2→G, E5→Q, and T12→E, and E13→A; (g) T12→D and E13→A; (h) T12→E and E13→A; (i) and E13→A; (j) and E13→D; or (k) deletion of E13.

A peptide comprising as a core structure the sequence SEQ ID NO: 03 may comprise N-terminal of X1 the amino acids Xa-Xb, wherein Xa is S or G or M or P or no amino acid, and Xb is R or G or S or P or M or no amino acid. Xa-Xb may be selected from the group consisting of P, M-P, G-R, P-G, P-S, S-P, G-P, S-P, M, and M-S, preferably P or M-P. Such a peptide may also comprise C-terminal of X13 the amino acids Xy-Xz, wherein is P or D or A or no amino acid, and Xz is P or S or no amino acid. Xy-Xz may be selected from the group consisting of no amino acid, P, D-P, A, and A-S, preferably no amino acid or P. The peptide may comprise a combination of Xa-Xb and Xy-Xz selected from the group consisting of: (a) M-P and P; (b) P and P; and (c) P and no amino acid.

A peptide comprised in the fusion protein of the invention may have the core structure of SEQ ID NO: 03 and may comprise a sequence selected from the group consisting of:

(a)
    (SEQ ID NO: 05)
MPSRLEEELRRRLTEP;

(b)
    (SEQ ID NO: 06)
PSRLEEELRRRLTEP;

(c)
    (SEQ ID NO: 07)
PSRLEEELRRRLTE;

(d)
    (SEQ ID NO: 08)
GRSRLEEELRRRLTA;

(e)
    (SEQ ID NO: 09)
PGSRLEEELRRRLTAP;

(f)
    (SEQ ID NO: 10)
PSTRLEEELRRRLTAP;

(g)
    (SEQ ID NO: 11)
SPSRLEEELRRRLTAP;

(h)
    (SEQ ID NO: 12)
SPSRLEEELRRRLDAP;

(i)
    (SEQ ID NO: 13)
SPSRLEEELRRRLEAP;

(j)
    (SEQ ID NO: 14)
SPSRLEEELRRRLTDP;

(k)
    (SEQ ID NO: 15)
SPSRLEEELRRRLTEP;

(l)
    (SEQ ID NO: 16)
SPSRLEEELRRRLTADP;

(m)
    (SEQ ID NO: 17)
SPSGLEEELRRRLTEP;

(n)
    (SEQ ID NO: 18)
GPSRLEEELRRRLT;

(o)
    (SEQ ID NO: 19)
GPSRLEEELRRRLTA;

(p)
    (SEQ ID NO: 20)
GPSRLEEELRRRLTAA;

(q)
    (SEQ ID NO: 21)
GPSRLEEELRRRLTAAS;

(r)
    (SEQ ID NO: 22)
SPSGLEQELRRRLTAP;

(s)
    (SEQ ID NO: 23)
SPSGLEQELRRRLDAP;

(t)
    (SEQ ID NO: 24)
SPSGLEQELRRRLEAP;

(u)
    (SEQ ID NO: 25)
SPSGLEQELRRRLTEP;

(v)
    (SEQ ID NO: 26)
GPSRLEEELRRRLTAP;

-continued (w)
```
                            (SEQ ID NO: 27)
GPSRLEEELRRRLTEP;
```

(x)
```
                            (SEQ ID NO: 28)
GPSRLEEELRRRLTE;
```

(y)
```
                            (SEQ ID NO: 29)
MSRLEEELRRRLTEP;
```
and (z)
```
                            (SEQ ID NO: 30)
MSSRLEEELRRRLTEP.
```

The fusion protein of the invention may comprise a peptide comprising as a core structure the sequence of X1-X2-L-E-X5-E-X7-R-R-R-L-X12-X13 (SEQ ID NO: 31), wherein X1 is G or S or P, X2 is R or G, X5 is E or Q, X7 is L or I, X12 is S or T or P or A, and X13 is P or A or S or no amino acid. Such a peptide may have a $T_{1/2}$ from about 2.5 min to about 30 min for dissociation from a single domain antibody comprising the sequence of SEQ ID NO: 133, e.g. when measured in an assay as essentially described in Example 1. The peptide may have a $K_d$ of about 3-40 nM or less for the binding to the single domain antibody comprising the sequence of SEQ ID NO: 133.

Such a peptide may comprise the sequence of G-R-L-E-E-E-L-R-R-R-L-S(SEQ ID NO: 32) or a variant thereof, wherein the variant has as compared to (SEQ ID NO: 32) 1 to 6 mutations selected from the group consisting of: G1→S, G1→P, R2→G, E5→Q, L7→I, S12→T, S12→P, and S12→A, addition of P13, addition of A13, and addition of S13. The variant may have as compared to SEQ ID NO: 32 following mutations: (a) G1→S, R2→G, E5→Q, and addition of P13; (b) R2→G, E5→Q, S12→T, and addition of A13; (c) G1→P, R2→G, E5→Q, S12→T, and addition of A13; (d) G1→S, R2→G, E5→Q, S12→T, and addition of P13; (e) G1→S, R2→G, S12→T, and addition of A13; (f) G1→S, R2→G, E5→Q, and S12→T; (g) G1→S, R2→G, E5→Q, S12→T, and addition of A13; (h) G1→S and S12→P, and addition of P13; (i) G1→S, R2→G, E5→Q, S12→T, and addition of P13; (j) E5→Q L7→I, and addition of P13; (k) addition of P13; or (1) S12→A.

A peptide comprising as a core structure the sequence SEQ ID NO: 31 may comprise N-terminal of X1 the amino acids Xa-Xb, wherein Xa is M or S or P or D or G or no amino acid, and Xb is S or D or P or no amino acid. Xa-Xb may be selected from the group consisting of M-S, S-D, P-D, P-S, D-S, S-P, and G-P, preferably M-S. Such a peptide may also comprise C-terminal of X13 the amino acids Xy-Xz, wherein Xy is G or P or A or E or K or S or no amino acid, and Xz is P or S or no amino acid. Xy-Xz may be selected from the group consisting of no amino acid, G, P, A, E-P, A-S, K, and S, preferably no amino acid. The peptide may comprise a combination of Xa-Xb and Xy-Xz that is M-S and no amino acid.

A peptide comprised in the fusion protein of the invention may have the core structure of SEQ ID NO: 31 and may comprise a sequence selected from the group consisting of:

(a) (SEQ ID NO: 32)
GRLEEELRRRLS;

-continued (b) (SEQ ID NO: 33)
MSGRLEEELRRRLSP;

(c) (SEQ ID NO: 34)
SDSGLEQELRRRLSPG;

(d) (SEQ ID NO: 35)
PDGGLEQELRRRLTAP;

(e) (SEQ ID NO: 36)
PSGGLEQELRRRLTAP;

(f) (SEQ ID NO: 37)
DSPGLEQELRRRLTAP;

(g) (SEQ ID NO: 38)
PDSGLEQELRRRLTPA;

(h) (SEQ ID NO: 39)
SPSGLEEELRRRLTAEP;

(i) (SEQ ID NO: 40)
GPSGLEQELRRRLT;

(j) (SEQ ID NO: 41)
GPSGLEQELRRRLTAAS;

(k) (SEQ ID NO: 42)
SPSRLEEELRRRLPSK;

(l) (SEQ ID NO: 43)
SPSGLEQELRRRLTPS;

(m) (SEQ ID NO: 44)
SPGRLEQEIRRRLSPS;

(n) (SEQ ID NO: 45)
PSGRLEEELRRRLSPS;

(o) (SEQ ID NO: 46)
PSGRLEEELRRRLS;

(p) (SEQ ID NO: 47)
PSGRLEEELRRRLA;
and (q) (SEQ ID NO: 48)
PSGRLEEELRRRLSP.

The fusion protein of the invention may comprise a peptide comprising as a core structure the sequence of X1-X2-L-E-X5-E-L-R-R-R-L-X12-X13 (SEQ ID NO: 49), wherein X1 is S or G or P, X2 is R or G or P, X5 is E or Q, X12 is S or T or D or E, and X13 is P or A or D or no amino acid. Such a peptide may have a T1/2 from about 20 min to about 100 min for dissociation from a single domain antibody comprising the sequence of SEQ ID NO: 133, e.g. when measured in an assay as essentially described in Example 1. The peptide may have a $K_d$ of about 1-5 nM or less for the binding to the single domain antibody comprising the sequence of SEQ ID NO: 133.

A peptide comprising as a core structure the sequence SEQ ID NO: 49 may comprise N-terminal of X1 the amino acids Xa-Xb, wherein Xa is P or D or S or G or no amino acid, and Xb is D or S or P or no amino acid. Such a peptide may also comprise C-terminal of X13 the amino acids Xy-Xz, wherein Xy is G or P or E or D or S or no amino acid, and Xz is P or no amino acid.

A peptide comprised in the fusion protein of the invention may have the core structure of SEQ ID NO: 49 and may comprise a sequence selected from the group consisting of:

(a)
PDSGLEQELRRRLSPG;                    (SEQ ID NO: 50)

(b)
PDSGLEQELRRRLTAP;                    (SEQ ID NO: 51)

(c)
PSSGLEQELRRRLTAP;                    (SEQ ID NO: 52)

(d)
DPSGLEQELRRRLTAP;                    (SEQ ID NO: 53)

(e)
DSGPLEQELRRRLTAP;                    (SEQ ID NO: 54)

(f)
SPSRLEEELRRRLTAEP;                   (SEQ ID NO: 55)

(g)
SPSGLEEELRRRLTAP;                    (SEQ ID NO: 56)

(h)
SPSGLEEELRRRLDAP;                    (SEQ ID NO: 57)

(i)
SPSGLEEELRRRLEAP;                    (SEQ ID NO: 58)

(j)
SPSGLEEELRRRLTDP;                    (SEQ ID NO: 59)

(k)
SPSGLEEELRRRLTADP;                   (SEQ ID NO: 60)

(l)
GPSGLEQELRRRLTA;                     (SEQ ID NO: 169)

(m)
SPSGLEQELRRRLTDP;                    (SEQ ID NO: 170)

(n)
SPSGLEQELRRRLTADP;                   (SEQ ID NO: 171)

(o)
SPSGLEQELRRRLTAEP;                   (SEQ ID NO: 172)

(p)
DSPGLEQELRRRLTAP;                    (SEQ ID NO: 173)
and (q)
SPSGLEQELRRRLSPS.                    (SEQ ID NO: 174)

The fusion protein of the invention may comprise a peptide comprising as a core structure the sequence of X1-X2-X3-X4-X5-X6-X7-X8-X9-R-L-X12-X13 (SEQ ID NO: 61), wherein X1 is G or S, X2 is R or G or A or E, X3 is L or V, X4 is E or Q, X5 is E or Q, X6 is E or Q, X7 is L or I or V, X8 is R or A or Q or E, X9 is R or A or Q or E, X12 is S or T or L or no amino acid, and X13 is K or P or S or no amino acid. Such a peptide may have a $T_{1/2}$ from about 2 min to about 10 min for dissociation from a single domain antibody comprising the sequence of SEQ ID NO: 133, e.g. when measured in an assay as essentially described in Example 1. The peptide may have a Kd of about 10-50 nM or less for the binding to the single domain antibody comprising the sequence of SEQ ID NO: 133.

A peptide comprising as a core structure the sequence SEQ ID NO: 61 may comprise N-terminal of X1 the amino acids Xa-Xb, wherein Xa is D or S or G or M or no amino acid and Xb is S or D or P or M or no amino acid. Such a peptide may also comprise C-terminal of X13 the amino acids Xy-Xz, wherein Xy is G or S or P or no amino acid, Xz is S or no amino acid.

A peptide comprised in the fusion protein of the invention may have the core structure of SEQ ID NO: 61 and may comprise a sequence selected from the group consisting of:

(a)
GRLEEELRRRLS;                        (SEQ ID NO: 32)

(b)
MSGRLEEELRRRLSP;                     (SEQ ID NO: 33)

(c)
DSGRLEEELRRRLSKG;                    (SEQ ID NO: 62)

(d)
DSGRLEEELRRRLSPG;                    (SEQ ID NO: 63)

(e)
SDSGLEEELRRRLSPG;                    (SEQ ID NO: 64)

(f)
SDSGVEEELRRRLSPG;                    (SEQ ID NO: 65)

(g)
SDSAVEEELRRRLSPG;                    (SEQ ID NO: 66)

(h)
SDSGLQEELRRRLSPG;                    (SEQ ID NO: 67)

(i)
SDSGLEEQLRRRLSPG;                    (SEQ ID NO: 68)

(j)
SDSGLEEEIRRRLSPG;                    (SEQ ID NO: 69)

(k)
SDSGLEEEVRRRLSPG;                    (SEQ ID NO: 70)

(l)
DSGELEEELRRRLSPG;                    (SEQ ID NO: 71)

(m)
DSGRLEQELRRRLSPG;                    (SEQ ID NO: 72)

-continued (n)
DSGRLEEEIRRRLSPG; (SEQ ID NO: 73)

(o)
DSGRLEQEIRRRLSPG; (SEQ ID NO: 74)

(p)
DSGRLEQEIARRLSPG; (SEQ ID NO: 75)

(q)
DSGRLEQEIQRRLSPG; (SEQ ID NO: 76)

(r)
DSGRLEQEIERRLSPG; (SEQ ID NO: 77)

(w)
DSGRLEQEIRARLSPG; (SEQ ID NO: 78)

(t)
DSGRLEQEIRQRLSPG; (SEQ ID NO: 79)

(u)
DSGRLEQEIRERLSPG; (SEQ ID NO: 80)

(v)
GPSRLEEELRRRL; (SEQ ID NO: 81)

(w)
MSGLEQELRRRLTPS; (SEQ ID NO: 82)

(x)
MSGRLEEELRRRLSPS; (SEQ ID NO: 83)

(y)
SPSAVEEELRRRLSPS; (SEQ ID NO: 84)

(z)
GPSAVEEELRRRLS; (SEQ ID NO: 85)

(aa)
MPSGLEQELRRRLTPS; (SEQ ID NO: 86)

(bb)
MSSGLEQELRRRLTPS; (SEQ ID NO: 87)

(cc)
MPSGRLEEELRRRLSPS; (SEQ ID NO: 88)

(dd)
MSGRLEEELRRRLSP. (SEQ ID NO: 89)

The fusion protein of the invention may in complex with a binding partner that specifically binds to the peptide comprised in the fusion protein. Such a specific binding partner may be an antibody disclosed herein.

The fusion protein of the invention may comprise an antibody moiety. The antibody moiety may be a single domain antibody. Such antibody moiety may specifically bind to a target. Such a target may be a cell. For example, the specific target may comprise or be a structure on a cell surface, such as a cell surface receptor. A preferred target is CD62L.

The present invention further provides an antibody that specifically binds to the peptide comprised in the fusion protein of the invention. Such an antibody may be a monovalent antibody. In preferred embodiments, an antibody of the invention comprises or consists of a camelid VHH domain. In preferred embodiments, an antibody of the invention is a single domain antibody, such as a camelid single domain antibody.

The term "antibody" generally refers to a proteinaceous binding molecule with immunoglobulin-like functions. Typical examples of an antibody are, but are not limited to, immunoglobulins, as well as derivatives or functional fragments thereof which still retain the binding specificity. Techniques for the production of antibodies are well known in the art. The term "antibody" also includes immunoglobulins (Ig's) of different classes (i.e. IgA, IgG, IgM, IgD, IgE, IgY etc.) and subclasses (such as IgG1, IgG2 etc.), even if recombinantly produced in foreign hosts using techniques known to those skilled in the arts. Illustrative examples of an antibody are full length immunoglobulins, $F_{ab}$ fragments, $F(ab')_2$, $F_V$ fragments, single-chain $F_V$ fragments (sc$F_V$), diabodies or domain antibodies (Holt U et al., Trends Biotechnol. 21(11), 2003, 484-490). Domain antibodies may be single domain antibodies, single variable domain antibodies or immunoglobulin single variable domain having only one variable domain, which may be VH or VL, that specifically bind an antigen or epitope independently of other V regions or domains. A particularly preferred single domain antibody is a VHH domain of a heavy chain only antibody. Such an immunoglobulin single variable domain may not only encompass an isolated antibody single variable domain polypeptide, but also a larger polypeptide that includes or consists of one or more monomers of an antibody single variable domain polypeptide sequence. It is understood that a single domain antibody may comprise a VHH domain and a fusion partner, such as a protein or peptide tag. The definition of the term "antibody" thus also includes embodiments such as chimeric, single chain and humanized antibodies. The term "antibody" may also include fragments of antibodies.

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, or cattle. According to the invention, a single domain antibody as used herein is preferably derived from a naturally occurring antibody known as heavy chain antibody devoid of light chains. Such single domain antibodies are disclosed in WO 94/04678 for example. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, dromedary, llama, vicuña, alpaca and guanaco. Other species besides Camelidae may produce heavy chain antibodies naturally devoid of light chain. As an illustrative example, it is known that sharks produce heavy chain antibodies naturally devoid of light chains (commonly named IgNAR), which also comprise a VHH domain. In addition, VHHs may be obtained from synthetic libraries. All such VHHs are within the scope of the invention.

VHHs, according to the present invention, and as known to the skilled addressee are preferably heavy chain variable domains derived from immunoglobulins naturally devoid of light chains such as those derived from Camelidae as described in WO 94/04678 (and referred to hereinafter as VHH domains or nanobodies). VHH molecules are about 10× smaller than IgG molecules. They are single polypeptides and very stable, resisting extreme pH and temperature conditions. Moreover, they are highly resistant to the action of proteases, which is not the case for conventional antibodies. Furthermore, in vitro expression of VHHs or expression in prokaryotic or eukaryotic organisms suited for recombinant protein expression produces high yield, properly folded functional VHHs. It is understood that single domain antibody according to the invention is preferably a VHH.

An antibody according to the invention may carry one or more domains that have a sequence with at least about 60%, at least about 70%, at least about 75%, at least about 80%, at least about 85%, at least about 90%, at least about 92%, at least about 95%, at least about 96%, at least about 97%, at least about 98% or at least about 99% sequence identity with a corresponding naturally occurring domain of an immunoglobulin naturally devoid of light chains. It is noted in this regard, the term "about" or "approximately" as used herein means within a deviation of 20%, such as within a deviation of 10% or within 5% of a given value or range.

"Percent (%) sequence identity" with respect to amino acid sequences disclosed herein is defined as the percentage of amino acid residues in a candidate sequence that are pair-wise identical with the amino acid residues in a reference sequence, i.e. an antibody molecule of the present disclosure, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions", "HVR," or "HV," or "complementarity determining regions" (CDRs). The more conserved (i.e., non-hypervariable) portions of the variable domains are called the "framework" regions (FR). The variable domains of naturally occurring heavy and light chains each include four FR regions, largely adopting a β-sheet configuration, connected by three hypervariable regions, which form loops connecting, and in some cases forming part of, the β-sheet structure. The hypervariable regions in each chain are held together in close proximity by the FR and, with the hypervariable regions from the other chain, contribute to the formation of the antigen-binding site (see Kabat et al., see below). Generally, naturally occurring immunoglobulins include six CDRs (see below); three in the VH (H1, H2, H3), and three in the VL (L1, L2, L3). In naturally occurring immunoglobulins, H3 and L3 display the most diversity of the six CDRs, and H3 in particular is believed to play a unique role in conferring fine specificity to immunoglobulins. Immunoglobulins naturally devoid of light chains, however, include three CDRs that are in the VHH region. The constant domains are not directly involved in antigen binding, but exhibit various effector functions, such as, for example, antibody-dependent, cell-mediated cytotoxicity and complement activation.

Each VHH, VH and VL has three CDRs and four FRs, arranged from amino-terminus (N-terminus) to carboxy-terminus (C-terminus) in the following order: FR1, CDR1, FR2, CDR2, FR3, CDR3, FR4. The variable regions of the heavy and/or light chains contain a binding domain that interacts with an epitope of an antigen. The term "immunoglobulin" may refer to protein that may two heavy chains without light chains, such as e.g. an antibody devoid of light chains, or an antigen-binding portion thereof. An immunoglobulin may also include at least two heavy (H) chains and two light (L) chains linked by disulfide bonds, or an antigen-binding portion thereof.

An immunoglobulin when used herein, may be a dimeric glycosylated protein composed of two heavy chains such as a camelid heavy chain only IgG (hcIgG) or a shark IgNAR. An immunoglobulin as used herein may also be a tetrameric glycosylated protein composed of two light (L) chains of approximately 25 kDa each and two heavy (H) chains of approximately 50 kDa each.

When used in connection with a protein or peptide, the term "amino acid" or "amino acid residue" typically refers to an α-amino carboxylic acid having its art recognized definition such as an amino acid selected from the group consisting of: L-alanine (Ala or A); L-arginine (Arg or R); L-asparagine (Asn or N); L-aspartic acid (Asp or D); L-cysteine (Cys or C); L-glutamine (Gln or Q); L-glutamic acid (Glu or E); glycine (Gly or G); L-histidine (His or H); L-isoleucine (Ile or I): L-leucine (Leu or L); L-lysine (Lys or K); L-methionine (Met or M); L-phenylalanine (Phe or F); L-proline (Pro or P); L-serine (Ser or S); L-threonine (Thr or T); L-tryptophan (Trp or W); L-tyrosine (Tyr or Y); and L-valine (Val or V), although modified, synthetic, or rare amino acids such as e.g. taurine, ornithine, selenocysteine, homocystine, hydroxyproline, thioproline, iodo-tyrosine, 3-nitro-tyrosine, ornithine, citrulline, canavanine, 5-hydroxytryptophane, carnosine, cycloleucine, 3,4-dihydroxy phenylalanine, N-acetylcysteine, prolinol, allylglycine or acetidine-2-carboxylic acid may be used as desired. Generally, amino acids can be grouped as having a nonpolar side chain (e.g., Ala, Cys, Ile, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

A target according to the invention is any substance of biological or chemical origin to which an antibody of the invention is capable to detect directly or indirectly. Targets may be, for example, proteins, peptides, nucleic acids, oligonucleic acids, saccharides, polysaccharides, glycoproteins. Examples include, but are not limited to therapeutic targets, diagnostic targets, receptors, receptor ligands, viral coat proteins, immune system proteins, hormones, enzymes, antigens, cell signaling proteins, or a fragment thereof. Targets may be native protein or a fragment thereof, a homologous sequence thereof, a functional portion thereof, or a functional portion of a homologous sequence.

The term "epitope", also known as the "antigenic determinant", refers to the portion of an antigen to which an antibody specifically binds, thereby forming a complex. Thus, the term "epitope" includes any molecule or protein determinant capable of specific binding to an immunoglobulin or T-cell receptor. The binding site(s) (paratope) of an antibody molecule described herein may specifically bind to/interact with conformational or continuous epitopes, which are unique for the target structure. Epitopic determinants usually consist of chemically active surface groupings of molecules such as amino acids or sugar side chains and usually have specific three dimensional structural characteristics, as well as specific charge characteristics. Epitope determinants may include chemically active surface groupings of molecules such as amino acids, sugar side chains, phosphoryl, or sulfonyl, and, in certain embodiments, may have specific three dimensional structural characteristics, and/or specific charge characteristics. With regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen (Sela, M., Science (1969) 166, 1365-1374; Laver, W. G., et al. Cell (1990) 61, 553-556). The two or more discrete amino acid residues contributing to the epitope may be present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain. As an illustrative example, a "context-dependent" CD3 epitope refers to the conformation of said epitope. Such a context-dependent epitope, localized on the epsilon chain of CD3, can only develop its correct conformation if it is embedded within the rest of the epsilon chain and held in the right position by heterodimerization of the epsilon chain with either CD3 gamma or delta chain. In contrast thereto, a context-independent CD3 epitope may be an N-terminal 1-27 amino acid residue polypeptide or a functional fragment thereof of CD3 epsilon. Generally, epitopes can be linear in nature or can be a discontinuous epitope. Thus, as used herein, the term "conformational epitope" refers to a discontinuous epitope formed by a spatial relationship between amino acids of an antigen other than an unbroken series of amino acids. The term "epitope" also includes an antigenic determinant of a hapten, which is known as a small molecule that can serve as an antigen by displaying one or more immunologically recognized epitopes upon binding to larger matter such as a larger molecule e.g. a protein.

An antibody or antibody molecule/fragment is said to "specifically" bind to an antigen when it recognizes its target antigen within a complex mixture of proteins and/or macromolecules. Typically, the antibody is capable of specifically interacting with and/or binding to its target but does not essentially bind to another epitope or antigen. Antibodies are said to "bind to the same epitope" if the antibodies cross-compete so that only one antibody can bind to the epitope at a given point of time, i.e. one antibody prevents the binding or modulating effect of the other.

Typically, binding that is considered specific may also have a high affinity, e.g. when the binding affinity is higher than $10^{-6}$ M (in terms of $K_d$). In particular, the binding affinity may be about $10^{-8}$ to $10^{-11}$ M ($K_d$), or of about $10^{-9}$ to $10^{-11}$ M or even higher. Thus, antibody molecules with an affinity in the picomolar range (with a $K_d$ of $9.9 \times 10^{-10}$ M to $10^{-12}$ M) are also encompassed in the present invention. If necessary, nonspecific binding of a binding site can be reduced without substantially affecting specific binding by varying the binding conditions.

An antibody according to the invention may be an isolated antibody molecule. The term "isolated antibody molecule" as used herein refers to an antibody molecule that has been identified and separated and/or recovered from a component of its natural environment. Contaminant components of its natural environment are matter that would interfere with uses for the antibody, and may include enzymes, hormones, and other proteinaceous or non-proteinaceous solutes. In some embodiments the antibody molecule is purified to greater than 95% by weight of antibody as determined by the Lowry method, such as more than 99% by weight. In some embodiments the antibody molecule is purified to a degree sufficient to obtain at least 15 residues of N-terminal or internal amino acid sequence by use of a spinning cup sequenator. In some embodiments the antibody is purified to homogeneity as judged by SDS-PAGE under reducing or non-reducing conditions using Coomassie blue or, preferably, silver stain. An isolated antibody molecule may in some embodiments be present within foreign host cells with one or more component(s) of the antibody's natural environment not being present. Typically an isolated antibody is prepared by at least one purification step.

Unless otherwise indicated CDRs sequences of the disclosure follow the definition by AbM used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Other standards for defining CDRs exist as well, such as the definition according to Maass 2007 (Journal of Immunological Methods 324 (2007) 13-25). Another standard is the definition according to Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia (see, e.g., Chothia, et al. (1992); J. Mol. Biol. 227:799-817; and Tomlinson et al. (1995) EMBO J. 14:4628-4638). It is understood that embodiments described with respect to the CDR definition of AbM, can alternatively be implemented using similar described relationships such as with respect to Maass, Kabat, or Chothia definition.

The valence of an antibody is generally an expression of the number of antigen-binding sites for one molecule of any given antibody or the number of antibody-binding sites for any given antigen. Most antibody molecules, and those belonging to the IgG, IgA, IgD and IgE immunoglobulin classes, have two antigen-binding sites per molecule. In general, a monovalent antibody comprises a single antigen binding site. Examples for a monovalent antibody are a single domain antibody, a VHH domain, a single Fab fragment, a Fv fragment, a scFv fragment, or a single VH or VL domain.

The terms "Fab", "Fab region", "Fab portion" or "Fab fragment" are understood to define a polypeptide that includes a $V_H$, a $C_H 1$, a $V_L$, and a $C_L$ immunoglobulin domain. Fab may refer to this region in isolation, or this region in the context of an antibody molecule according to the invention, as well as a full-length immunoglobulin or immunoglobulin fragment. Typically a Fab region contains an entire light chain of an antibody. A Fab region can be taken to define "an arm" of an immunoglobulin molecule. It contains the epitope-binding portion of that Ig. The Fab region of a naturally occurring immunoglobulin can be obtained as a proteolytic fragment by a partial papain-digestion. A "F(ab')$_2$ portion" is the proteolytic fragment of a partially pepsin-digested immunoglobulin. A "Fab' portion" is the product resulting from reducing the disulfide bonds of an F(ab')$_2$ portion. As used herein the terms "Fab", "Fab region", "Fab portion" or "Fab fragment" may further include a hinge region that defines the C-terminal end of the antibody arm (cf. above). This hinge region corresponds to the hinge region found C-terminally of the $C_H1$ domain within a full length immunoglobulin at which the arms of the antibody molecule can be taken to define a Y. The term hinge region is used in the art because an immunoglobulin has some flexibility at this region.

An "Fv" or "Fv fragment" consists of only the $V_L$ and $V_H$ domains of a "single arm" of an immunoglobulin. Thus an "Fv" is the minimum antibody fragment which contains a complete antigen-recognition and binding site. A "two-chain" Fv fragment consists of a dimer of one heavy- and one light-chain variable domain in tight, non-covalent association. A single-chain Fv species (scFv) includes a $V_H$ and a $V_L$ domain of an immunoglobulin, with these domains being present in a single polypeptide chain in which they are covalently linked to each other by a flexible peptide linker. Typically, in a scFv fragment the variable domains of the light and heavy chain associate in a dimeric structure analogous to that in a two-chain Fv species. In single chain Fv fragments, it is possible to either have the variable domain of the light chain arranged at the N-terminus of the single polypeptide chain, followed by the linker and the variable domain of the heavy chain arranged at the C-terminus of the polypeptide chain or vice versa, having the variable domain of the heavy chain arranged on the N-terminus and the variable domain of the light chain at the C-terminus with the peptide linker arranged in between. The peptide linker can be any flexible linker known in the art, for example, made from glycine and serine residues. It is also possible to additionally stabilize the domain association between the $V_H$ and the $V_L$ domain by introducing disulfide bonds into conserved framework regions (see Reiter et al. Stabilization of the Fv fragments in recombinant immunotoxins by disulfide bonds engineered into conserved framework regions, Biochemistry 1994, 33, 6551-5459). Such scFv fragments are also known as disulfide-stabilized scFv fragments (ds-scFv).

The term "Fc region" or "Fc fragment" is used herein to define a C-terminal region of an immunoglobulin heavy chain, including native-sequence Fc regions and variant Fc regions. The Fc part mediates the effector function of antibodies, e.g. the activation of the complement system and of Fc-receptor bearing immune effector cells, such as NK cells. In human IgG molecules, the Fc region is generated by papain cleavage N-terminal to Cys226. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody molecule, or by recombinantly engineering the nucleic acid encoding a heavy chain of the antibody molecule. Accordingly, a composition of intact antibodies may include antibody populations with all K447 residues removed, antibody populations with no K447 residues removed, and antibody populations having a mixture of antibodies with and without the K447 residue. Suitable native-sequence Fc regions for use in the antibodies of the invention include mammalian, e.g. human or murine, IgG1, IgG2 (IgG2A, IgG2B), IgG3 and IgG4. The Fc region contains two or three constant domains, depending on the class of the antibody. In embodiments where the immunoglobulin is an IgG the Fc region has a $C_H2$ and a $C_H3$ domain.

An antibody according to the invention may be produced using any known and well-established expression system and recombinant cell culturing technology, for example, by expression in bacterial hosts (prokaryotic systems), or eukaryotic systems such as yeasts, fungi, insect cells or mammalian cells. An antibody molecule of the present invention may be produced in transgenic organisms such as a goat or a plant. An antibody may also be produced by chemical synthesis.

An antibody of the invention may comprise the CDR1 sequence GVTISALNAMAMG (SEQ ID NO: 115) or a sequence having 1 or 2 mutations relative to said sequence, the CDR2 sequence AVSERGNAM (SEQ ID NO: 116) or a sequence having 1 or 2 mutations relative to said sequence, and the CDR3 sequence LEDRVDSFHDY (SEQ ID NO: 117) or a sequence having 1 or 2 mutations relative to said sequence. An antibody of the invention may comprise the CDR1 sequence GVTISALNAMAMG (SEQ ID NO: 118) or a sequence having 1 or 2 mutations relative to said sequence, the CDR2 sequence AVSSRGNAM (SEQ ID NO: 119) or a sequence having 1 or 2 mutations relative to said sequence, and the CDR3 sequence. An antibody of the invention may comprise the CDR1 sequence GVTVSAL-NAMAMG (SEQ ID NO: 121) or a sequence having 1 or 2 mutations relative to said sequence, the CDR2 sequence AVSERGNAM (SEQ ID NO: 122) or a sequence having 1 or 2 mutations relative to said sequence, and the CDR3 sequence LEDRVDSFHDY (SEQ ID NO: 123) or a sequence having 1 or 2 mutations relative to said sequence. It is understood that such an antibody preferably comprises or consists of a camelid VHH domain, such as a single domain antibody, or an antibody naturally devoid of light chains. It is further understood that an antibody in which 1 or 2 mutations have been introduced to one, two, or all three of the CDR sequences is still capable of specifically binding the peptide comprised in the fusion protein of the invention, in particular a peptide having the core structure of SEQ ID NO: 3, such as a peptide of any one of SEQ ID NOs: 05-07. In such an antibody of the invention, the E or S at amino acid position 4 of CDR2 may be mutated to G, A, L, I, S, T, V, C, M, D, N, E, Q, F, Y, H, W, K, R, or P, preferably to D, N, or H. Such an antibody of the invention may comprise the FR1 sequence EVQLX$_1$ESGGGLVX$_2$PGGSX$_3$RLSCTAS, wherein X$_1$ is Q, V, E, or L, X$_2$ is Q or P, and X$_3$ is L or M (SEQ ID NO: 124), or a sequence having at least 80%, 85%, 90%, or 95% sequence identity to said sequence. Such an antibody of the invention may comprise the FR1 sequence EVQLQESGGGLVQPGGSLRLSCTAS (SEQ ID NO: 125) or a sequence having at least 80%, 85%, 90%, or 95% sequence identity to said sequence. Such an antibody of the invention may comprise the FR2 sequence WYRQX$_1$PGEX$_2$RVMVA, wherein X$_1$ is A or R and X$_2$ is R or E (SEQ ID NO: 126) or a sequence having at least 80%, 85%, 90%, or 95% sequence identity to said sequence. Such an antibody of the invention may comprise the FR2 sequence WYRQAPGERRVMVA (SEQ ID NO: 127) or a sequence having at least 80%, 85%, 90%, or 95% sequence identity to said sequence.

Such an antibody of the invention may comprise the FR2 sequence WYRQAPGEERVMVA (SEQ ID NO: 128) or a sequence having at least 80%, 85%, 90%, or 95% sequence identity to said sequence. Such an antibody of the invention may comprise the FR3 sequence YRESVQGRFTVTRDFTNKMVSLQMDNLX$_1$PEDX$_2$AVYYCHV, wherein X1 is K or Q and X$_2$ is T or M (SEQ ID NO: 129) or a sequence having at least 80%, 85%, 90%, or 95% sequence identity to said sequence. Such an antibody of the invention may comprise the FR3 sequence YRESVQGRFTVTRDFTNKMVSLQMDNLKPED-TAVYYCHV (SEQ ID NO: 130) or a sequence having at least 80%, 85%, 90%, or 95% sequence identity to said sequence. Such an antibody of the invention may comprise the FR4 sequence WGQGX$_1$QVTVSS, wherein X$_1$ is T or I (SEQ ID NO: 131) or a sequence having at least 80%, 85%, 90%, or 95% sequence identity to said sequence. Such an antibody of the invention may comprise the FR4 sequence WGQGTQVTVSS (SEQ ID NO: 132) or a sequence having at least 80%, 85%, 90%, or 95% sequence identity to said sequence.

An antibody of the invention may comprise or consist of the VHH sequence selected from the group consisting of:

(a)
(SEQ ID NO: 133)
EVQLQESGGGLVQPGGSLRLSCTASGVTISALNAMAMGWYRQAPGERRVM

VAAVSERGNAMYRESVQGRFTVTRDFTNKMVSLQMDNLKPEDTAVYYCHV

LEDRVDSFHDYWGQGTQVTVSS;

(b)
(SEQ ID NO: 134)
EVQLQESGGGLVQPGGSLRLSCTASGVTISALNAMAMGWYRQAPGEERVM

VAAVSSRGNAMYRESVQGRFTVTRDFTNKMVSLQMDNLKPEDTAVYYCHV

LEDRVDSFHDYWGQGTQVTVSS;

(c)
(SEQ ID NO: 135)
EVQLQESGGGLVQPGGSLRLSCTASGVTISALNAMAMGWYRQAPGEERVM

VAAVSERGNAMYRESVQGRFTVTRDFTNKMVSLQMDNLKPEDTAVYYCHV

LEDRVDSFHDYWGQGTQVTVSS;

(d)
(SEQ ID NO: 136)
EVQLQESGGGLVQPGGSLRLSCTASGVTISALNAMAMGWYRQAPGERRVM

VAAVSSRGNAMYRESVQGRFTVTRDFTNKMVSLQMDNLKPEDTAVYYCHV

LEDRVDSFHDYWGQGTQVTVSS;

(e)
(SEQ ID NO: 137)
EVQLVESGGGLVPPGGSMRLSCTASGVTVSALNAMAMGWYRQRPGERRVM

VAAVSERGNAMYRESVQGRFTVTRDFTNKMVSLQMDNLQPEDMAVYYCHV

LEDRVDSFHDYWGQGIQVTVSS;

(f)
(SEQ ID NO: 138)
EVQLVESGGGLVPPGGSMRLSCTAPGVTVSALNAMAMGWYRQRPGERRVM

VAAVSERGNAMYRESVQGRFTVTRDFTNKMVSLQMDNLQPEDMAVYYCHV

LEDRVDSFHDYWGQGIQVTVSS;

(g)
(SEQ ID NO: 139)
EVQLVESGGGVVQPGGSLRLSCTASGVTISALNAMAMGWYRQAPGERRVM

VAAVSERGNAMYRESVQGRFTVTRDFTNKMVSLQMDNLKPEDTAVYYCHV

LEDRVDSFHDYWGQGTQVTVSS;

(h)
(SEQ ID NO: 140)
EVQLVESGGGLVQPGGSLRLSCTASGVTISALNAMAMGWYRQAPGERRVM

VAAVSERGNAMYRESVQGRFTVTRDFTNKMVSLQMDNLKPEDTAVYYCHV

LEDRVDSFHDYWGQGTQVTVSS;

(i)
(SEQ ID NO: 141)
EVQLEESGGGLVQPGGSLRLSCTASGVTISALNAMAMGWYRQAPGERRVM

VAAVSERGNAMYRESVQGRFTVTRDFTNKMVSLQMDNLKPEDTAVYYCHV

LEDRVDSFHDYWGQGTQVTVSS;
and (j)
(SEQ ID NO: 142)
EVQLLESGGGLVQPGGSLRLSCTASGVTISALNAMAMGWYRQAPGERRVM

VAAVSERGNAMYRESVQGRFTVTRDFTNKMVSLQMDNLKPEDTAVYYCHV

LEDRVDSFHDYWGQGTQVTVSS;

(k)
(SEQ ID NO: 175)
EVQLQESGGGLVQPGGSLRLSCTASGVTISALNAMAMGWYRQAPGERRVM

VAAVSDRGNAMYRESVQGRFTVTRDFTNKMVSLQMDNLKPEDTAVYYCHV

LEDRVDSFHDYWGQGTQVTVSS;

(l)
(SEQ ID NO: 176)
EVQLQESGGGLVQPGGSLRLSCTASGVTISALNAMAMGWYRQAPGERRVM

VAAVSNRGNAMYRESVQGRFTVTRDFTNKMVSLQMDNLKPEDTAVYYCHV

LEDRVDSFHDYWGQGTQVTVSS;

(m)
(SEQ ID NO: 177)
EVQLQESGGGLVQPGGSLRLSCTASGVTISALNAMAMGWYRQAPGERRVM

VAAVSHRGNAMYRESVQGRFTVTRDFTNKMVSLQMDNLKPEDTAVYYCHV

LEDRVDSFHDYWGQGTQVTVSS or a sequence having at least 80%, 85%, 90%, or 95% sequence identity to any one of said sequences.

An antibody of the invention may comprise the CDR1 sequence GTMSAINALN (SEQ ID NO: 143) or a sequence having 1 or 2 mutations relative to said sequence, the CDR2 sequence AITDNGNAH (SEQ ID NO: 144) or a sequence having 1 or 2 mutations relative to said sequence, and the CDR3 sequence LEEEKLGVWVDY (SEQ ID NO: 145) or a sequence having 1 or 2 mutations relative to said sequence. An antibody of the invention may comprise the CDR1 sequence GTMSAINALN (SEQ ID NO: 146) or a sequence having 1 or 2 mutations relative to said sequence, the CDR2 sequence AITDNGNAH (SEQ ID NO: 147) or a sequence having 1 or 2 mutations relative to said sequence, and the CDR3 sequence LEEKLGAWVDY (SEQ ID NO: 148) or a sequence having 1 or 2 mutations relative to said sequence. An antibody of the invention may comprise the CDR1 sequence GTMSAINALN (SEQ ID NO: 149) or a sequence having 1 or 2 mutations relative to said sequence, the CDR2 sequence AITDNGNAH (SEQ ID NO: 150) or a sequence having 1 or 2 mutations relative to said sequence, and the CDR3 sequence LEKEKLGVWVDY (SEQ ID NO: 151) or a sequence having 1 or 2 mutations relative to said sequence. It is understood that such an antibody preferably comprises or consists of a camelid VHH domain, such as a single domain antibody, or an antibody naturally devoid of light chains. It is further understood that an antibody in which 1 or 2 mutations have been introduced to one, two, or all three of the CDR sequences is still capable of specifically binding the peptide comprised in the fusion protein of the invention, in particular a peptide having the core structure of SEQ ID NO: 3, such as a peptide of any one of SEQ ID NOs: 05-07. Such an antibody of the invention may comprise the FR1 sequence EVQLX1ESGGGLVQPGGSLTLSCAAS, wherein X1 is V or L (SEQ ID NO: 152) or a sequence having at least 80%, 85%, 90%, or 95% sequence identity to said sequence. Such an antibody of the invention may comprise the FR2 sequence WYRQX1PGKERKMVA, wherein X1 is P or A (SEQ ID NO: 153) or a sequence having at least 80%, 85%, 90%, or 95% sequence identity to said sequence. Such an antibody of the invention may comprise the FR3 sequence YADSVKGRFTISRDNARNMVFLQMNSLX1PDDTAV YYCHY, wherein X1 is K or E (SEQ ID NO: 154) or a sequence having at least 80%, 85%, 90%, or 95% sequence identity to said sequence. Such an antibody of the invention may comprise the FR4 sequence WGQGTQVTVSS (SEQ ID NO: 155) or a sequence having at least 80%, 85%, 90%, or 95% sequence identity to said sequence.

An antibody of the invention may comprise or consist of the VHH sequence selected from the group consisting of:

(a)
(SEQ ID NO: 156)
EVQLVESGGGLVQPGGSLTLSCAASGTMSAINALNWYRQPPGKERKMVAA

ITDNGNAHYADSVKGRFTISRDNARNMVFLQMNSLKPDDTAVYYCHYLEE

EKLGVWVDYWGQGTQVTVSS;

(b)
(SEQ ID NO: 157)
EVQLLESGGGLVQPGGSLTLSCAASGTMSAINALNWYRQAPGKERKMVAA

ITDNGNAHYADSVKGRFTISRDNARNMVFLQMNSLEPDDTAVYYCHYLEE

KLGAWVDYWGQGTQVTVSS;
and (c)
(SEQ ID NO: 158)
EVQLVESGGGLVQPGGSLTLSCAASGTMSAINALNWYRQPPGKERKMVAA

ITDNGNAHYADSVKGRFTISRDNARNMVFLQMNSLKPDDTAVYYCHYLEK

EKLGVWVDYWGQGTQVTVSS;

or a sequence having at least 80%, 85%, 90%, or 95% sequence identity to any one of said sequences.

The antibody of the invention may be conjugated to a detectable label. In general, such a "detectable label" may be any appropriate chemical substance or enzyme, which directly or indirectly generates a detectable compound or signal in a chemical, physical, optical, or enzymatic reaction. For example, a fluorescent or radioactive label can be conjugated to the antibody to generate fluorescence or X-rays as detectable signal. Alkaline phosphatase, horseradish peroxidase and β-galactosidase are examples of enzyme labels (and at the same time optical labels), which catalyze the formation of chromogenic reaction products. In a preferred embodiment, the detectable label refers to detectable entities that can be used for the detection of the target of interest in microscopy, immunohistochemistry or flow cytometry. Preferably, the label does not negatively affect the characteristics of the antibody to which the label is conjugated. Examples of labels are fluorescent labels such as phycoerythrin, allophycocyanin (APC), Brilliant Violet 421, Alexa Fluor 488, coumarin or rhodamines to name only a few. There are many types of detectable labels, including a fluorescent label, a chromophore label, an isotope label, or a metal label, with a fluorescent label being preferred. The presence of a fusion protein of the invention may be detected by contacting the fusion protein with an antibody of the invention conjugated to a detectable label and detecting the signal of the detectable label. For a fluorescent label, this means detection of emitted light upon excitation of the fluorescent label. Non-exhaustive examples for suitable fluorescent labels are "green" emitters (Atto488, Alexa488, Cy2, etc.), "orange" emitters (Atto542, alexa555, Cy3, etc.), "Red-far-Red" emitters (Alexa633, Atto 647N, Cy5, etc.), infrared emitters (Atto700, LiCor IRDye700, LiCor IRDye800, etc.), ultra-violet absorbing fluorescent dyes (Atto390 or Alexa405). A fluorescent label may also be a fluorescent protein, such as GFP, eGFP, YFP, RFP, CFP, BFP, mCherry, or near-infrared fluorescent proteins. Non-exhaustive examples for a suitable chromophore label are alkaline phosphatase or peroxidase exposed to TMB (3,3', 5,5' tetramethylbenzidine), DAB (3,3',4,4' diaminobenzidine), and 4CN (4-chloro-1-naphthol). ABTS (2,2'-azino-di [3-ethyl-benzthiazoline]sulfonate), OPD (o-phenylenediamine), and to BCIP/NBT (5-bromo-4-chloro-3-indolyl-phosphate/nitroblue tetrazolium). Non-exhaustive examples for isotope labels are 13C, 15N, 19F, 27A1, 11B, 1271 or different Lanthanides isotopes. Non-exhaustive examples for a metal label are Au, Pd, Pb, Pt Ag, Hg and Os. The label may be a direct label, i.e. a label that is directly detectable. Alternatively, the label may be an indirect label, i.e. a label which is an affinity tag (or epitope tag) that can be specifically bound by another specific binding partner that is conjugated to another detectable label, such as a fluorescent or chromophore label. Examples of suitable epitope tags include, but are not limited to, FLAG-tag (sequence: DYKDDDDK, SEQ ID NO: 160), Strep-tag (sequence: WSHPQFEK, SEQ ID NO: 178), Myc-tag (sequence: EQKLISEEDL, SEQ ID NO: 161), HA-tag (sequence: YPYDVPDYA, SEQ ID NO: 162), VSV-G-tag (sequence: YTDIEMNRLGK, SEQ ID NO: 163), HSV-tag (sequence: QPELAPEDPED, SEQ ID NO: 164), V5-tag (sequence: GKPIPNPLLGLDST, SEQ ID NO: 165), SPOT-tag (sequence: PDRVRAVSHWSS, SEQ ID NO: 166), BC2 tag (sequence: PDRKAAVSHWQQ, SEQ ID NO: 167), and EPEA tag (sequence: EPEA, SEQ ID NO: 168). The antigen may also be a protein, for example, glutathione-S-transferase (GST), maltose binding protein (MBP), chitin binding protein (CBP) or thioredoxin as an antigen. The detectable label may further be a nucleic acid, such as an oligonucleotide having a recognition sequence. Such a recognition sequence may be a random sequence. This random sequence may be barcode sequence that has been incorporated into the nucleic acid molecules and can be used to identify the target molecule that has been conjugated with said nucleic acid. An "antibody of the invention may be conjugated to a detectable label" may also mean that the antibody itself is the detectable label. This may imply that the antibody is an affinity target that can be specifically recognized by another specific binding partner that specifically binds to the antibody. For example, such a specific binding partner may be an antibody that specifically recognizes camelid VHH domains. Such a specific binding partner may further be conjugated to a detectable label, such as a fluorescent label.

An antibody of the invention may be conjugated to a solid support. The term "solid support" or in the context of the present invention refers to any type of carrier material that can be used for immobilization of affinity ligands such as antibodies or parts thereof and it can refer to material in particulate (e.g. beads or granules, generally used in extraction columns) or in sheet form (e.g. membranes or filters, glass or plastic slides, microtiter assay plates, dipstick, capillary fill devices or such like) which can be flat, pleated, or hollow fibers or tubes. Suitable and well-known matrices without being exhaustive: are silica (porous amorphous silica), agarose or polyacrylamide supports, or macroporous polymers. Examples include dextran, collagen, polystyrene, polypropylene, polyvinylchloride, polyacrylamide, methacrylate, celluloses, calcium alginate, controlled pore glass, aluminum, titanium and porous ceramics, synthetic polymers and co-polymers, latex, silica, agarose, metal, glass, and carbon. Alternatively, the solid surface may comprise part of a mass dependent sensor, for example, a surface plasmon resonance detector. Conveniently, an array comprising a plurality of individual affinity ligand such as antibodies or antibody fragments, which are capable of specifically binding the epitope tag of the present invention, bound or immobilized to a solid surface is provided. This array can be used to capture tagged polypeptides comprised in a solution as soon the solution is brought in contact with the immobilized affinity ligand such as antibodies or antibody fragments. A solid support can also be a magnetic bead or polymeric bead or a chromatographic stationary phase.

An antibody of the invention may be in complex with an epitope it specifically binds to. Such an epitope may be a peptide that is comprised in the fusion protein of the invention. The antibody of the invention may thus be in complex with a fusion protein of the invention. The present invention therefore encompasses a fusion protein comprising an peptide that the antibody of the invention specifically binds to.

The present invention also relates to a complex comprising (a) fusion protein and (b) an antibody, wherein the fusion protein is a fusion protein of the invention and/or wherein the antibody is an antibody of the invention.

The present invention also relates to a nucleic acid molecule comprising a sequence encoding a fusion protein of the invention as described herein or an antibody of the invention as described herein. The nucleic acid molecule may be a DNA or an RNA molecule. The nucleic acid molecules of the invention may be part of a vector or any other kind of cloning or expression vehicle, such as a plasmid, a phagemid, a phage, a baculovirus, a cosmid or an artificial chromosome. The nucleic acid molecule, may allow expression of the fusion protein or antibody. It may include sequence elements that contain information regarding to transcriptional and/or translational regulation, and such sequences may be "operably linked" to the nucleotide sequence encoding the protein. An operable linkage is a linkage in which the regulatory sequence elements and the sequence to be expressed are connected in a way that enables gene expression. The precise nature of the regulatory regions necessary for gene expression may vary among species, but in general these regions include a promoter, which, in prokaryotes, contains both the promoter per se, i.e., DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native protein to a specific compartment of a host cell.

Such a vehicle described herein may include, aside from the regulatory sequences described herein and a nucleic acid sequence encoding a peptide or protein described herein, replication and control sequences derived from a species compatible with a host cell that is used for expression as well as selection markers conferring a selectable phenotype on transformed or transfected cells. Large numbers of suitable cloning vectors are known in the art and are commercially available. Accordingly, the present invention also relates to a vector comprising the nucleic acid molecule of the invention.

Cloning or expression of nucleic acid molecule or the vector of the invention can be conducted at least partially in vivo, using host cells transformed with the nucleic acid or vector, or to which the nucleic acid molecule or vector has been transferred by other means including transduction or transfection. Transfer of DNA can be performed using standard techniques. Thus, the disclosure is also directed to a host cell containing a nucleic acid molecule or a vector as disclosed herein.

A peptide of the invention is useful for several applications. These cellular applications may have in common that the peptide is used as an epitope tag. Non-limiting examples for applications, in which the peptide is useful include, but are not limited to, detection, immobilization, isolation, or purification of the fusion protein of the invention. Similarly also an antibody of the invention may be used for all applications that includes specific binding of an epitope tag. An antibody of the invention may be used for example for detection, immobilization, isolation, or purification of a fusion protein of the invention.

The present invention also relates to a method of detecting a fusion protein of the invention. Detection can be optical detection, isotopic detection, or detection by electron microscopy. The method comprises contacting the fusion protein with an antibody of the invention, preferably under conditions allowing the formation of a complex between the peptide comprised in the fusion protein and the antibody. The antibody of the invention preferably carries a detectable label as defined herein. Where the detectable label is a fluorescent label, chromophore label, isotope label, or metal label attached to it, it is understood that the antibody preferably has a defined number of labels attached to it. The method may comprise the step of detecting the detectable label. The method may comprise expressing the fusion protein of the invention prior to contacting the fusion protein with the antibody.

The term "detection" as used herein includes both, direct detection of a target (i.e. wherein the target is detected by a signal deriving from a target) and indirect detection of a target (i.e. wherein the target is detected by a signal that does not directly derive from the target, e.g. by a signal that derives from another molecule attached to the target). The term "detection" as used herein further includes both, qualitative and quantitative detection. The term "detection" may refer to determination of the presence, subcellular localization, or amount of a given molecule or structure, such as the fusion protein of the invention. The fusion protein to be detected, located and/or quantified can be detected at its intracellular location in a host cell, for example in the cell nucleus, in cell membranes or another cell compartment. The fusion protein to be detected, and/or to be quantified can also be detected in a solution comprising the tagged polypeptide or protein, for example a cell lysate obtained from a host cell or a tissue comprising the host cell.

The term "optical", as used herein, preferably refers to visible light but is generally not limited to it. The term may also refer to infrared, ultraviolet and other regions of the electromagnetic spectrum.

As used herein, "isotopic detection" relates to the detection of a molecule in which one or more atoms have been replaced (i.e. "labeled") with another isotope that commonly has a detectable variation. The isotopic label can be detected by multiple means, such as their mass (e.g. by mass spectrometry, matrix-assisted laser desorption/ionization (MALDI), desorption electrospray ionization (DESI), laser-ablation inductively coupled plasma mass spectrometry (LA-ICP-MS), or secondary-ion mass spectrometry (SIMS), vibrational mode (e.g. by infrared spectroscopy), gyromagnetic ratios (e.g. by nuclear magnetic resonance), or radioactive decay (e.g. an ionization chamber or autoradiographs of gels).

Electron microscopy relates to a method of detection using an electron microscope. Types of electron microscopes include transmission electron microscope (TEM), scanning electron microscope (SEM), reflection electron microscope (REM), scanning transmission electron microscope (STEM), and Correlative Light and Electron Microscopy (CLEM).

In a first step of a detection method, an antibody specifically binding the peptide comprised in the fusion protein of the present invention may be contacted with a sample comprising the fusion protein. The sample may be a host cell, a tissue, a solution comprising cell lysate of a host cell or any other sample that comprises the fusion protein, such as a supernatant, as obtained after centrifugation of a liquid comprising the host cell, wherein the host cell is capable of secreting the polypeptide of interest into the liquid or another specimen like a body fluid.

This contacting step is preferably carried out at conditions that allow specific interaction of the antibody and the peptide it specifically binds to. Such conditions are well known to the person of skill in the art. Washing steps typically follow the contacting step of an antibody to its antigen, and the skilled person knows how and when to apply said washing steps. Upon contacting with the sample, the antibody will specifically interact with the fusion protein. This interaction can be detected, monitored and quantified by measuring or observing the reporter signal obtained from the detectable label. For example, if the detectable label is a fluorescent label, fluorescence can be measured and observed upon excitation.

If the detectable label is an affinity tag (or epitope tag) that can be specifically bound by another specific binding partner that is conjugated to another detectable label, such as a fluorescent or chromophore label. In such a case, detection of the detectable label attached to the antibody of the invention may be conducted by contacting the antibody with a specific binding partner that specifically binds to the detectable label conjugated to the antibody of the invention. The specific binding partner may be labeled with a further detectable label that can preferably be distinguished from the first detectable label, such as a fluorescent or chromophore label. The specific binding partner may however be a structure, which can be recognized by another specific (labeled) binding reagent. For example, the specific binding partner that binds to the detectable label conjugated to the antibody of the invention may be a (primary) antibody, which may be specifically recognized by a (secondary) antibody, which carries a detectable label that is preferably distinguishable from the first detectable label, such as a fluorescent label. The method of detection the fusion protein of the invention may thus comprise the step of contacting the fusion protein and the antibody with a specific binding partner for the detectable label comprised in the antibody. Where a second detectable label is present, the method may comprise the step of detecting the first and/or the second detectable label.

According to methods where the detectable label conjugated to the antibody of the invention is an affinity tag, the method of detecting the fusion protein may comprise, in a first step, contacting the antibody of the invention with a sample comprising or suspected to comprise the fusion protein of the invention. In a second step, a (secondary) specific binding partner can be contacted with the sample comprising the fusion protein bound to the antibody of the invention. In cases where the (secondary) specific binding partner is not conjugated to a detectable label or where the detectable label is an affinity tag, the method may further comprise the step of contacting a further specific binding partner, such as a further antibody that specifically binds to the (secondary) specific binding partner or its detectable label. The further specific binding partner may comprise a detectable label, such as a fluorescent label that can be used for detection of the fusion protein. Presence, amount and/or localization of the tagged polypeptide or protein can be detected or determined by measuring or observing a reporter signal obtained from a detectable label comprised in the (secondary) specific binding partner or further specific binding partner.

An advantage of a two-step detection method using two types of binding partners is that the tag specific interaction is separated from the actual detection step. This allows that the antibody of the invention remains unchanged, as it does not need to comprise an additional detectable moiety. This may in some cases enhance its specificity or affinity compared to an antibody comprising an additional detectable label, as the detectable label could in some cases influence the interaction of the peptide comprised in the fusion protein of the invention and the antibody of the invention. Thus, the reliability and efficiency of the detection method could be enhanced in some cases. Furthermore, using the antibody of the invention simply as a capture antibody and not as a capture and detection antibody, allows separation of the capture and the detection steps if only presence and amount of the fusion protein is to be determined. Therefore, the first step using the antibody of the invention could be followed by an isolation or enrichment step, yielding the captured fusion protein of interest. The detection step could then be carried out on the isolated and/or enriched fusion protein, leading to an enhanced reliability of the obtained quantification and an easier handling of the detection step.

Suitable biophysical or biomolecular detection methods for qualitatively detecting the epitope tag/antibody interaction comprise any suitable method known in the art. Such methods include, without being limited thereto, methods as applied for qualitative or quantitative assays, e.g. for Enzyme-linked Immunosorbent Assay (ELISA), ELISPOT assay, Western Blot, or immunoassays. Such methods comprise e.g. optical, radioactive or chromatographic methods, preferably when using any of the above labels, markers or linkers, more preferably fluorescence detection methods, radioactivity detection methods, Coomassie-Blue staining, silver staining or other protein staining methods, electron microscopy methods, methods for staining tissue sections by immunohistochemistry or by direct or indirect immunofluorescence, etc. Such methods may be applied either with the antibody or may involve the use of further tools, e.g. the use of a secondary binding partner, specifically binding to a part of the fusion protein, the antibody, or the complex.

In some embodiments, the subcellular localization of the tagged polypeptide or protein of interest can also be determined. For example, distinct subcellular structures such as the intermediate filamentous network or an essential part of the replication machinery can be visualized and monitored.

Detection of the fusion protein can also be carried out using an antibody of the invention that is an intrabody. An "intrabody" as used herein refers to an antibody that is located within a cell to bind to an intracellular protein. Due to the lack of a reliable mechanism for bringing an antibody into a living cell from the extracellular environment, this typically requires the expression of the antibody within the target cell. After expression, the antibody may remain in the cytoplasm, or it may have a nuclear localization signal, or it may undergo co-translational translocation across the membrane into the lumen of the endoplasmic reticulum, provided that it is retained in that compartment through a KDEL sequence. A detectable label conjugated to an intrabody may be a proteinaceous label, which can be expressed as fusion protein with the intrabody. Ideally, such a label may be optically detectable, such as by fluorescence. The detectable label may thus be a fluorescent protein.

The present invention also relates to a method of isolating the fusion protein of the invention. Such a method comprises contacting the fusion protein with an antibody of the invention, preferably under conditions allowing formation of a complex between the antibody and the peptide comprised in the fusion protein. Thereby, binding of the fusion protein and the antibody is enabled. This contacting step, also referred to as capture step, may be conducted by contacting a sample, for example a solution, comprising the fusion protein with the antibody.

The sample to be contacted with the tag specific antibody can be any type of sample comprising a fusion protein of the invention and can be processed to separate the polypeptide. Preferably the sample is a solution, for example a lysate of a host cell or a body fluid, comprising the fusion protein of the invention, or a supernatant, such as a supernatant obtainable by centrifugation of a liquid comprising a host cell comprising or capable of expressing fusion protein of the invention, wherein the host cell is capable of secreting or otherwise transporting the fusion protein of the invention to the liquid.

The antibody used in the method of the present invention for isolation and/or purification can be used in solution or immobilized. To immobilize the antibody, the antibody can be bound to a sample carrier, solid support, or matrix. This immobilization step can occur prior to or after the binding of the antibody to the peptide comprised in the fusion protein. Methods for immobilizing antibodies and parts thereof are well-known to the person skilled in the art and any method that allows immobilization without impairing binding properties can be used.

If the antibody of the present invention is not immobilized to a solid support, then the method may comprise a further step of isolating the complex, for example by using a specific binding partner for the complex, such as a secondary antibody that is specific for example for the complex or for the antibody or for a detectable label, such as an affinity tag, that is conjugated to the antibody. The secondary binding partner can be in solution or can be immobilized or immobilizable to a solid support.

In an optional further step following the capture step, the solid support comprising the immobilized antibody bound to the fusion protein is washed to remove unbound and unspecifically bound constituents.

Optionally, in a further step, the fusion protein can be eluted to obtain the isolated fusion protein. Elution of the fusion protein bound to the immobilized antibody can be achieved by methods known in the art. For example, the fusion protein can be eluted by competitive elution with an epitope peptide as described herein in isolated form. This isolated epitope peptide will then be in competition with the fusion protein to bind the immobilized tag-specific antibody. If the isolated peptide is added in surplus concentration, the reaction balance of the binding will be shifted to the binding of the immobilized antibody with the isolated epitope tag. This results in the release of the fusion protein. The epitope peptide used for elution may be the same epitope peptide that is comprised in the fusion protein. The epitope peptide used for elution may also be a different peptide than the epitope peptide comprised in the fusion protein. If the epitope peptide used for elution is a different one, it is preferred that the epitope peptide used for elution has a higher binding affinity to the antibody than the epitope peptide comprised in the fusion protein. Additional steps for further purifying the released polypeptide can optionally be added, such as method steps well-known to the skilled person.

The fusion protein may also remain immobilized to the solid support, such as (magnetic) beads, and processed further in downstream application such as mass spectrometry, without the elution step.

The fusion protein may comprise a linker with a cleavage site that can be cleaved with an appropriate means, for example a protease, to remove the peptide. Thereby the polypeptide of the fusion protein may be released from the immobilized antibody, and the polypeptide can be obtained in its native form. For this embodiment, the nucleic acid sequence encoding the fusion protein should not only comprise a sequence encoding the epitope tag but also a sequence encoding a linker with a breakable site, for example a cleavage site recognized by a protease. The release step by enzymatic cleave can replace or follow the elution step.

Where the fusion protein of the invention comprises an antibody moiety, the present invention also envisions a method of isolating the target of the antibody moiety of the invention. In principle, this method can be carried out as described above for the isolation of a fusion protein. The method may comprise the additional step of contacting the fusion protein with a specific target of the antibody moiety comprised in the fusion protein. This contacting step may be conducted prior to or after contacting the fusion protein with the antibody that binds to the peptide tag comprised in the fusion protein, with the latter alternative being preferred. In a preferred method, first the antibody specific for the peptide tag is immobilized on the solid support, and then the fusion protein is immobilized via binding to the antibody that is specific to the peptide tag, followed by binding the target of the antibody moiety of the fusion protein to the fusion protein. Elution can be carried out as described above. The specific target may be a cell. For example, a cell surface receptor on the cell, such as CD62L. The antibody moiety of the fusion protein may be specific to a structure on the cell, such as CD62L. The antibody moiety of the fusion protein may be a single domain antibody.

The present invention also envisions that detection and isolation of a fusion protein of the invention can be combined. Accordingly, the present invention envisions a method of detection and isolation of a fusion protein of the invention comprising a method of detection of the invention and a method of isolation and/or purification of the invention.

Combination of both methods may thus be carried out by using one antibody conjugated to a detectable label for detection, and another antibody conjugated to a solid support for isolation of the same fusion protein. Both antibodies may be any antibody of the invention. This combination may have the advantage that only one tagged fusion protein has to be generated and detection and isolation carried out with the same transgenic construct/cell. Sometimes, it may be desired that both antibodies have an identical sequence or at least an identical antigen-binding site. For example, both antibodies may comprise CDR 1-3 sequences set forth in SEQ ID NOs: 115-117 or may comprise the sequence set forth SEQ ID NO: 133 or a sequence having at least 80%, 85%, 90%, or 95% sequence identity to SEQ ID NO: 133. Sometimes, it may be desired that both antibodies have different sequences or different antigen-binding sites. Using different antibodies may have the advantage that tight binder, e.g, an antibody having a high affinity (e.g. about 1 pM to about 1 nM) to the peptide comprised in the fusion protein, can be used for detection, whereas a moderate binder, i.e. an antibody having moderate affinity (e.g. about 1 nM to about 500 nM) can be used for isolation of the fusion protein. For example, one of the antibodies may comprise CDR 1-3 sequences set forth in SEQ ID NOs: 115-117 or may comprise the sequence set forth SEQ ID NO: 133 or a sequence having at least 80%, 85%, 90%, or 95% sequence identity to SEQ ID NO: 133 while the other antibody may comprise CDR 1-3 sequences set forth in SEQ ID NOs: 118-120 or may comprise the sequence set forth SEQ ID NO: 134 or a sequence having at least 80%, 85%, 90%, or 95% sequence identity to SEQ ID NO: 134. The peptide comprised in the fusion protein may be a peptide having a core sequence of SEQ ID NO: 3 or 4 as described herein.

Combination of both methods can also be carried out by using the same antibody and two different peptides for detection and purification. This has the advantage, that only one antibody has to be produced which, depending on the application, can be conjugated to a detectable label or a solid support. When using two different peptides, it is preferred that the peptides have different binding affinity to the antibody. The peptide that is used for detection, may have a high binding affinity of e.g. about 1 pM to 1 nM, while the peptide that is used for isolation may have a moderate binding affinity of about 1 nM to 500 nM. Using peptides having different binding affinities may have the advantage that if a moderate affinity peptide is comprised in the fusion protein for isolation, a high(er) affinity peptide can be used for elution of the fusion protein. Accordingly, one peptide may be a peptide having a core sequence of SEQ ID NO: 3 or 4 as described herein, while the other peptide may be a peptide having a core sequence of SEQ ID NO: 31 or 32 as described herein. The antibody may be any antibody of the invention, e.g. the antibody may comprise CDR 1-3 sequences set forth in SEQ ID NOs: 115-117 or may comprise the sequence set forth SEQ ID NO: 133 or a sequence having at least 80%, 85%, 90%, or 95% sequence identity to SEQ ID NO: 133.

Combination of both methods can also be carried out by using two peptides and two antibodies. The fusion protein of interest may comprise a peptide having a high affinity to a given antibody. For example, the peptide may be a peptide having a core sequence of SEQ ID NO: 3 or 4 as described herein. The antibody for detection may comprise CDR 1-3 sequences set forth in SEQ ID NOs: 115-117 or may comprise the sequence set forth SEQ ID NO: 133 or a sequence having at least 80%, 85%, 90%, or 95% sequence identity to SEQ ID NO: 133. The antibody for isolation/purification may comprise CDR 1-3 sequences set forth in SEQ ID NOs: 118-120 or may comprise the sequence set forth SEQ ID NO: 134 or a sequence having at least 80%, 85%, 90%, or 95% sequence identity to SEQ ID NO: 134. The peptide used for elution may be a peptide having higher affinity to the antibody for elution than the peptide comprised in the fusion protein, such as another peptide described herein.

The present invention further relates to a system comprising one peptide tag and two antibodies or two peptide tags and one antibody or two peptide tags and two antibodies as described herein.

The present invention also relates to a kit. The kit may comprise components necessary to carry out a method of the present invention. A kit for detection or purification of a fusion protein may comprise a nucleic acid or a nucleic acid expression construct encoding a peptide/epitope tag as defined herein, which may be present in the fusion protein. The nucleic acid may comprise a site, such as a cleavage or recombination site, that facilitates genetically fusing a polypeptide to the peptide/epitope tag. A nucleic acid sequence encoding the peptide/epitope tag may be operably linked to sequence elements that contain information regarding to transcriptional and/or translational regulation.

The kit may also comprise an antibody of the invention, optionally conjugated to a detectable label described herein, preferably an optically detectable label or an affinity tag. Alternatively or additionally, the kit may comprise a detectable moiety that can be conjugated to the antibody of the invention.

The kit may also comprise buffers and reagents necessary for the isolation/purification and/or detection methods of the present invention.

The kit may also comprise buffers and reagents necessary to introduce the nucleic acid or the nucleic acid expression construct comprised in the kit into a host cell.

The kit may also comprise at least one (secondary) specific binding partner as described herein or a (further) specific binding partner that specifically binds the (secondary) specific binding partner as described herein.

The kit may also comprise a solid support comprising the antibody of the invention immobilized or attached to the solid support. The kit may also comprise an isolated peptide as described herein suitable for competitive elution of a fusion protein bound to an antibody of the invention, or other means for elution of the fusion protein, such as a proteinase.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent applications, scientific publications, manufacturer's specifications, instructions, etc.) are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

EXAMPLES

Example 1: The System

In search for a novel epitope tag/binder system, we designed peptides SEQ ID NOs: 05-07 that form a stable α-helix in solution and are collectively referred to as "ALFA$^{ST}$ tag". These peptides do not have a known counterpart in any eukaryotic model system, they are nearly neutral at physiological pH and do not contain any primary amines that could be a target for common fixatives. The core ALFA tag sequence (FIG. 3A, amino acids written in blue) comprises an artificial peptide reported to form a stable α-helix in solution (Petukhov, M. et al. Design of stable alpha-helices using global sequence optimization. *J. Pept. Sci.* 15, 359-365 (2009)). It was selected based on the following properties: The sequence i) does not have a known counterpart in any eukaryotic model system, ii) it is neutral at physiological pH and iii) does not contain any primary amines that could be a target for common amine-reactive fixatives and cross linkers.

Figure 1A:
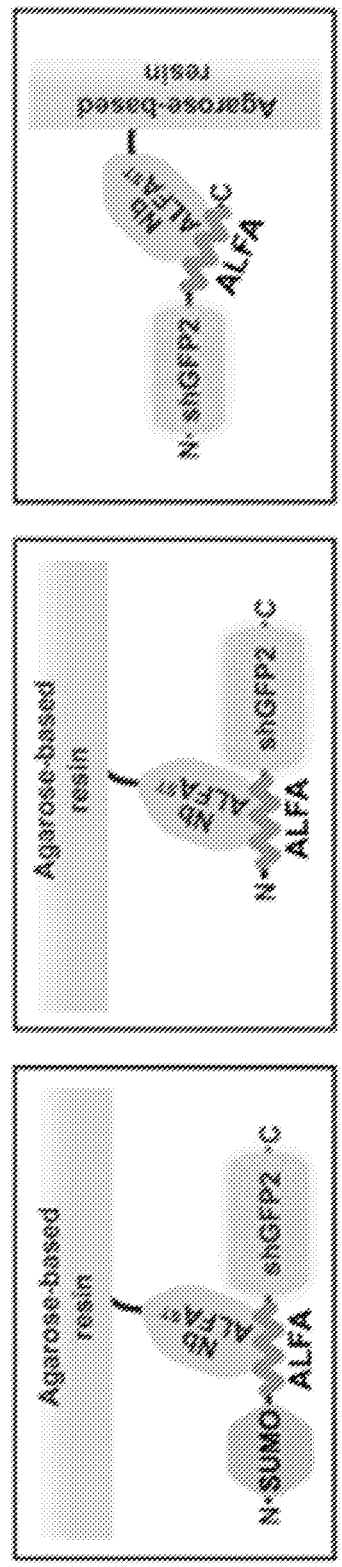
FIG. 1: Interaction of ALFA$^{ST}$ and ALFA$^{PE}$ with NbALFA$^{ST}$
Figure 1B:
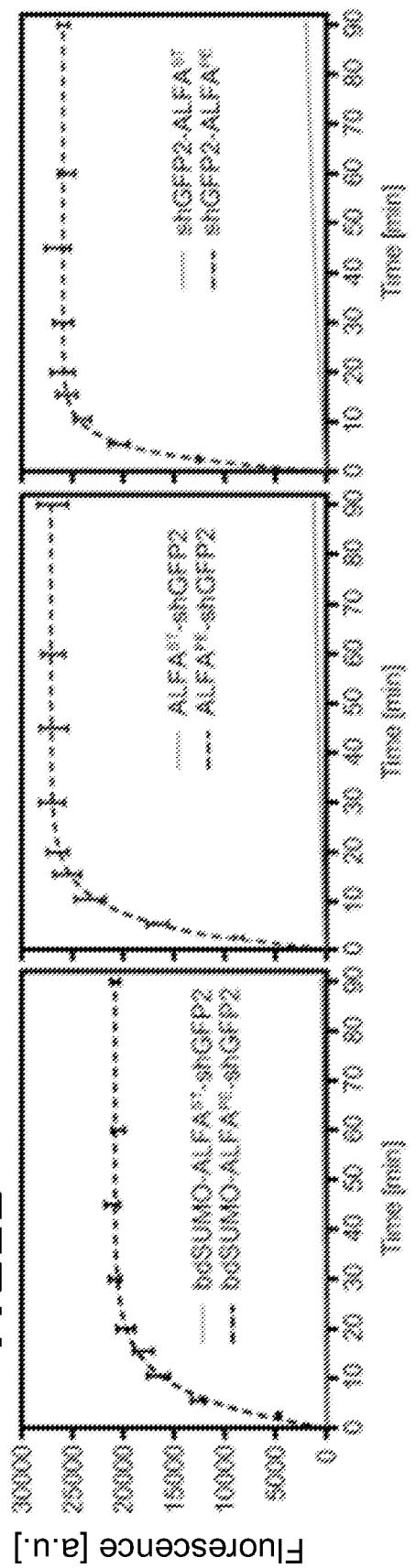

High-affinity nanobodies against ALFA$^{ST}$ were raised in Alpaca and selected by "Celline", a novel nanobody selection method employing antigen-specific enrichment of B-cells. To create a selective affinity resin, our favorite nanobody (NbALFA$^{ST}$, clone 1G5, SEQ IS NO: 133) was site-specifically coupled via a flexible linker to an agarose-based resin featuring low nonspecific protein binding. The resulting ALFA Selector$^{ST}$ resin was highly efficient in pulling down an ALFA$^{ST}$-shGFP2 fusion protein from *E. coli* extracts. Surprisingly, however, all approaches to elute the bound protein under native conditions by competition with ALFA$^{ST}$ peptide (Ac-PSRLEEELRRRLTEP-Amide set forth in SEQ ID NO: 179) failed. Even after 90 minutes competition with 10 column volumes of 200 μM peptide, >95% of the ALFA$^{ST}$-shGFP2 protein remained on the resin (FIG. 1B, middle panel, grey line). We thus assumed that the off-rate of the ALFA$^{ST}$ fusion proteins bound to the resin was too low to allow for an efficient competition by the peptide. We therefore performed systematic and rational mutagenesis in order to identify ALFA$^{ST}$ mutants that bind sufficiently strong to NbALFA$^{ST}$ to allow for an efficient pull-down of target proteins, but on the other side could be eluted from the nanobody using the ALFA$^{ST}$ peptide. The peptides that were analyzed are shown in Table 2.

TABLE 2

| Sequence | Position | Class | $t_{1/2}$ |
|---|---|---|---|
| dsMRLEEELRRRLSKg (SEQ ID NO: 90) | M | n.d. | n.d. |
| dsMRLEEELRRRLSPg (SEQ ID NO: 91) | M | n.d. | n.d. |
| sdSG-EEELRRRLSPg (SEQ ID NO: 92) | M | T0 | <2 min |
| sdSG--EELRRRLSPg (SEQ ID NO: 93) | M | T0 | <2 min |
| dsGRLEEELRRR-SPg (SEQ ID NO: 94) | M | T0 | <2 min |
| dsGRLEEELRR--SPg (SEQ ID NO: 95) | M | T0 | <2 min |
| dsGRLEEELR---SPg (SEQ ID NO: 96) | M | T0 | <2 min |
| sdSGLEEEARRRLSPg (SEQ ID NO: 97) | M | T0 | <2 min |
| sdSGAEEELRRRLSPg (SEQ ID NO: 98) | M | T0 | <2 min |
| dsGALEEELRRRLSPg (SEQ ID NO: 99) | M | T0 | <2 min |
| dsGALEQEIRRRLSPg (SEQ ID NO: 100) | M | T0 | <2 min |
| dsGRLEQEIRRALSPg (SEQ ID NO: 101) | M | T0 | <2 min |
| dsGRLEQEIRRQLSPg (SEQ ID NO: 102) | M | T0 | <2 min |
| dsGRLEQEIRRELSPg (SEQ ID NO: 103) | M | T0 | <2 min |
| pdSGLEQELRRRLPTa (SEQ ID NO: 104) | M | T0 | <2 min |
| dpSGLEQELRRRLPTa (SEQ ID NO: 105) | M | T0 | <2 min |
| dsPGLEQELRRRLPTa (SEQ ID NO: 106) | M | T0 | <2 min |
| dsGPLEQELRRRLPTa (SEQ ID NO: 107) | M | T0 | <2 min |

TABLE 2-continued

| Sequence | Position | Class | t$_{1/2}$ |
|---|---|---|---|
| gpSGLEQELRRRLa (SEQ ID NO: 108) | C | T0 | <2 min |
| MSAVEEELRRRLSPs (SEQ ID NO: 109) | N | T0 | <2 min |
| MSGLEQELRRRLTPs (SEQ ID NO: 110) | N | T0 | <2 min |
| MSAVEEELRRRLSPs (SEQ ID NO: 111) | N | T0 | <2 min |
| MpSAVEEELRRRLSPs (SEQ ID NO: 112) | N | T0 | <2 min |
| MsSAVEEELRRRLSPs (SEQ ID NO: 113) | N | T0 | <2 min |
| psGRLEEELRRRLP. (SEQ ID NO: 114) | C | T0 | <2 min |
| dsGRLEEELRRRLSKg (SEQ ID NO: 62) | M | T1 | 2-30 min |
| dsGRLEEELRRRLSPg (SEQ ID NO: 63) | M | T1 | 2-30 min |
| sdSGLEEELRRRLSPg (SEQ ID NO: 64) | M | T1 | 2-30 min |
| sdSGVEEELRRRLSPg (SEQ ID NO: 65) | M | T1 | 2-30 min |
| sdSAVEEELRRRLSPg (SEQ ID NO: 66) | M | T1 | 2-30 min |
| sdSGLQEELRRRLSPg (SEQ ID NO: 67) | M | T1 | 2-30 min |
| sdSGLEEQLRRRLSPg (SEQ ID NO: 68) | M | T1 | 2-30 min |
| sdSGLEEEIRRRLSPg (SEQ ID NO: 69) | M | T1 | 2-30 min |
| sdSGLEEEVRRRLSPg (SEQ ID NO: 70) | M | T1 | 2-30 min |
| dsGELEEELRRRLSPg (SEQ ID NO: 71) | M | T1 | 2-30 min |
| dsGRLEQELRRRLSPg (SEQ ID NO: 72) | M | T1 | 2-30 min |
| dsGRLEEEIRRRLSPg (SEQ ID NO: 73) | M | T1 | 2-30 min |
| dsGRLEQEIRRRLSPg (SEQ ID NO: 74) | M | T1 | 2-30 min |
| dsGRLEQEIARRLSPg (SEQ ID NO: 75) | M | T1 | 2-30 min |
| dsGRLEQEIQRRLSPg (SEQ ID NO: 76) | M | T1 | 2-30 min |
| dsGRLEQEIERRLSPg (SEQ ID NO: 77) | M | T1 | 2-30 min |
| dsGRLEQEIRARLSPg (SEQ ID NO: 78) | M | T1 | 2-30 min |
| dsGRLEQEIRQRLSPg (SEQ ID NO: 79) | M | T1 | 2-30 min |
| dsGRLEQEIRERLSPg (SEQ ID NO: 80) | M | T1 | 2-30 min |
| gpSRLEEELRRRL. (SEQ ID NO: 81) | C | T1 | 2-30 min |
| MSGLEQELRRRLTPs (SEQ ID NO: 82) | N | T1 | 2-30 min |
| MsGRLEEELRRRLSPs (SEQ ID NO: 83) | N | T1 | 2-30 min |
| spSAVEEELRRRLSPs (SEQ ID NO: 84) | M | T1 | 2-30 min |
| gpSAVEEELRRRLS. (SEQ ID NO: 85) | C | T1 | 2-30 min |
| MpSGLEQELRRRLTPs (SEQ ID NO: 86) | N | T1 | 2-30 min |
| MsSGLEQELRRRLTPs (SEQ ID NO: 87) | N | T1 | 2-30 min |
| MpSGRLEEELRRRLSps (SEQ ID NO: 88) | N | T1 | 2-30 min |
| msGRLEEELRRRLSPs (SEQ ID NO: 83) | M | T1 | 2-30 min |
| msGRLEEELRRRLSP (SEQ ID NO: 89) | C | T1 | 2-30 min |
| msGRLEEELRRRLSP (SEQ ID NO: 33) | N, M, C | T1 | 2-30 min |
| sdSGLEQELRRRLSPg (SEQ ID NO: 34) | M | T1 | 2-30 min |
| pdGGLEQELRRRLTAp (SEQ ID NO: 35) | M | T1 | 2-30 min |
| psGGLEQELRRRLTAp (SEQ ID NO: 36) | M | T1 | 2-30 min |
| dsPGLEQELRRRLTAp (SEQ ID NO: 37) | M | T1 | 2-30 min |
| pdSGLEQELRRRLTP$_a$ (SEQ ID NO: 38) | M | T1 | 2-30 min |
| spSGLEEELRRRLTAep (SEQ ID NO: 39) | M | T1 | 2-30 min |
| gpSGLEQELRRRLT. (SEQ ID NO: 40) | C | T1 | 2-30 min |
| gpSGLEQELRRRLTAas. (SEQ ID NO: 41) | C | T1 | 2-30 min |
| spSRLEEELRRRLPSk (SEQ ID NO: 42) | M | T1 | 2-30 min |
| spSGLEQELRRRLTPs (SEQ ID NO: 43) | M | T1 | 2-30 min |
| spGRLEQEIRRRLSPs (SEQ ID NO: 44) | M | T1 | 2-30 min |
| psGRLEEELRRRLSPs (SEQ ID NO: 45) | M | T1 | 2-30 min |
| psGRLEEELRRRLS. (SEQ ID NO: 46) | C | T1 | 2-30 min |
| psGRLEEELRRRLA. (SEQ ID NO: 47) | C | T1 | 2-30 min |
| psGRLEEELRRRLSP. (SEQ ID NO: 48) | C | T1 | 2-30 min |

TABLE 2-continued

| Sequence | Position | Class | $t_{1/2}$ |
|---|---|---|---|
| pdSGLEQELRRRLSPg (SEQ ID NO: 50) | M | T2 | 20-100 min |
| pdSGLEQELRRRLTAp (SEQ ID NO: 51) | M | T2 | 20-100 min |
| psSGLEQELRRRLTAp (SEQ ID NO: 52) | M | T2 | 20-100 min |
| dpSGLEQELRRRLTAp (SEQ ID NO: 53) | M | T2 | 20-100 min |
| dsGPLEQELRRRLTAp (SEQ ID NO: 54) | M | T2 | 20-100 min |
| spSRLEEELRRRLTAep (SEQ ID NO: 55) | M | T2 | 20-100 min |
| spSGLEEELRRRLTAp (SEQ ID NO: 56) | M | T2 | 20-100 min |
| spSGLEEELRRRLDAp (SEQ ID NO: 57) | M | T2 | 20-100 min |
| spSGLEEELRRRLEAp (SEQ ID NO: 58) | M | T2 | 20-100 min |
| spSGLEEELRRRLTDp (SEQ ID NO: 59) | M | T2 | 20-100 min |
| spSGLEEELRRRLTAdp (SEQ ID NO: 60) | M | T2 | 20-100 min |
| gpSGLEQELRRRLTA. (SEQ ID NO: 169) | C | T2 | 20-100 min |
| spSGLEQELRRRLTDp (SEQ ID NO: 170) | M | T2 | 20-100 min |
| spSGLEQELRRRLTAdp (SEQ ID NO: 171) | M | T2 | 20-100 min |
| spSGLEQELRRRLTAep (SEQ ID NO: 172) | M | T2 | 20-100 min |
| dsPGLEQELRRRLTAp (SEQ ID NO: 173) | M | T2 | 20-100 min |
| spSGLEQELRRRLSP. (SEQ ID NO: 174) | M | T2 | 20-100 min |
| grSRLEEELRRRLTA. (SEQ ID NO: 08) | C | T3 | >100 min |
| pgSRLEEELRRRLTAp (SEQ ID NO: 09) | M | T3 | >100 min |
| psTRLEEELRRRLTAp (SEQ ID NO: 10) | M | T3 | >100 min |
| spSRLEEELRRRLTAp (SEQ ID NO: 11) | M | T3 | >100 min |
| spSRLEEELRRRLDAp (SEQ ID NO: 12) | M | T3 | >100 min |
| spSRLEEELRRRLEAp (SEQ ID NO: 13) | M | T3 | >100 min |
| spSRLEEELRRRLTDp (SEQ ID NO: 14) | M | T3 | >100 min |
| spSRLEEELRRRLTEp (SEQ ID NO: 15) | M | T3 | >100 min |
| spSRLEEELRRRLTAdp (SEQ ID NO: 16) | M | T3 | >100 min |
| spSGLEEELRRRLTEp (SEQ ID NO: 17) | M | T3 | >100 min |
| gPSRLEEELRRRLT. (SEQ ID NO: 18) | C | T3 | >100 min |
| gPSRLEEELRRRLTA. (SEQ ID NO: 19) | C | T3 | >100 min |
| gPSRLEEELRRRLTAa. (SEQ ID NO: 20) | C | T3 | >100 min |
| gPSRLEEELRRRLTAas. (SEQ ID NO: 21) | C | T3 | >100 min |
| spSGLEQELRRRLTAp (SEQ ID NO: 22) | M | T3 | >100 min |
| spSGLEQELRRRLDAp (SEQ ID NO: 23) | M | T3 | >100 min |
| spSGLEQELRRRLEAp (SEQ ID NO: 24) | M | T3 | >100 min |
| spSGLEQELRRRLTEp (SEQ ID NO: 25) | M | T3 | >100 min |
| gpSRLEEELRRRLTAp. (SEQ ID NO: 26) | C | T3 | >100 min |
| gpSRLEEELRRRLTEp. (SEQ ID NO: 27) | C | T3 | >100 min |
| gpSRLEEELRRRLTE. (SEQ ID NO: 28) | C | T3 | >100 min |
| MSRLEEELRRRLTEp (SEQ ID NO: 29) | N | T3 | >100 min |
| MpSRLEEELRRRLTEp (SEQ ID NO: 05) | N | T3 | >100 min |
| pSRLEEELRRRLTEp (SEQ ID NO: 06) | M | T3 | >100 min |
| pSRLEEELRRRLTE (SEQ ID NO: 07) | C | T3 | >100 min |
| MsSRLEEELRRRLTEp (SEQ ID NO: 30) | N | T3 | >100 min | n.d: not determined
Positions: N: N-terminal; M: in between two folded domains; C: C-terminal As a rough estimation, which is based on an estimated on-rate of 2*10⁵ (1/(M*sec)), which is commonly observed for sdAbs, $t_{1/2}$ of <2 min correspond to a $K_d$ of > about 30 nM, $t_{1/2}$ of 2-30 min correspond to a $K_d$ of about 2-30 nM, $t_{1/2}$ of 20-100 min correspond to a $K_d$ of about 0.6-3 nM, and $t_{1/2}$ of more than 100 min correspond to a $K_d$ of about 1 nM or lower.

Figure 1C:
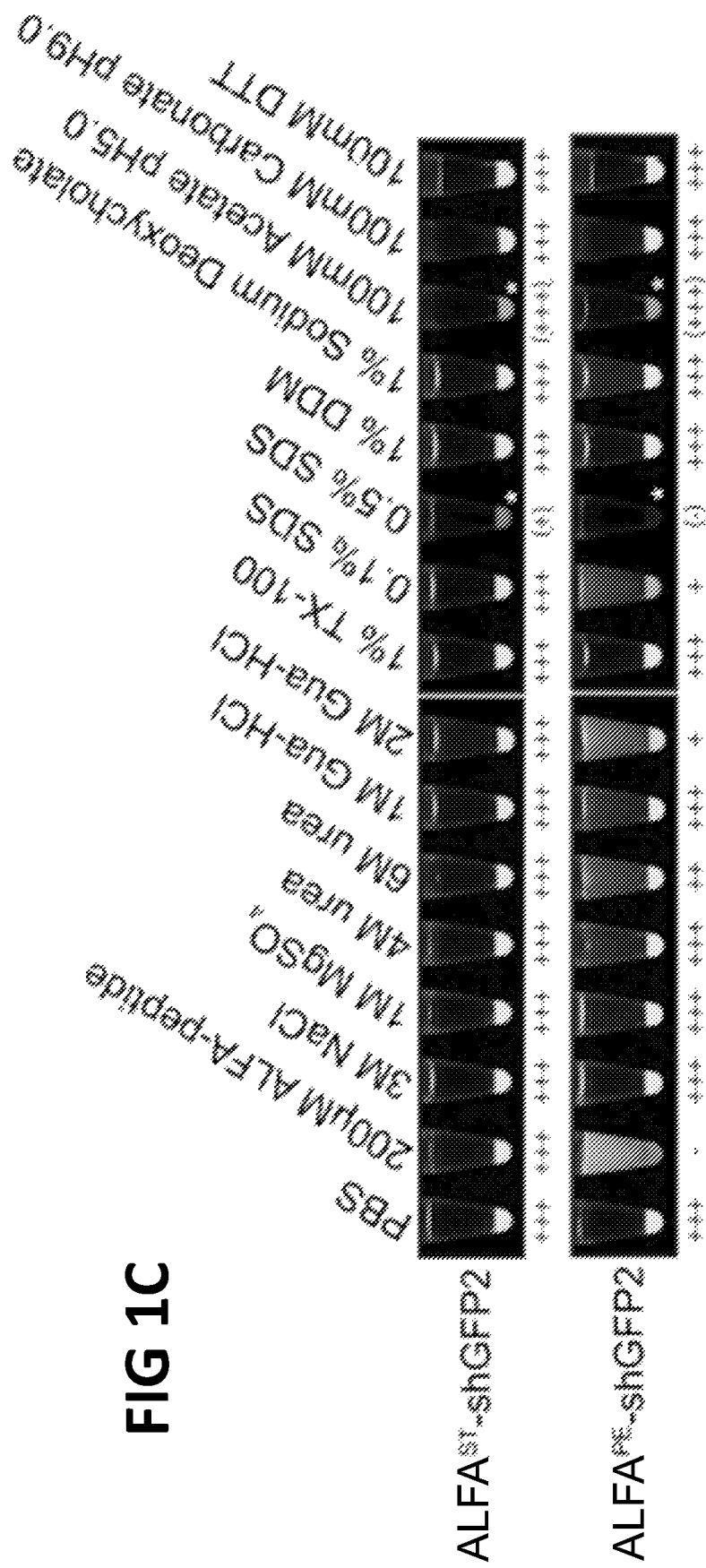

We found an ALFA mutant (ALFA$^{PE}$ for Peptide Elutable) (SEQ ID NO: 33) fulfilling these criteria. Proteins fused to ALFA$^{PE}$ efficiently bound to the ALFA Selector$^{ST}$. Binding was even resistant to harsh washing steps (e.g. up to 3M NaCl, 1M MgSO$_4$, 4M urea, 1% TX-100 or even 100 mM DTT, FIG. 1C). Efficient elution under native conditions could, however, be accomplished within 15-20 min at room temperature by competition with 200 μM of ALFA$^{ST}$ peptide (SEQ ID NO: 179) (FIG. 1B). Interestingly, both ALFA tag variants (ALFA$^{ST}$ and ALFA$^{PE}$) can be used at either terminus of the target protein or even between two protein domains with only marginal effects on the binding to NbALFA$^{ST}$ (FIG. 1B).

Example 2: Application of NbALFA$^{ST}$ for Pull-Down of ALFA-Tagged Target Proteins To address the specificity of ALFA Selector$^{ST}$, we performed pull-down experiments from complex lysates under physiological conditions. To this end, E. coli or HeLa lysates prepared in PBS were spiked with 3 µM of shGFP2 (Frey, S. et al. Surface Properties Determining Passage Rates of Proteins through Nuclear Pores. Cell 174, 202-217.e9 (2018)) N-terminally tagged with either ALFA$^{ST}$ or ALFA$^{PE}$, that have been expressed in E. coli and purified via Nickel-chelate chromatography followed by size exclusion chromatography before. The purified input proteins are shown in FIG. 2A. From all lysates, both fusion proteins efficiently bound to the ALFA-Selector$^{ST}$ (FIG. 2B and FIG. 2C). As expected from our earlier experiments (FIG. 1), GFP tagged with ALFA$^{PE}$ could be efficiently eluted within 20 min under native conditions using 200 µM of ALFA$^{ST}$ peptide while the ALFA$^{ST}$-tagged target protein required harsher (denaturing) conditions for efficient elution. Strikingly, pull-downs from both lysates were highly specific. Even after elution with SDS buffer, the number and strength of detectable impurities originating from lysate proteins was very low. When ALFA$^{PE}$-GFP fusion proteins were eluted using the ALFA$^{ST}$ peptide, essentially all detectable bands were identical in the eluate fractions obtained from both lysates. These bands could therefore be attributed to artifacts created by the target protein itself (e.g. maturation bands or DTT-resistant dimers). Interestingly, especially after peptide elution, the eluate fractions contained significantly less contaminating proteins than the substrates used as input material (which had been purified using two consecutive chromatographic steps; FIG. 2A).

Example 3: Co-Immunoprecipitation Using ALFA$^{PE}$-Tagged Target Protein and ALFA Selector$^{ST}$ To see if the ALFA system can also be applied for more delicate co-immunoprecipitation experiments, we tried to pull down the binary E. coli YfgM-PpiD inner membrane protein complex (Götzke, H. et al. YfgM is an ancillary subunit of the SecYEG translocon in Escherichia coli. J Biol Chem 289, 19089-19097 (2014)) under native conditions (FIG. 2D). To this end, either wild-type YfgM or YfgM-ALFA$^{PE}$ was expressed in a yfgMΔ strain. To ensure nearly physiological expression levels, both YfgM variants were expressed from a low-copy plasmid under the control of the endogenous promoter. When using the YfgM-ALFA$^{PE}$-containing total lysate prepared in the presence of the mild non-ionic detergent DDM as input, ALFA Selector$^{ST}$ was able to pull down the YfgM-PpiD complex in a specific and detergent-resistant manner. This indicated that the ALFA$^{PE}$ tag was compatible with the formation of this labile membrane complex. Importantly, the native and non-modified membrane protein complex could be recovered from ALFA Selector$^{ST}$ resin within 20 min under physiological conditions using 200P M of ALFA$^{ST}$ peptide. YfgM and its interaction partner PpiD specifically associated with ALFA Selector$^{ST}$ via the ALFA$^{PE}$ tag present on the (periplasmic) C-terminus of YfgM, as the complex could not be purified from a control lysate expressing non-tagged YfgM. The ALFA$^{PE}$ tag together with the ALFA Selector$^{ST}$ resin can thus not only be used for purification of proteins from various sources, it is also suited for native pull-downs of challenging (membrane) protein complexes.

Example 4: Detection of ALFA$^{ST}$-Tagged Proteins by Direct Immunofluorescence We first tested if fluorescently labeled NbALFA$^{ST}$ could be applied for immuno-detection of ALFA-tagged proteins in PFA-fixed samples. Indeed, using the NbALFA$^{ST}$ (SEQ ID NO: 133) coupled to two fluorophores (FluoTag-X2 anti-ALFA AbberiorStar635P), a specific staining pattern could be obtained irrespective of the localization of the ALFA$^{ST}$ tag or ALFA$^{PE}$ tag within the target proteins in mammalian cells. More specifically, we successfully tested target proteins with ALFA tags placed at the C-terminus (Tom70-EGFP-ALFA$^{ST}$, FIG. 3C; Tom70-EGFP-ALFA$^{PE}$, FIG. 3C), the N-terminus (ALFA$^{ST}$-FLAG-Vimentin, FIG. 3D and FIG. 4A; ALFA$^{PE}$-FLAG-Vimentin, FIG. 4A), or between a folded domain and a transmembrane domain (EGFP-ALFA$^{ST}$-TM, FIG. 4B).

Example 5: ALFA$^{ST}$-Tagged Proteins Show Normal Folding, Targeting and Multimerization Status Importantly, all assayed target proteins showed their characteristic localization (Tom70-EGFP-ALFA: mitochondrial outer membrane; ALFA-Vimentin: characteristic filamentous structures; EGFP-ALFA$^{ST}$-TM: plasma membrane), indicating that the ALFA-tags did not interfere with general folding or proper targeting of the tagged proteins. Proper incorporation of ALFA$^{ST}$-Vimentin and ALFA$^{PE}$-Vimentin into characteristic intermediate filament structures (FIG. 3D and FIG. 4A) furthermore suggests that the ALFA-tags does not interfere with proper filament assembly.

To more sensitively address if the ALFA$^{ST}$ tag influence the intracellular localization of a fused protein of interest, we statistically analyzed the localization of cytosolic EGFP harboring N- or C-terminal ALFA$^{ST}$ tags transfected into mammalian cells (FIG. 5). In this assay, the nucleocytoplasmic distribution of EGFP tagged with ALFA$^{ST}$ at either terminus was indistinguishable from non-tagged EGFP. Importantly, we did not observe any signs for an atypical association of the analyzed ALFA$^{ST}$ fusion proteins to cellular compartments (e.g. membranes or organelles). Furthermore, gelfiltration of recombinant ALFA$^{ST}$-tagged EGFP variants confirmed their monomeric state indicating that the ALFA$^{ST}$ tag does not induce multimerization. We therefore conclude that the ALFA$^{ST}$ tag does not generally impair the behavior of target proteins. We, however, note that (as for any other tag), specific effects on given target proteins have to be analyzed on a protein-to-protein basis.

Example 6: ALFA Tags are Compatible with Common Fixation Conditions

Figures 3A, 3B:
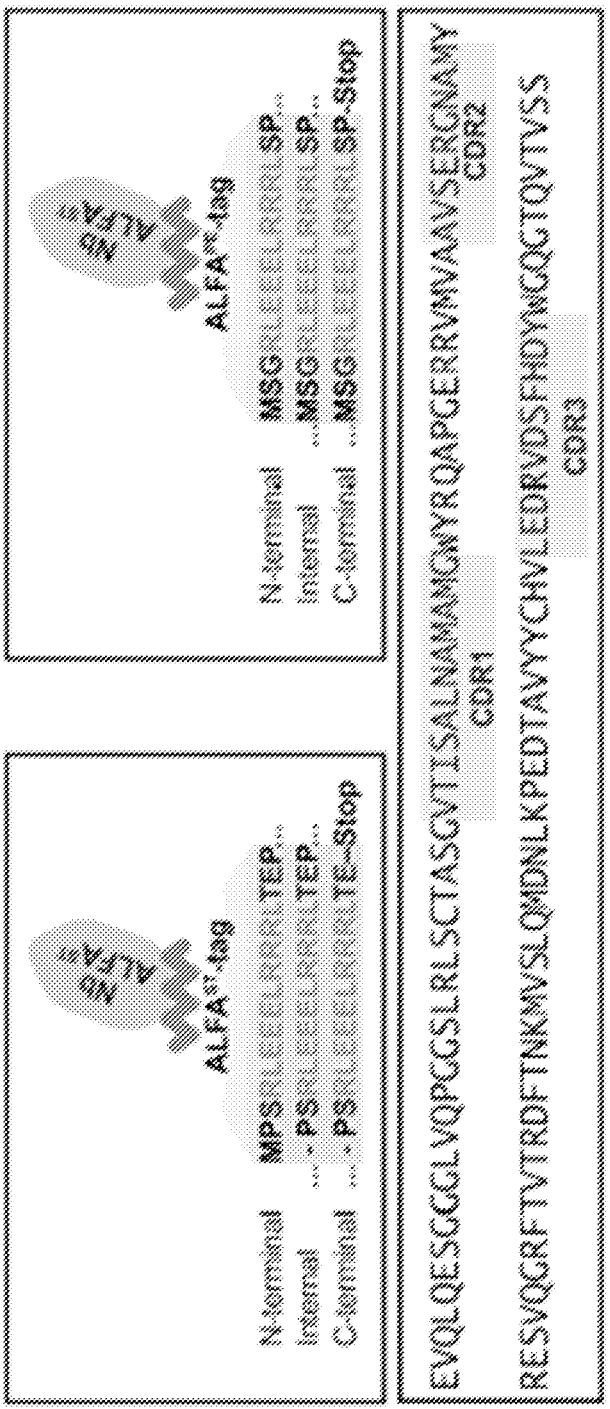
Figure 3C:
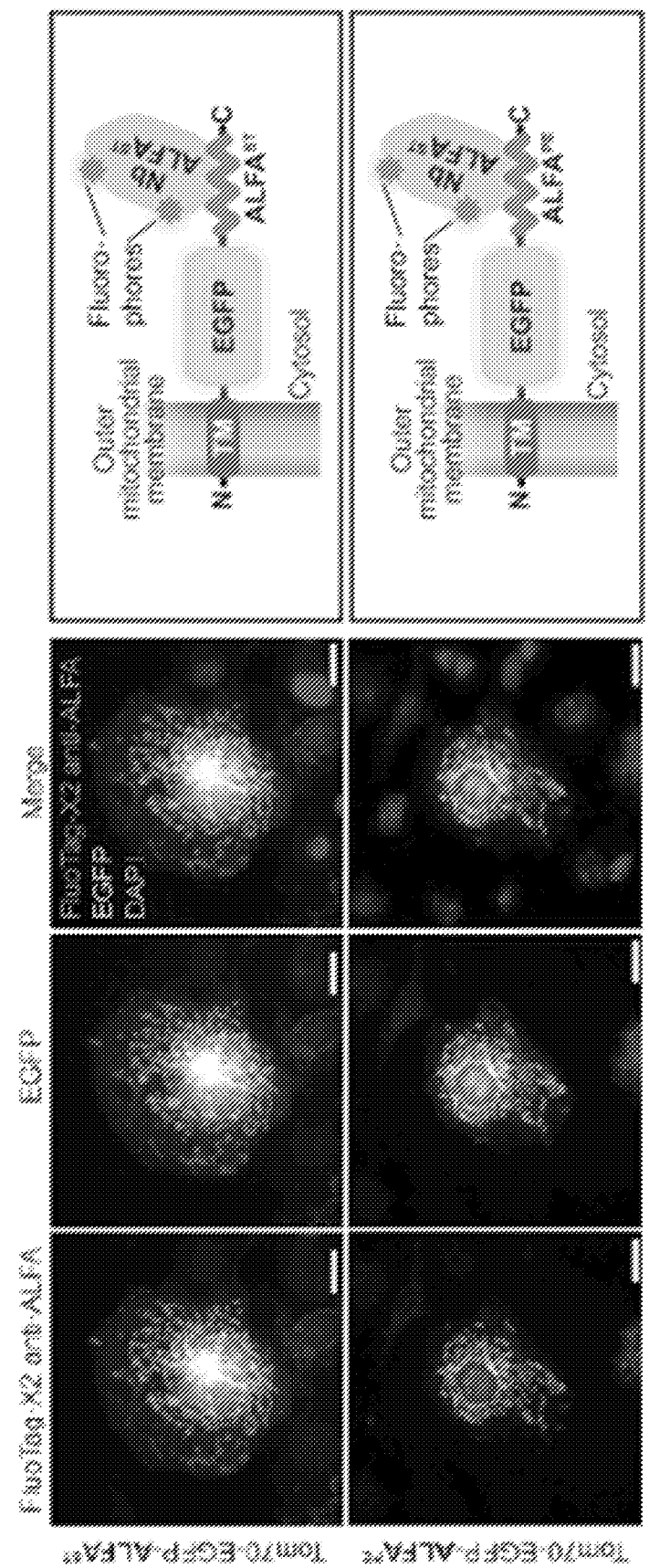
Figure 3D:
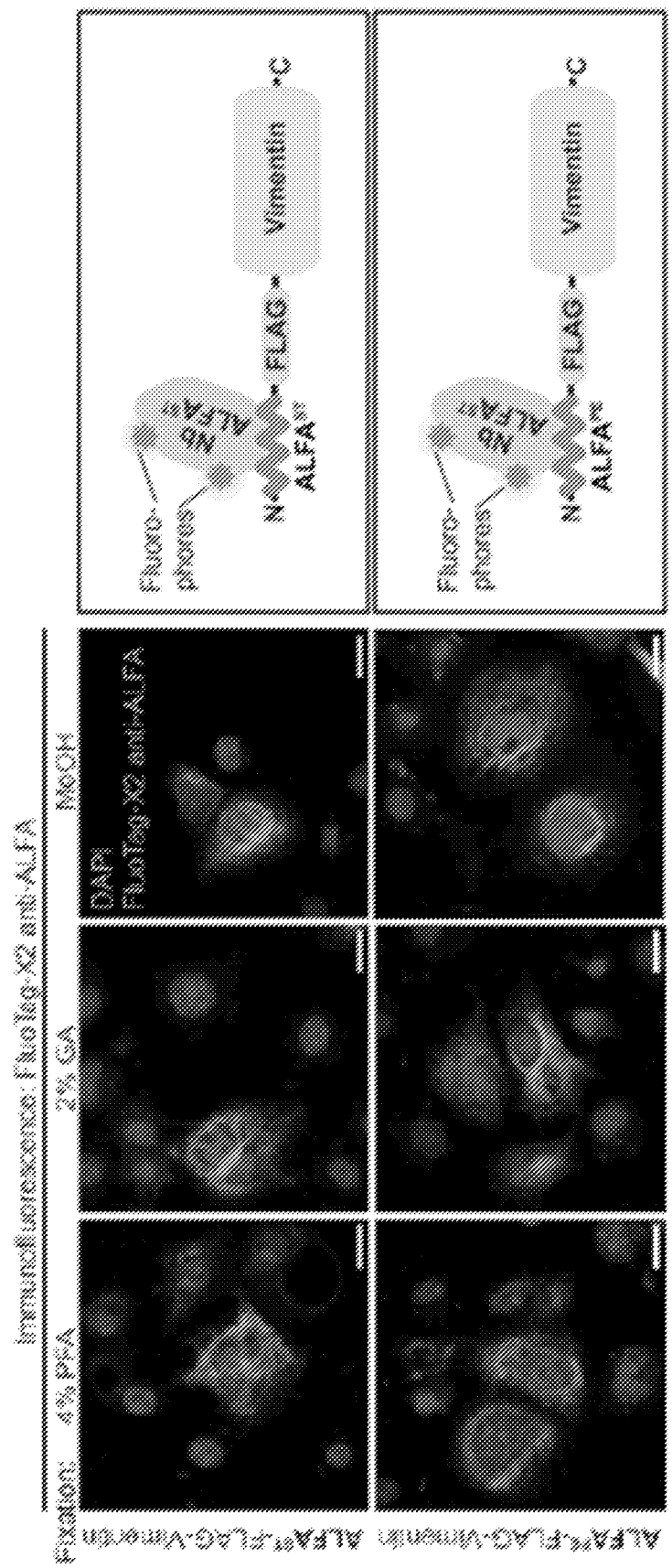

Immunofluorescence (IF) applications often require optimization of fixation conditions. This may be complicated, especially if proteins requiring different fixation conditions need to be localized in the same specimen. In addition, established epitope tags often contain lysines that render them potentially sensitive towards modification by amine-reactive fixatives (Table 1). The ALFA tags, in contrast, do not contain lysines. In line with these considerations, the ALFA$^{ST}$ tag and the ALFA$^{PE}$ tag could be detected after standard fixation with 4% paraformaldehyde (PFA) or precipitative fixation with 100% methanol and was even resistant to fixation with 2% glutaraldehyde (FIG. 3D). Both ALFA tags are thus compatible with most standard fixation methods and may even prove to be useful in electron microscopic applications, where glutaraldehyde is preferred due to its ability to preserve structures at the nanoscale.

Example 7: Detecting ALFA$^{ST}$-Tagged Proteins In Vivo

Figure 3E:
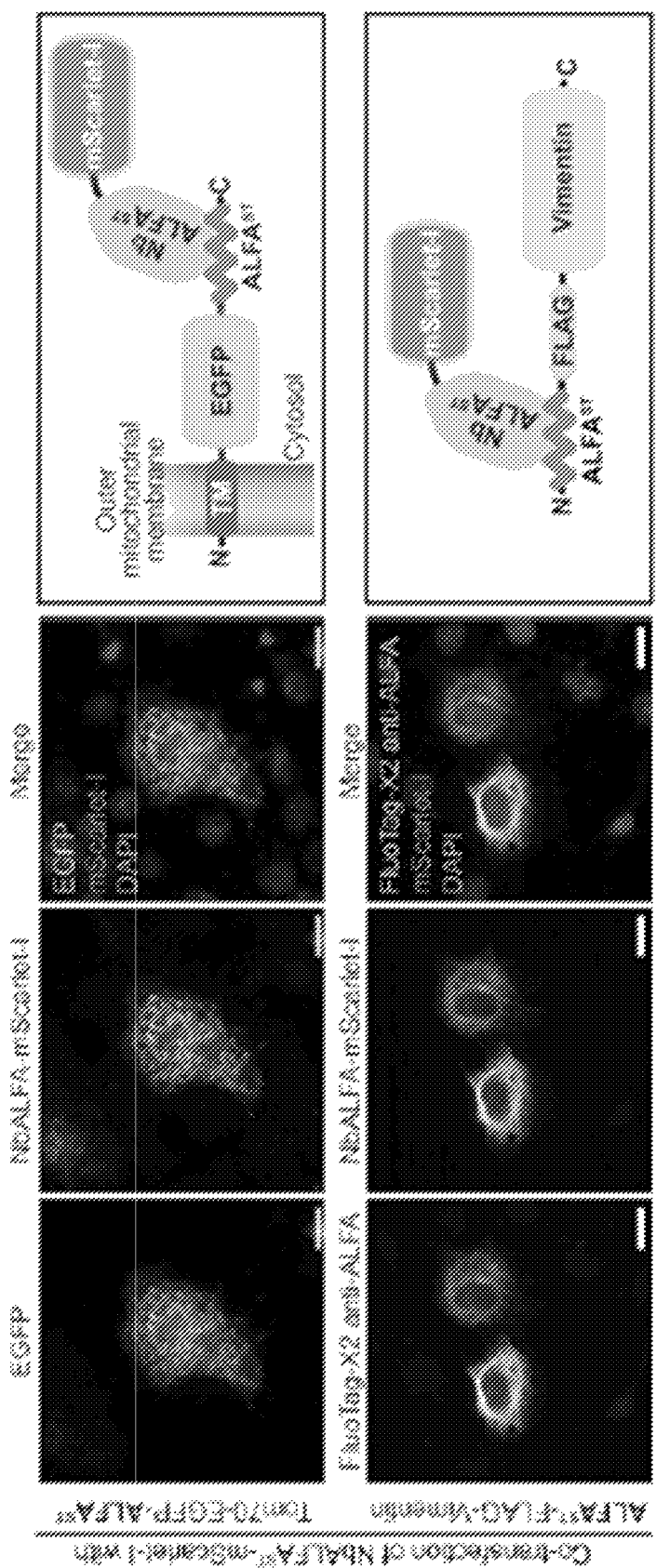

We next wanted to know if our NbALFA$^{ST}$ can also be used as an intrabody. Such nanobodies expressed in situ in the cytoplasm (or other compartments) of a target cell are often used to localize or manipulate target proteins in life cells (Caussinus, E., Kanca, O. & Affolter, M. Fluorescent fusion protein knockout mediated by anti-GFP nanobody. *Nat Struct Mol Biol* 19, 117-121 (2012); Kirchhofer, A. et al. Modulation of protein properties in living cells using nanobodies. *Nat Struct Mol Biol* 17, 133-138 (2010)). Such applications depend on the stability and functionality of a given nanobody in the reducing environment of the cytoplasm of a eukaryotic host cell. To test our nanobody under such conditions, we co-expressed ALFA$^{ST}$-tagged target proteins (ALFA$^{ST}$-Vimentin or Tom70-EGFP-ALFA$^{ST}$) with NbALFA$^{ST}$ fused to mScarlet-I (Bindels, D. S. et al. mScarlet: a bright monomeric red fluorescent protein for cellular imaging. *Nat Methods* 11, 121-122 (2016)). Indeed, in cells co-transfected with both constructs, the mScarlet-I signal robustly co-localized with the respective ALFA$^{ST}$_tagged target protein (FIG. 3E).

Example 8: Western-Blot

In order to test if the ALFA-tag can be detected with a Western-blot using fluorescently labeled NbALFA$^{ST}$, we analyzed lysates from COS-7 cells transfected with ALFA$^{ST}$-tagged Vimentin (FIG. 6A and FIG. 7A) or ALFA$^{PE}$-tagged Vimentin (FIG. 6A). Lysates from cells transfected with a non-related plasmid served as control. After SDS-PAGE and Western-blotting, ALFA-tagged vimentins could specifically be detected using NbALFA$^{ST}$ labeled with IRDye800CW (FluoTag-X2 anti-ALFA IRDye800CW). Only a limited number of minor non-specific bands could be detected in the control lysate lacking ALFA-tagged proteins (FIG. 7A).

To directly compare the performance of NbALFA$^{ST}$ with commonly used monoclonal tools recognizing epitope tags, we produced maltose-binding protein (MBP) fused to multiple epitope tags (HA, myc, FLAG and ALFA$^{ST}$, FIG. 6B). Individual detection of each epitope tag with identical concentrations of primary antibody (or nanobody) showed significant differences in signal strength and sensitivity (FIG. 6C, FIG. 7B). The detected signal obtained for the ALFA$^{ST}$ tag employing fluorescently labeled NbALFA$^{ST}$ was overall 3-10-fold stronger as compared to signals obtained for all other epitope tags. This result was especially striking as the detection with the monoclonal antibodies (anti-FLAG M2, anti-HA F-7, anti-myc 9E10) involved signal amplification due to the use of a polyclonal secondary antibody, whilst detection of the ALFA$^{ST}$ tag exclusively relied on directly labeled NbALFA$^{ST}$. Without further optimizing the detection conditions, NbALFA$^{ST}$ yielded a remarkably linear signal over at least three orders of magnitude (FIG. 6D) and was able to detect target protein amounts as low as 100 pg. The detection limit was thus ~10-times lower than observed for all other epitope tags.

Example 9: Capture of ALFA$^{ST}$-Tagged Target Proteins Using ALFA Selector Resins Next, we site-specifically immobilized NbALFA$^{ST}$ on an agarose-based resin with ultra-low background via a hydrophilic and flexible linker. Binding to the nanobody-coupled resin was analyzed using an ALFA$^{ST}$-tagged GFP variant (shGFP2; Frey, S. et al. Surface Properties Determining Passage Rates of Proteins through Nuclear Pores. *Cell* 174, 202-217.e9 (2018); FIG. 8A, B). As expected, shGFP2-ALFA$^{ST}$ efficiently and tightly bound to the resulting resin. Binding was, however, too strong to allow for a competitive peptide elution from the resin even when a significant excess of free ALFA$^{ST}$ peptide was used (FIG. 8A, black solid line). Even after 60 minutes competition with 10 column volumes of 200 µM peptide, >95% of the shGFP2-ALFA$^{ST}$ protein remained on the resin. We therefore called the NbALFA$^{ST}$-charged resin "ALFA Selector$^{ST}$" (for Super-Tight). Based on the structure of the NbALFA$^{ST}$-ALFA$^{ST}$ complex, we followed a rational mutagenesis approach to identify weaker NbALFA$^{ST}$ mutants that would allow for an efficient peptide elution while stably associating with ALFA$^{ST}$_tagged proteins in the absence of free ALFA$^{ST}$ peptide. We found an NbALFA mutant, NbALFA$^{PE}$ (for Peptide Elution), fulfilling these criteria: An agarose-resin with immobilized NbALFA$^{PE}$ (ALFA Selector$^{PE}$) tightly bound shGFP2-ALFA$^{ST}$. Even upon washing for >1 h, the target protein remained stably bound to the resin. It was, however, efficiently released under native conditions within ~15-20 min ($t_{1/2}$~3 min) at room temperature by competition with free ALFA$^{ST}$ peptide (FIG. 8B and FIG. 10A, black solid line). Similar elution kinetics were found when the ALFA$^{ST}$ tag was placed between two folded domains (FIG. 10B), while an N-terminally ALFA$^{ST}$-tagged shGFP2 eluted slightly quicker from ALFA Selector$^{PE}$ ($t_{1/2}$~50 sec; FIG. 10C). Remarkably, in the absence of competing peptide, spontaneous elution of all target proteins from both ALFA Selector$^{ST}$ and ALFA Selector$^{PE}$ was insignificant (FIG. 8B and FIG. 10 dotted grey lines).

Example 10: The Interaction of ALFA-Tagged Proteins with ALFA Selector is Compatible with Stringent Washing We decided to further analyze the biochemical properties of both ALFA Selector resins. To this end, both resins were charged with either ALFA$^{ST}$-shGFP2 or shGFP2-ALFA$^{ST}$ and subjected to stringent washing steps (FIG. 8D). For all combinations of resin and substrate, the interaction was resistant even to harsh washing steps including up to 3M NaCl, 1M MgSO$_4$, 2M Guanidinium-HCl or 1% non-denaturing detergents like TX-100, DDM or Sodium-Desoxycholate. No dissociation was observed even after incubation with 100 mM DTT at room temperature. Slight differences between the different resins/substrate combinations were observed under denaturing conditions: A partial release of ALFA$^{ST}$-shGFP2 and, to an even lesser extend shGFP2-ALFA$^{ST}$ from ALFA Selector$^{PE}$ was observed upon washing with 4M or 6M urea, while both target proteins remained tightly bound to ALFA Selector$^{ST}$ under the same conditions. Surprising differences were observed after incubation with 0.1% SDS, as ALFA$^{ST}$-shGFP2 attached to ALFA Selector$^{PE}$ partially lost its fluorescence while staying bound to the resin. This effect was not observed with any other combination of resin and substrate.

Example 11: pH Resistance

In a similar assay, the loaded ALFA Selector resins were washed with buffers adjusted to different pH (FIG. 8E). The interaction was resistant at pH7.5 to 9.5 and only slightly affected at pH4.5. However, even after neutralization, both ALFA Selector resins remained completely non-fluorescent when washed with 100 mM Glycin at pH2.2. The eluted material, in contrast, successfully recovered its fluorescence at neutral pH (not shown), indicating that acidic elution with Glycin at pH2.2 is possible even from the tightly binding ALFA Selector$^{ST}$.

Example 12: Affinity Estimation

The affinity of shGFP2-ALFA$^{ST}$ to both NbALFA$^{ST}$ and NbALFA$^{PE}$ was determined in solution by microscale thermophoresis (MST). This technique provided evidence that NbALFA$^{PE}$ has a dissociation constant of ~15 nM, while NbALFA$^{ST}$ binds shGFP2-ALFA$^{ST}$ with a K$_d$ of ~10 µM, which is the lower detection limit of the device. These values are well in line with the dissociation kinetics observed during peptide elution (FIG. 8B) when assuming an on-rate of ~2×10$^5$/M*sec, which is commonly observed for nanobody-target interactions.

Figures 9A, 9B:
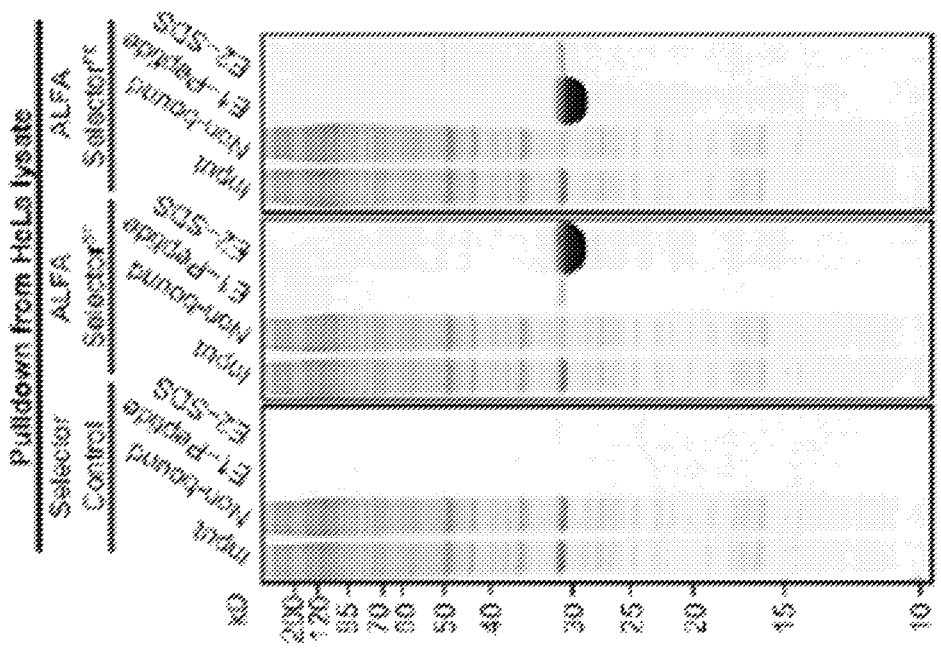
Figure 9C:
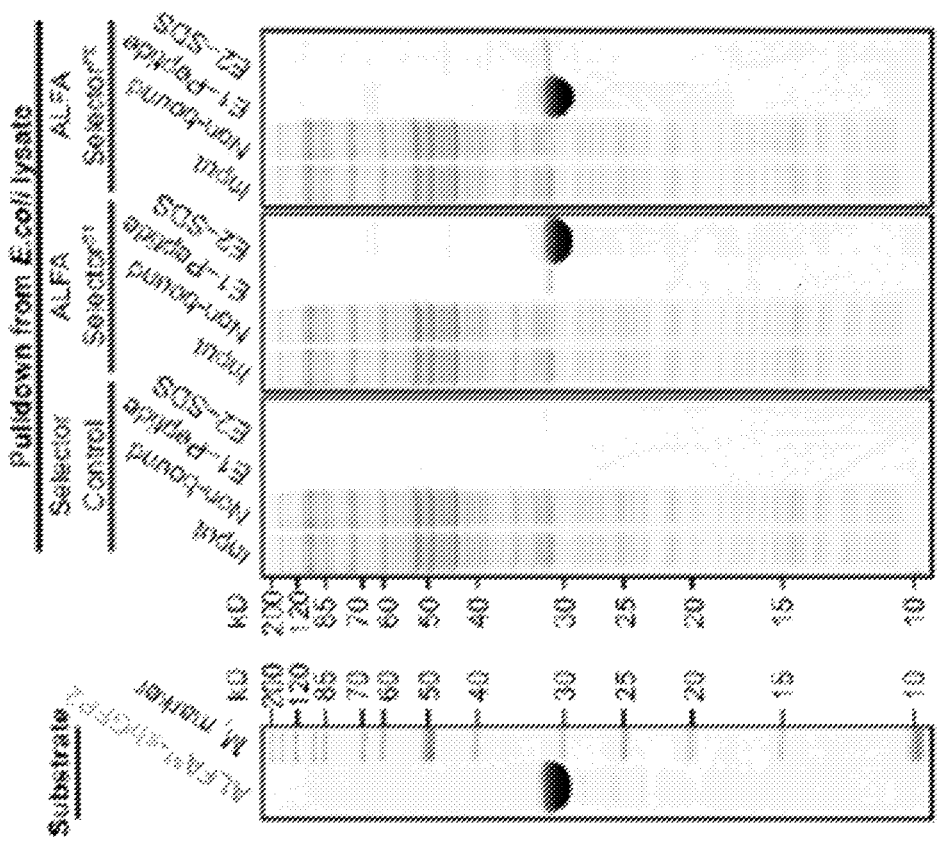

Example 13: Pull-Down of ALFA$^{ST}$-Tagged Target Proteins from Complex Lysates To address the specificity of our ALFA Selector resins, we performed pull-down experiments from complex lysates under physiological conditions (FIG. 9 A-C). To this end, E. coli or HeLa lysates prepared in PBS were spiked with 3 µM of recombinant purified ALFA$^{ST}$-shGFP2 (FIG. 9A). The fusion protein specifically bound to both ALFA Selectors but not to a control resin without coupled nanobody ("Selector control"). As expected from our earlier experiments, ALFA$^{ST}$-shGFP2 efficiently eluted from ALFA Selector$^{PE}$ under native conditions using 200 µM of ALFA$^{ST}$ peptide. In contrast, successful elution from ALFA Selector$^{ST}$ was observed only after treatment with SDS sample buffer. Strikingly, pull-downs from both, E. coli and HeLa lysates were highly specific (FIGS. 9B and C). After peptide elution from ALFA Selector$^{PE}$ essentially all visible bands could be attributed to the input protein, and even in the SDS eluate, the number and strength of detectable impurities originating from lysate proteins was very low. In fact, ALFA$^{ST}$-shGFP2 obtained by peptide elution from ALFA Selector$^{PE}$ in a single step contained significantly less contaminations than the protein used for spiking the input lysates (FIG. 9A). This observation was especially striking as the input protein had been purified using two consecutive chromatographic steps.

Example 14: Co-Immunoprecipitation Using ALFA Selector$^{PE}$ Resin

Figure 9D:
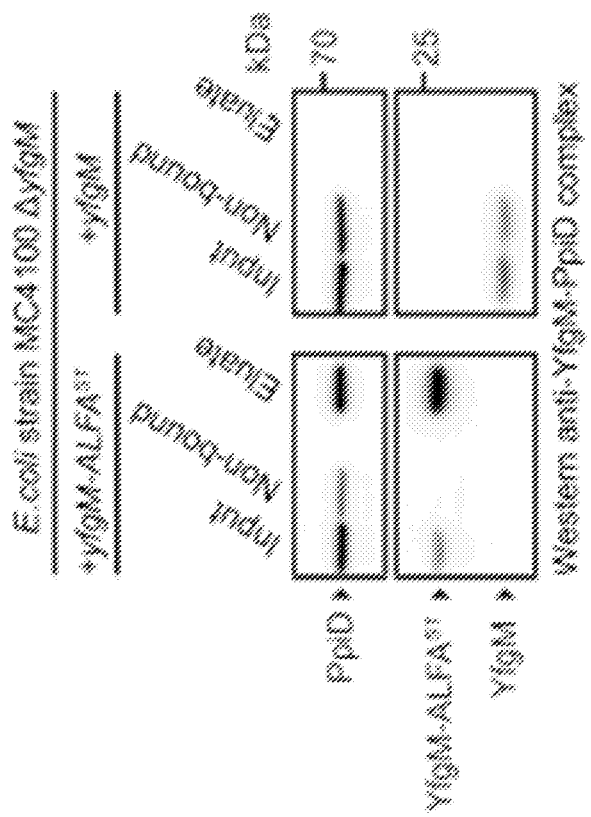
Figure 9D:
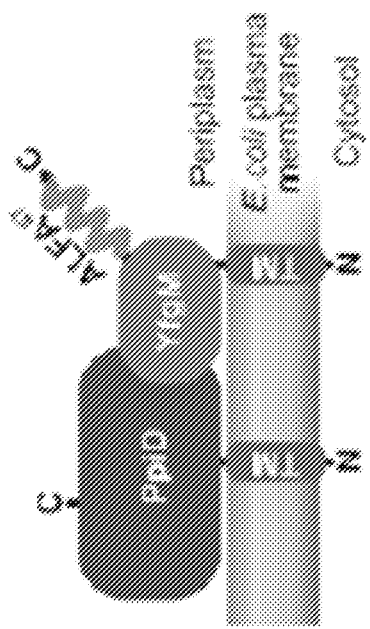

To see if the ALFA system can also be applied for more delicate co-immunoprecipitation experiments, we tried to pull down the binary E. coli YfgM-PpiD inner membrane protein complex (Götzke, H. et al. YfgM is an ancillary subunit of the SecYEG translocon in Escherichia coli. J Biol Chem 289, 19089-19097 (2014)) under native conditions (FIG. 9D). To this end, either wild-type YfgM or YfgM-ALFA$^{ST}$ was expressed in a yfgMΔ strain. To ensure nearly physiological expression levels, both YfgM variants were expressed from a low-copy plasmid under the control of the endogenous promoter. When using the YfgM-ALFA$^{ST}$-containing total lysate prepared in the presence of the mild non-ionic detergent DDM as input, ALFA Selector$^{PE}$ was able to pull down the YfgM-PpiD complex in a specific and detergent-resistant manner. This indicated that the ALFA$^{ST}$ tag was compatible with the formation of this labile membrane complex. Importantly, the native and non-modified membrane protein complex could be recovered from ALFA Selector$^{PE}$ resin within 20 min under physiological conditions using 200 µM of ALFA$^{ST}$ peptide. YfgM and its interaction partner PpiD specifically associated with ALFA Selector$^{PE}$ via the ALFA$^{ST}$ tag present on the (periplasmic) C-terminus of YfgM, as the complex could not be purified from a control lysate expressing non-tagged YfgM. The ALFA$^{ST}$ tag together with the ALFA Selector$^{PE}$ resin can thus not only be used for purification of proteins from various sources, it is also suited for native pull-downs of challenging (membrane) protein complexes.

Example 15: Isolation of Live Lymphocytes

Figure 12A:
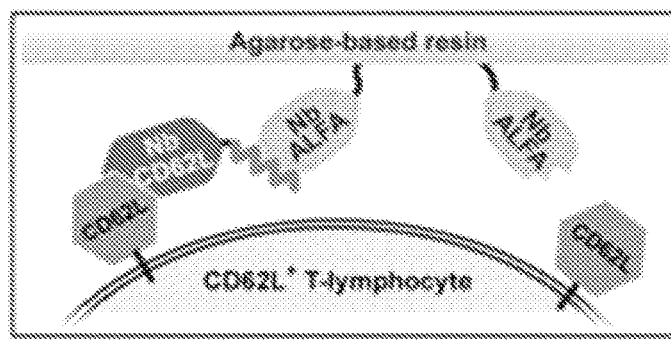
Figure 12B:
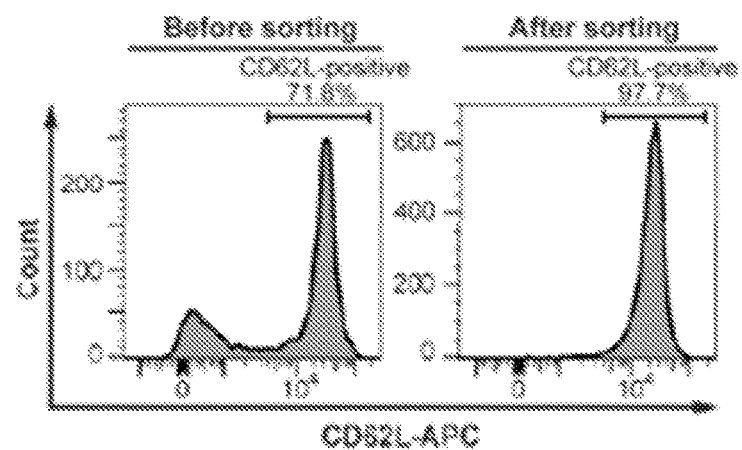
Figure 12C:
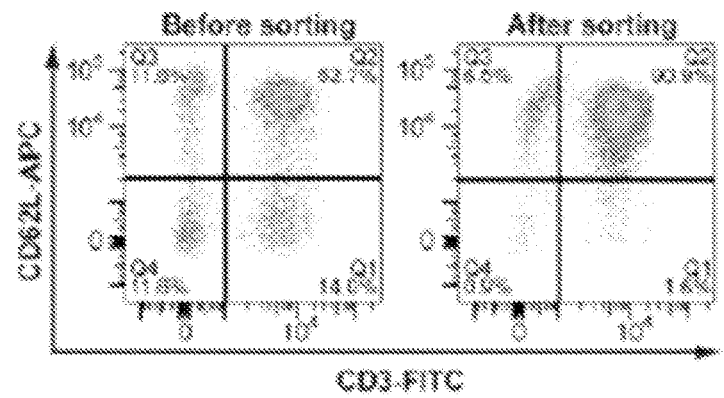
Figure 12D:
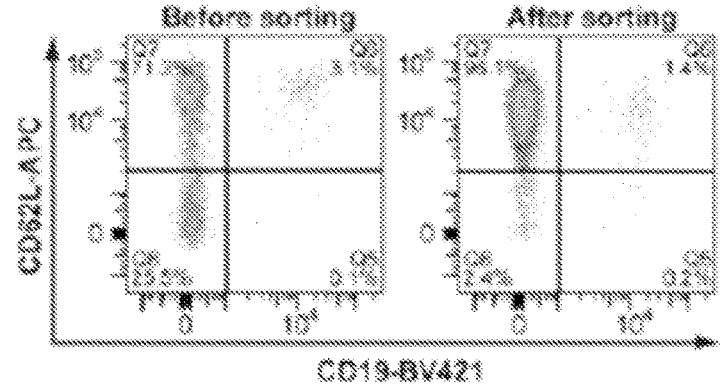

An envisioned application for the ALFA Selector$^{PE}$ is the specific enrichment of cells under physiological conditions. This may be particularly interesting e.g. for the generation of chimeric antigen receptor-modified T (CAR-T) cells, the precursors of which are usually obtained from blood (Tokarew, N. et al. Teaching an old dog new tricks: next-generation CAR T cells. Br. J. Cancer (2018). doi:10.1038/s41416-018-0325-1). To investigate if the ALFA system can be applied to enrich live blood cells, human peripheral blood mononuclear cells (PBMCs) were passed through an ALFA Selector$^{PE}$ column pre-charged with an ALFA-tagged nanobody recognizing CD62L, a surface marker typically present on naïve T cells (Lefrangois, L. Development, trafficking, and function of memory T-cell subsets. Immunological Reviews (2006). doi:10.1111/j.0105-2896.2006.00393.x) (FIG. 12a). After washing, bound cells were eluted using ALFA$^{ST}$ peptide, stained with antibodies recognizing CD62L, the pan T cell marker CD3 and the pan B cell marker CD19, and analyzed by FACS (FIG. 12). Total PBMCs served as a control. Using this strategy, CD62L+ lymphocytes were enriched from 71.8 to 97.7% (FIG. 12b). In addition, we confirmed that the vast majority of ALFA peptide-eluted cells were CD3-positive T cells, while B cells represented a minor population of the isolated cells (FIG. 12c).

Discussion

We reported the development and initial characterization of the ALFA system. This system comprises the ALFA$^{ST}$ tag, a novel and highly versatile epitope tag, a mutant variant thereof (ALFA$^{PE}$ tag) and a set of related single-domain antibodies (nanobodies) recognizing the ALFA$^{ST}$ tag with extraordinarily high or moderate affinity, respectively. Importantly, the rational approach chosen allowed us to equip the ALFA system with features that are crucial for its generic applicability. When selecting the ALFA tag sequences, it was preferred that the tag was small, devoid of lysines, hydrophilic without carrying any net charge and absent within the proteome of relevant model organisms, but also that it would adopt a stable fold in solution. As a result, the ALFA tags are preferably by design highly specific, insensitive to amine-reactive fixatives, generally well tolerated by the tagged target proteins and can easily refold after denaturation.

As binders we preferred nanobodies, because in contrast to conventional antibodies they are small, monovalent and robust probes that can easily be modified by genetic means and recombinantly produced in various expression systems. It is therefore possible to site-specifically immobilize nanobodies or to quantitatively introduce fluorescent labels (Pleiner, T. et al. Nanobodies: site-specific labeling for super-resolution imaging, rapid epitope-mapping and native protein complex isolation. Elife 4, (2015)). NbALFA$^{ST}$, our preferred high affinity nanobody recognizing the ALFA$^{ST}$ tag, can thus readily be used e.g. for direct immunofluorescence. Due to the small size of the nanobodies (~3-4 nm diameter) and the defined number and location of the attached dyes, fluorescently labeled NbALFA$^{ST}$ is an ideal tool for high-resolution or quantitative imaging. We could show that NbALFA$^{ST}$ faithfully interacts with various ALFA$^{ST}$-tagged target proteins expressed in mammalian cells. Importantly, NbALFA$^{ST}$ can even fold in the cytoplasm of eukaryotic cells and can thus be used as an "intrabody" for detecting or manipulating ALFA-tagged target proteins in vivo (Rothbauer, U. et al. Targeting and tracing antigens in live cells with fluorescent nanobodies. Nat Methods 3, 887-889 (2006); Kirchhofer, A. et al. Modulation of protein properties in living cells using nanobodies. Nat Struct Mol Biol 17, 133-138 (2010); Röder, R. et al. Intracellular Delivery of Nanobodies for Imaging of Target Proteins in Live Cells. Pharm. Res. (2016). doi:10.1007/s11095-016-2052-8). This finding is in line with our biochemical evidence showing that NbALFA$^{ST}$ is resistant to at least 100 mM DTT at room temperature and suggests that the conserved internal disulfide bridge common to all nanobodies is largely dispensable for a faithful interaction with the ALFA$^{ST}$ tag. For intrabody applications, we found that expression of both, NbALFA$^{ST}$ fused to a fluorescent reporter and target proteins under the control of a CMV or PGK promoter, led to good results with low background. For optimal results or detection of low-abundant ALFA$^{ST}$-tagged target proteins, more sophisticated titrations of the relative expression levels may be required.

Generally, most nanobodies recognize three-dimensional epitopes on the surface of their target proteins and thus do not recognize denatured proteins (e.g. in Western-Blots). We could show that NbALFA$^{ST}$ is an exception from this rule as it can also be used for highly sensitive target protein detection in Western-Blot applications. This fact suggests that the ALFA$^{ST}$ and ALFA$^{PE}$ tags can efficiently refold after transfer to the membrane and removal of SDS. A direct comparison showed that—despite its monovalent binding mode—NbALFA$^{ST}$ significantly outperformed established monoclonal anti-epitope tag tools with respect to absolute signal intensities and detection limit. We envision similar advantages in other applications like ELISA or microarray assays that require high sensitivity. Due to the resistance to amine-reactive fixatives, we believe it will be possible to also adapt the ALFA system to immuno-EM applications in the future.

The affinity of NbALFA$^{ST}$ for the ALFA$^{ST}$ tag is extraordinarily high. While this is ideal for high profile imaging applications and highly sensitive detection, it prevents an elution under physiological conditions within a reasonable time frame and thus sets limits for biochemical applications. We therefore aimed at lowering the affinity of the nanobody for its substrate without affecting its specificity. We approached this on two separate ways: 1) We screened a large selection of ALFA peptides for reduced binding strength. This approach led to the ALFA$^{PE}$ tag, which binds efficiently to NbALFA$^{ST}$ but can efficiently be eluted by competition with free ALFA$^{ST}$ peptide. 2) Based on the crystal structure of NbALFA$^{ST}$ in complex with the ALFA$^{ST}$ peptide, we introduced specific mutations in NbALFA$^{ST}$ that successfully increased the off-rate to a level allowing for an efficient peptide elution under physiological conditions. When immobilized to an agarose resin with low background binding, the mutant nanobody (NbALFA$^{PE}$) proved to be ideally suited for native purifications of proteins and protein complexes from various lysates under physiological conditions. ALFA Selector$^{ST}$ displaying the wild-type high affinity nanobody (NbALFA$^{ST}$), in turn, might have advantages in special applications requiring harsh washing with up to 6M urea or up to 0.1% SDS, or when extremely low-abundant proteins need to be depleted from dilute lysates. Elution from ALFA Selector$^{ST}$, however, requires strongly denaturing or acidic elution (e.g. 1% SDS or Glycin pH2.2), which is in general incompatible with a native target protein conformation.

The structure of NbALFA$^{ST}$ bound to the ALFA$^{ST}$ peptide shows that NbALFA$^{ST}$ recognizes the ALFA$^{ST}$ peptide in its alpha-helical conformation. In order to minimize the potential influences of neighboring secondary structures on the conformation of the ALFA$^{ST}$ tag, we placed the core ALFA$^{ST}$ sequence (SRLEEELRRRLTE, SEQ ID NO: 04)) between two prolines acting as "insulators". Using this approach, the interaction of NbALFA$^{ST}$ with the ALFA$^{ST}$ tag is largely independent of the tag's localization within the protein, i.e. both NbALFA$^{ST}$ and NbALFA$^{PE}$ will recognize ALFA$^{ST}$ tags placed both at the N- and C-terminus of a target protein or even within two protein domains.

Taken together, we here introduced a novel epitope tag system with exceptionally broad applicability. Using the ALFA system, a single transgenic cell line or organism harboring an ALFA$^{ST}$-tagged target protein is sufficient for a wealth of different applications including (super-resolution) imaging, in-vivo manipulation of proteins, in-vitro detection by Western-blot or even native pull-down applications aiming at detecting specific interaction partners. ALFA Selector$^{PE}$ could even be applied for the selective enrichment of CD62L-positive lymphocytes from PBMC preparations (FIG. 12). We believe that this technique can easily be transferred to the highly validated recombinant Fab and scFv fragments that are currently used for cell isolation approaches and similar purposes (Mohr, F. et al. Minimally manipulated murine regulatory T cells purified by reversible Fab Multimers are potent suppressors for adoptive T-cell therapy. Eur. J. Immunol. (2017). doi:10.1002/eji.201747137), or to novel nanobodies recognizing surface markers that can easily be equipped with an ALFA tag. Our new technology can therefore contribute to current advances in biomedical research and therapy including the CAR-T technology (Tokarew, N. et al. Teaching an old dog new tricks: next-generation CAR T cells. Br. J. Cancer (2018). doi:10.1038/s41416-018-0325-1). We strongly believe that due to the wide range of applications the ALFA system is an important contribution that will significantly stimulate the scientific community.

Material and Methods

Transfection of 3T3 and COS-7 Cells

For immunofluorescence experiments, 3T3 or COS-7 cells were transiently transfected with appropriate plasmids listed in Table 3, using the PolyJet transfection kit (SignaGen) according to the manufacturers recommendations. In short, for each experiment cells were seeded on 12-well plates. Volumes were adjusted according to the size of the well. 1 µg of each plasmid was premixed with 38 µl of serum-free medium and subsequently supplemented with PolyJet transfection reagent diluted in 38 µl of serum-free medium. The suspension was incubated at room temperature for 15 min and afterwards added drop-wise to the cells. Cells were incubated for 24 h at 37° C. with 5% CO$_2$. For co-expression experiments, plasmid DNA was premixed in a 1:1 ratio and further processed as described above.

Fixation and Staining of COS-7 Cells

Transiently transfected cells were fixed 24 h post transfection in either 4% paraformaldehyde (PFA) (w/v) or 2% glutaraldehyde (GA) (v/v) for 30 min at room-temperature. Alternatively, fixation was performed in ice cold methanol for 15 min at −20° C. Cells were blocked and permeabilized in PBS containing 10% normal goat serum (v/v) and 0.1% Triton-X 10 (v/v) for 15 min at room temperature. Fluorescently labeled NbALFA$^{ST}$(FluoTag-X2 anti-ALFA AbberiorStar635P, NanoTag Biotechnologies N1502-Ab635P-L) was diluted 1:500 in PBS containing 3% normal goat serum and 0.1% Triton-X 100 (v/v). The cells were incubated in this staining solution for 1 h at room temperature and subsequently washed 3 times for 5 min with PBS. To stain the nucleus, DAPI (0.4 µg/ml) was included in one of the PBS washing steps. Coverslips were mounted on cover-slides using MOWIOL solution, dried at 37° C. and imaged using an epifluorescence microscope (Axio, Zeiss) equipped with a 20× lens. Constructs expressed at the cell-surface were co-stained with anti-FLAG M2 (primary antibody, Sigma, F1804) and FluoTag-X2 anti-mouse IgG Atto488 (secondary nanobody, NanoTag, N1202-At488-L) diluted 1:1000 and 1:500 respectively, in PBS containing 3% normal goat serum and 0.1% Triton-X 100 (v/v).

Impact of ALFA Tags on the Localization of EGFP

Transiently transfected 3T3 cells were imaged using an epifluorescence microscope (Axio, Zeiss) equipped with a 40×1.3 oil lens. For cells transfected with either pCMV ALFA$^{ST}$-EGFP, pCMV EGFP-ALFA$^{ST}$, or pEGFP-N1, 107-133 cells were imaged on a total of six to seven individual images. For each individual image, cells were grouped and counted according to the localization of EGFP ("slightly nuclear", "equally distributed", "other"). The fraction of cells in each group was statistically analyzed using Student's t-test.

Western Blots with COS-7 Lysates

Transfected cells from a confluent 10 cm petri dish were washed with PBS and lysed in 2 mL SDS sample buffer. Lysates were resolved by SDS-PAGE and transferred to a nitrocellulose membrane. After blocking with 5% milk powder in TBS-T, membranes were incubated with mouse anti-tubulin (SYSY #302 211; 1:1000 dilution) followed by a FluoTag-X2 anti-Mouse IgG IRDye680 (NanoTag Biotechnologies #N1202; 1:1000 dilution) and FluoTag-X2 anti-ALFA IRDye800 (NanoTag Biotechnologies #1502; 1:1000 dilution). Membranes were scanned using Odyssey CLx (Li-COR).

Sensitivity Assay

A serial dilution of MBP fused to FLAG, HA, myc and ALFA$^{ST}$ tags was prepared in PBS pH7.4, 0.1 µg/mL BSA. 1 µl of each dilution was spotted on nitrocellulose membranes.

The membrane was blocked and washed with 5% milk powder in TBS-T. Established monoclonal antibodies (anti-FLAG M2—Sigma #F1804, anti-myc 9E10—SynapticSystems #343 011, anti-HA F-7—SantaCruz #sc-7392) were used in combination with a secondary goat anti-mouse IgG IRDye800CW (Li-COR #925-32210, dilution 1:500) to detect FLAG, myc and HA-tag, respectively. The ALFA$^{ST}$ tag was detected using a FluoTag-X2 anti-ALFA (NanoTag Biotechnologies #N1502) directly coupled to IRDye800CW. All primary antibodies and the nanobody were used at 2.7 nM final concentration. Detection of MBP by a rabbit polyclonal serum recognizing MBP (SynapticSystems) and an anti-rabbit IgG IRDye680RD (Li-COR #925-68071) served as an internal loading control. Membranes were scanned using Odyssey CLx (Li-COR). Quantifications were performed using ImageStudioLight (Li-COR).

Off-Rate Assays

20 µl ALFA Selector$^{ST}$ or ALFA Selector$^{PE}$ (NanoTag Biotechnologies) was saturated with the respective recombinant target protein. After washing 4× with PBS, the beads were suspended in a 10-fold excess of PBS containing 200 µM free ALFA$^{ST}$ peptide and mixed at 25° C. Control reactions were carried out without peptide. At indicated time points, specific elution from the beads was quantified using the GFP fluorescence released into the supernatant (Q-Bit 3.0; Thermo-Fischer Scientific). Three independent experiments were performed in parallel. Mean values, standard deviations and exponential fits were calculated using GraphPad Prism 5.0. Photographic pictures were taken upon UV illumination using a Nikon D700 equipped with a 105 mm macro lens (Nikon).

Resistance Towards Stringent Washing and pH

Depending on the experiment, 10-15 µl of ALFA Selector$^{ST}$ or ALFA Selector$^{PE}$ saturated with indicated ALFA-tagged shGFP2 fusion proteins were washed with PBS and incubated with 100 µl of the indicated substances for 60 min at room temperature. Photos were taken after sedimentation of the beads upon UV illumination. To assay for pH resistance, the same beads were incubated with 150 mM NaCl buffered to various pH (100 mM Glycin-HCl, pH2.2; 100 mM Na-Acetate pH4.5, 100 mM Tris-HCl pH 7.5, 100 mM Carbonate pH9.5) for 30 min at RT. The resin was washed twice with the same buffer. Photos were taken after equilibrating several times with PBS.

One-Step Affinity Purifications Using the ALFA Selector Resins.

To obtain defined input materials for pull-down experiments from E. coli or HeLa lysates, respective mock lysates were blended with 3 µM of the indicated purified ALFA-tagged shGFP2 variant. 1 mL of each lysate/substrate mixture was incubated with 25 µl of ALFA Selector$^{ST}$ or ALFA Selector$^{PE}$ for 1 h at 4° C. Depending on the experimental setup, either an analogous resin without immobilized sdAb (Selector Control) or a mock lysate without target protein served as a specificity control. After washing 3 times with 600 µL of PBS, the resins were transferred into MiniSpin columns (NanoTag Biotechnologies). Excess buffer was removed by centrifugation (3000×g, 30 sek) before incubating twice for 10 min at room temperature with 50 µl each of 200 µM ALFA$^{ST}$ peptide in PBS. Proteins remaining on the beads were afterwards eluted with SDS sample buffer. 0.5 µL (E. coli) or 1.5 µL (HeLa) of input and non-bound fractions were resolved by SDS-PAGE (12%) and Coomassie staining. Shown eluate fractions correspond to the material eluted from 1 µl of the respective resins.

YfgM Pull-Downs Using ALFA Selector$^{PE}$

A yfgM deletion strain was complemented with either C-terminally ALFA$^{ST}$-tagged or untagged YfgM expressed from a pSC-based low-copy vector under control of the endogenous promoter. Membrane protein complexes were solubilized from total lysates prepared in buffer LS (50 mM Tris pH7.5, 300 mM NaCl, 5 mM MgCl$_2$) using 1% DDM within 1 h on ice (Maddalo, G. et al. Systematic analysis of native membrane protein complexes in Escherichia coli. J Proteome Res 10, 1848-1859 (2011)). Both lysates were incubated with 20 µl of ALFA Selector$^{PE}$ resin for 1 h at 4° C. on a roller drum. After washing in PBS+0.3% DDM, bound proteins were eluted under native conditions by sequentially incubating twice with 50 µl PBS containing 200 µM ALFA$^{ST}$ peptide. Samples corresponding to 1/800 of the input and non-bound material or 1/80 of eluate fractions were resolved by SDS-PAGE. Analysis was performed by Western-blotting using a polyclonal rabbit antiserum raised against the YfgM-PpiD complex (Götzke, H. et al. YfgM is an ancillary subunit of the SecYEG translocon in *Escherichia coli*. J Biol Chem 289, 19089-19097 (2014)) followed by an HRP-conjugated goat anti-rabbit IgG (Dianova). Blots were developed using the Western Lightning Plus-ECL Kit (Perkin Elmer) and imaged using a LAS 4000 mini luminescence imager (Fuji Film).

YfgM Pull-Down Using ALFA Selector$^{ST}$

A yfgM deletion strain was complemented with either C-terminally ALFA$^{PE}$-tagged or untagged YfgM expressed from a pSC-based low-copy vector under control of the endogenous promoter. Membrane protein complexes were solubilized from total lysates prepared in buffer LS (50 mM Tris pH7.5, 300 mM NaCl, 5 mM MgCl$_2$) using 1% DDM within 1 h on ice (Maddalo, G. et al. Systematic analysis of native membrane protein complexes in *Escherichia coli*. J Proteome Res 10, 1848-1859 (2011)). Both lysates were incubated with 20 µl of ALFA Selector$^{ST}$ resin for 1 h at 4° C. on a roller drum. After washing in PBS+0.3% DDM, bound proteins were eluted under native conditions by sequentially incubating twice with 50F1 PBS containing 200 µM ALFA$^{ST}$ peptide. Samples corresponding to 1/800 of the input and non-bound material or 1/80 of eluate fractions were resolved by SDS-PAGE. Analysis was performed by Western-blotting using a polyclonal rabbit antiserum raised against the YfgM-PpiD complex (Götzke, H. et al. YfgM is an ancillary subunit of the SecYEG translocon in *Escherichia coli*. J Biol Chem 289, 19089-19097 (2014)) followed by an HRP-conjugated goat anti-rabbit IgG (Dianova). Blots were developed using the Western Lightning Plus-ECL Kit (Perkin Elmer) and imaged using a LAS 4000 mini luminescence imager (Fuji Film).

TABLE 3

Plasmids

Transfection

| Identifier | Promoter | Encoded protein | Origin/Citation |
| --- | --- | --- | --- |
| pNT1112 | pCMV | ALFA$^{ST}$-FLAG-Vimentin | This application |
| pNT1077 | pCMV | ALFA$^{PE}$-FLAG-Vimentin | This application |
| pNT1076 | pPGK | Tom70-EGFP-ALFA$^{ST}$ | This application |
| pNT1178 | pPGK | Tom70-EGFP-ALFA$^{PE}$ | This application |
| pNT1066 | pCMV | EGFP-ALFA$^{ST}$-myc-TM | This application |
| pNT1004 | pCMV | NbALFA$^{ST}$-mScarlet-I | This application |
| pEGFP-N1 | pCMV | EGFP | Clontech |
| pNT1137 | pCMV | EGFP-ALFA$^{ST}$ | This application |
| pNT1135 | pCMV | ALFA$^{ST}$-EGFP | This application |

TABLE 3-continued

Plasmids

Bacterial expression

| Identifier | Encoded protein | Origin/Citation |
| --- | --- | --- |
| pNT1208 | His$_{14}$-bdSUMO-FLAG-HA-MBP-myc-ALFA$^{ST}$ | This application |
| pNT1177 | ALFA$^{ST}$-shGFP2-His$_6$ | This application |
| pNT1176 | ALFA$^{PE}$-shGFP2-His$_6$ | This application |
| pNT1050 | His$_{14}$-bdSUMO-shGFP2-ALFA$^{ST}$ | This application |
| pNT1116 | His$_{14}$-bdSUMO-shGFP2-ALFA$^{PE}$ | This application |
| pNT1063 | His$_{14}$-bdSUMO-ALFA$^{ST}$-shsfGFP | This application |
| pNT1115 | His$_{14}$-bdSUMO-ALFA$^{PE}$-shsfGFP | This application |
| pNT1209 | pSC YfgM-ALFA$^{ST}$ | This application |
| pNT1123 | pSC YfgM-ALFA$^{PE}$ | This application |
| pSC-yfgM | pSC YfgM (native promoter in pUA66) | (a) |
| pNT0076 | His$_{14}$-bdSUMO-TwinStrepTag-bdNEDD8-ALFA$_{min}$ | This application |

(a) Götzke, H. et al. YfgM is an ancillary subunit of the SecYEG translocon in *Escherichia coli*. J Biol Chem 289, 19089-19097 (2014)

*E. coli* Strains

*E. coli* MC4100 ΔyfgM ΔppiD (Götzke, H. et al. YfgM is an ancillary subunit of the SecYEG translocon in *Escherichia coli*. J Biol Chem 289, 19089-19097 (2014))

TABLE 4

Antibodies

| Antibody | Supplier | Order No |
| --- | --- | --- |
| FluoTag-X2 anti-ALFA AbberiorSTAR635P | NanoTag Biotechnologies | N1502-Ab635P |
| FluoTag-X2 anti-ALFA IRDye800CW | NanoTag Biotechnologies | N1502 (Custom) |
| FluoTag-X2 anti-Mouse IRDye680RD | NanoTag Biotechnologies | N1202 (Custom) |
| anti-FLAG M2 | Sigma | F1804 |
| anti-myc 9E10 | SynapticSystems | #343 011 |
| anti-HA F-7 | SantaCruz | #sc-7392 |
| Goat anti-rabbit IRDye680RD | Li-COR | #925-68071 |
| Goat anti-mouse IRDye800CW | Li-COR | #925-32210 |
| anti-Tubulin | SynapticSystems | #302 211 |
| polyclonal serum recognizing MBP | SynapticSystems | |
| goat anti-rabbit IgG HRP-conjugate | Dianova | #GAR/IgG(H + L)/PO |
| anti-YfgM/PpiD | (a) | |

(a) Götzke, H. et al. YfgM is an ancillary subunit of the SecYEG translocon in *Escherichia coli*. J Biol Chem 289, 19089-19097 (2014)

TABLE 5

Fusion proteins

| Identifier | Encoded protein | Sequence of encoded protein |
| --- | --- | --- |

Transfection

| pNT1112 | ALFA$^{ST}$-FLAG-Vimentin (SEQ ID NO: 180) | MPSRLEEELRRRLTEPDYKDDDDKGSTRSVSS SSYRRMFGGSGTSSRPSSNRSYVTTSTRTYSL GSALRPSTSRSLYSSSPGGAYVTRSSAVRLRS SVPGVRLLQDSVDFSLADAINTEFKNTRTNEK |

TABLE 5-continued

Fusion proteins

| Identifier | Encoded protein | Sequence of encoded protein |
|---|---|---|
| | | VELQELNDRFANYIDKVRFLEQQNKILLAELE<br>QLKGQGKSRLGDLYEEEMRELRRQVDQLTNDK<br>ARVEVERDNLAEDIMRLREKLQEEMLQREEAE<br>STLQSFRQDVDNASLARLDLERKVESLQEEIA<br>FLKKLHDEEIQELQAQIQEQHVQIDVDVSKPD<br>LTAALRDVRQQYESVAAKNLQEAEEWYKSKFA<br>DLSEAANRNNDALRQAKQESNEYRRQVQSLTC<br>EVDALKGTNESLERQMREMEENFALEAANYQD<br>TIGRLQDEIQNMKEEMARHLREYQDLLNVKMA<br>LDIEIATYRKLLEGEESRISLPLPTFSSLNLR<br>ETNLESLPLVDTHSKRTLLIKTVETRDGQVIN<br>ETSQHHDDLE |
| pNT1077 | ALFA$^{PE}$-FLAG-<br>Vimentin<br>(SEQ ID NO: 181) | MSGRLEEELRRRLSPDYKDDDDKGSTRSVSSS<br>SYRRMFGGSGTSSRPSSNRSYVTTSTRTYSLG<br>SALRPSTSRSLYSSSPGGAYVTRSSAVRLRSS<br>VPGVRLLQDSVDFSLADAINTEFKNTRTNEKV<br>ELQELNDRFANYIDKVRFLEQQNKILLAELEQ<br>LKGQGKSRLGDLYEEEMRELRRQVDQLTNDKA<br>RVEVERDNLAEDIMRLREKLQEEMLQREEAES<br>TLQSFRQDVDNASLARLDLERKVESLQEEIAF<br>LKKLHDEEIQELQAQIQEQHVQIDVDVSKPDL<br>TAALRDVRQQYESVAAKNLQEAEEWYKSKFAD<br>LSEAANRNNDALRQAKQESNEYRRQVQSLTCE<br>VDALKGTNESLERQMREMEENFALEAANYQDT<br>IGRLQDEIQNMKEEMARHLREYQDLLNVKMAL<br>DIEIATYRKLLEGEESRISLPLPTFSSLNLRE<br>TNLESLPLVDTHSKRTLLIKTVETRDGQVINE<br>TSQHHDDLE |
| pNT1067 | Tom70-EGFP-<br>ALFA$^{ST}$<br>(SEQ ID NO: 182) | MKSFITRNKTAILATVAATGTAIGAYYYYGNS<br>PVATMVSKGEELFTGVVPILVELDGDVNGHKF<br>SVSGEGEGDATYGKLTLKFICTTGKLPVPWPT<br>LVTTLTYGVQCFSRYPDHMKQHDFFKSAMPEG<br>YVQERTIFFKDDGNYKTRAEVKFEGDTLVNRI<br>ELKGIDFKEDGNILGHKLEYNYNSHNVYIMAD<br>KQKNGIKVNFKIRHNIEDGSVQLADHYQQNTP<br>IGDGPVLLPDNHYLSTQSKLSKDPNEKRDHMV<br>LLEFVTAAGITLGMDELYKGSPSRLEEELRRR<br>LTE |
| pNT1178 | Tom70-EGFP-<br>ALFA$^{PE}$<br>(SEQ ID NO: 183) | MKSFITRNKTAILATVAATGTAIGAYYYYGNS<br>PVATMVSKGEELFTGVVPILVELDGDVNGHKF<br>SVSGEGEGDATYGKLTLKFICTTGKLPVPWPT<br>LVTTLTYGVQCFSRYPDHMKQHDFFKSAMPEG<br>YVQERTIFFKDDGNYKTRAEVKFEGDTLVNRI<br>ELKGIDFKEDGNILGHKLEYNYNSHNVYIMAD<br>KQKNGIKVNFKIRHNIEDGSVQLADHYQQNTP<br>IGDGPVLLPDNHYLSTQSKLSKDPNEKRDHMV<br>LLEFVTAAGITLGMDELYKGSPSRLEEELRRR<br>LTE |
| pNT1066 | SS-HA-EGFP-<br>ALFA$^{ST}$-myc-TM<br>(SEQ ID NO: 184) | METDTLLLWVLLLWVPGSTGDYPYDVPDYASN<br>GTSKGEELFTGVVPILVELDGDVNGHKFSVSG<br>EGEGDATYGKLTLKFICTTGKLPVPWPTLVTT<br>LTYGVQCFSRYPDHMKQHDFFKSAMPEGYVQE<br>RTIFFKDDGNYKTRAEVKFEGDTLVNRIELKG<br>IDFKEDGNILGHKLEYNYNSHNVYIMADKQKN<br>GIKVNFKIRHNIEDGSVQLADHYQQNTPIGDG<br>PVLLPDNHYLSTQSALSKDPNEKRDHMVLKEF<br>VTAAGITLGMDELYKGSPSRLEEELRRRLTEP<br>GDEQKLISEEDLNAVGQDTQEVIVVPHSLPFK<br>VVVISAILALVVLTIISLIILIMLWQKKPR |
| pNT1004 | NbALFA$^{ST}$-<br>mScarlet-I<br>(SEQ ID NO: 185) | MGSGDASDSEVQLQESGGGLVQPGGSLRLSCT<br>ASGVTISALNAMAMGWYRQAPGERRVMVAAVS<br>ERGNAMYRESVQGRFTVTRDFTNKMVSLQMDN<br>LKPEDTAVYYCHVLEDRVDSFHDYWGQGTQVT<br>VSSEPKTPKPQTSGSTGENVATMVSKGEAVIK<br>EFMRFKVHMEGSMNGHEFEIEGEGEGRPYEGT<br>QTAKLKVTKGGPLPFSWDILSPQFMYGSRAFI<br>KHPADIPDYYKQSFPEGFKWERVMNFEDGGAV<br>TVTQDTSLEDGTLIYKVKLRGTNFPPDGPVMQ<br>KKTMGWEASTERLYPEDGVLKGDIKMALRLKD<br>GGRYLADFKTTYKAKKPVQMPGAYNVDRKLDI<br>TSHNEDYTVVEQYERSEGRHSTGGMDELYK |

TABLE 5-continued

Fusion proteins

| Identifier | Encoded protein | Sequence of encoded protein |
|---|---|---|
| pEGFP-N1 | EGFP (SEQ ID NO: 186) | MVSKGEELFTGVVPILVELDGDVNGHKFSVSG EGEGDATYGKLTLKFICTTGKLPVPWPTLVTT LTYGVQCFSRYPDHMKQHDFFKSAMPEGYVQE RTIFFKDDGNYKTRAEVKFEGDTLVNRIELKG IDFKEDGNILGHKLEYNYNSHNVYIMADKQKN GIKVNFKIRHNIEDGSVQLADHYQQNTPIGDG PVLLPDNHYLSTQSALSKDPNEKRDHMVLLEF VTAAGITLGMDELYK |
| pNT1137 | EGFP-ALFA$^{ST}$ (SEQ ID NO: 187) | *MVSKGEELFTGVVPILVELDGDVNGHKFSVSG EGEGDATYGKLTLKFICTTGKLPVPWPTLVTT LTYGVQCFSRYPDHMKQHDFFKSAMPEGYVQE RTIFFKDDGNYKTRAEVKFEGDTLVNRIELKG IDFKEDGNILGHKLEYNYNSHNVYIMADKQKN GIKVNFKIRHNIEDGSVQLADHYQQNTPIGDG PVLLPDNHYLSTQSALSKDPNEKRDHMVLLEF VTAAGITLGMDELYKGS*PSRLEEELRRRLTE |
| pNT1135 | ALFA$^{ST}$-EGFP (SEQ ID NO: 188) | MPSRLEEELRRRLTEP*MVSKGEELFTGVVPIL VELDGDVNGHKFSVSGEGEGDATYGKLTLKFI CTTGKLPVPWPTLVTTLTYGVQCFSRYPDHMK QHDFFKSAMPEGYVQERTIFFKDDGNYKTRAE VKFEGDTLVNRIELKGIDFKEDGNILGHKLEY NYNSHNVYIMADKQKNGIKVNFKIRHNIEDGS VQLADHYQQNTPIGDGPVLLPDNHYLSTQSAL SKDPNEKRDHMVLLEFVTAAGITLGMDELYK* |

Bacterial expression

| Identifier | Encoded protein | Sequence of encoded protein |
|---|---|---|
| pNT1208 | His$_{14}$-bdSUMO-FLAG-HA-MBP-myc-ALFA$^{ST}$ (SEQ ID NO: 189) | MSKHHHHSNHHRHNHHHHSGNHHHSGSAAGGE EDKKPAGGEGGGAHINLKVKGQDGNEVFFRIK RSTQLKKLMNAYCDRQSVDMTAIAFLFDGRRL RAEQTPDELEMEDGDEIDAMLHQTGGASDYKD DDDKGSTGDYPYDVPDYASNGTKTEEGKLVIW INGDKGYNGLAEVGKKFEKDTGIKVTVEHPDK LEEKFPQVAATGDGPDHFWAHDRFGGYAQSGL LAEITPDKAFQDKLYPFTWDAVRYNGKLIAYP IAVEALSLIYNKDLLPNPPKTWEEIPALDKEL KAKGKSALMFNLQEPYFTWPLIAADGGYAFKY ENGKYDIKDVGVDNAGAKAGLTFLVDLIKNKH MNADTDYSIAEAAFNKGETAMTINGPWAWSNI DTSKVNYGVTVLPTFKGQPSKPFVGVLSAGIN AASPNKELAKEFLENYLLTDEGLEAVNKDKPL GAVALKSYEEELAKDPRIAATMENAQKGEIMP NIPQMSAFWYAVRTAVINAASGRQTVDEALKD AQTNGSVSAGDEQKLISEEDLNAVGQDTASTP SRLEEELRRRLTE |
| pNT1177 | ALFA$^{ST}$-shGFP2-His$_6$ (SEQ ID NO: 190) | MPSRLEEELRRRLTEP*SKGEELFTGTVPIKVE LDGDVNGHKFSVRGEGEGDATEGKLTLKFICT TGKLPVPWPTLVTTLTYGVQCFSRYPDHMKRH DFFKSAMPEGYVQERTIEFKDDGTYKTRAEVK FEGDTLVNRIELKGNDFKEDGNILGHKLEYNH NSHNVRIEADKQKNGIKANFKIRHNVEDGSQQ EADHKQQNTPIGDGPVRLPDNHYLSTQTTLSK DPNEKRDHMVLKEFVTAAGITKGEDERDK*<u>HHH HHH</u> |
| pNT1176 | ALFA$^{PE}$-shGFP2-His$_6$ (SEQ ID NO: 191) | MSGRLEEELRRRLSP*SKGEELFTGTVPIKVEL DGDVNGHKFSVRGEGEGDATEGKLTLKFICTT GKLPVPWPTLVTTLTYGVQCFSRYPDHMKRHD FFKSAMPEGYVQERTIEFKDDGTYKTRAEVKF EGDTLVNRIELKGNDFKEDGNILGHKLEYNHN SHNVRIEADKQKNGIKANFKIRHNVEDGSQQE ADHKQQNTPIGDGPVRLPDNHYLSTQTTLSKD PNEKRDHMVLKEFVTAAGITKGEDERDK*<u>HHHH HH</u> |
| pNT1050 | His$_{14}$-bdSUMO-shGFP2-ALFA$^{ST}$ (SEQ ID NO: 192) | MSKHHHHSNHHRHNHHHHSGNHHHSGS<u>AAGGE EDKKPAGGEGGGAHINLKVKGQDGNEVFFRIK RSTQLKKLMNAYCDRQSVDMTAIAFLFDGRRL RAEQTPDELEMEDGDEIDAMLHQTGGG</u>SKGEE LFTGTVPIKVELDGDVNGHKFSVRGEGEGDAT EGKLTLKFICTTGKLPVPWPTLVTTLTYGVQC FSRYPDHMKRHDFFKSAMPEGYVQERTIEFKD |

TABLE 5-continued

Fusion proteins

| Identifier | Encoded protein | Sequence of encoded protein |
|---|---|---|
| | | DGTYKTRAEVKFEGDTLVNRIELKGNDFKEDG<br>NILGHKLEYNHNSHNVRIEADKQKNGIKANFK<br>IRHNVEDGSQQEADHKQQNTPIGDGPVRLPDN<br>HYLSTQTTLSKDPNEKRDHMVLKEFVTAAGIT<br>KGEDERDKGSGNSDGPSRLEEELRRRLTE |
| pNT1116 | His$_{14}$-bdSUMO-<br>shGFP2-ALFA$^{PE}$<br>(SEQ ID NO: 193) | MSKHHHHSNHHRHNHHHHSGNHHHSGSAAGGE<br>EDKKPAGGEGGGAHINLKVKGQDGNEVFFRIK<br>RSTQLKKLMNAYCDRQSVDMTAIAFLFDGRRL<br>RAEQTPDELEMEDGDEIDAMLHQTGGGSKGEE<br>LFTGTVPIKVELDGDVNGHKFSVRGEGEGDAT<br>EGKLTLKFICTTGKLPVPWPTLVTTLTYGVQC<br>FSRYPDHMKRHDFFKSAMPEGYVQERTIEFKD<br>DGTYKTRAEVKFEGDTLVNRIELKGNDFKEDG<br>NILGHKLEYNHNSHNVRIEADKQKNGIKANFK<br>IRHNVEDGSQQEADHKQQNTPIGDGPVRLPDN<br>HYLSTQTTLSKDPNEKRDHMVLKEFVTAAGIT<br>KGEDERDKGSGNSDGMSGRLEEELRRRLSP |
| pNT1063 | His$_{14}$-bdSUMO-<br>ALFA$^{ST}$-shsfGFP<br>(SEQ ID NO: 194) | MSKHHHHSNHHRHNHHHHSGNHHHSGSAAGGE<br>EDKKPAGGEGGGAHINLKVKGQDGNEVFFRIK<br>RSTQLKKLMNAYCDRQSVDMTAIAFLFDGRRL<br>RAEQTPDELEMEDGDEIDAMLHQTGGSGDASD<br>SPSRLEEELRRRLTEPSKGEELFTGTVPIKVE<br>LDGDVNGHKFSVRGEGEGDATEGKLTLKFICT<br>TGKLPVPWPTLVTTLTYGVQCFSRYPDHMKRH<br>DFFKSAMPEGYVQERTIEFKDDGTYKTRAEVK<br>FEGDTLVNRIELKGNDFKEDGNILGHKLEYNH<br>NSHNVRIEADKQKNGIKANFKIRHNVEDGSQQ<br>EADHKQQNTPIGDGPVRLPDNHYLSTQTTLSK<br>DPNEKRDHMVLKEFVTAAGITKGEDERDKA |
| pNT1115 | His$_{14}$-bdSUMO-<br>ALFA$^{PE}$-shsfGFP<br>(SEQ ID NO: 195) | MSKHHHHSNHHRHNHHHHSGNHHHSGSAAGGE<br>EDKKPAGGEGGGAHINLKVKGQDGNEVFFRIK<br>RSTQLKKLMNAYCDRQSVDMTAIAFLFDGRRL<br>RAEQTPDELEMEDGDEIDAMLHQTGGSGDASD<br>SMSGRLEEELRRRLSPSKGEELFTGTVPIKVE<br>LDGDVNGHKFSVRGEGEGDATEGKLTLKFICT<br>TGKLPVPWPTLVTTLTYGVQCFSRYPDHMKRH<br>DFFKSAMPEGYVQERTIEFKDDGTYKTRAEVK<br>FEGDTLVNRIELKGNDFKEDGNILGHKLEYNH<br>NSHNVRIEADKQKNGIKANFKIRHNVEDGSQQ<br>EADHKQQNTPIGDGPVRLPDNHYLSTQTTLSK<br>DPNEKRDHMVLKEFVTAAGITKGEDERDKA |
| pNT1209 | YfgM-ALFA$^{ST}$<br>(SEQ ID NO: 196) | MEIYENENDQVEAVKRFFAENGKALAVGVILG<br>VGALIGWRYWNSHQVDSARSASLAYQNAVTAV<br>SEGKPDSIPAAEKFAAENKNTYGALASLELAQ<br>QFVDKNELEKAAAQLQQGLADTSDENLKAVIN<br>LRLARVQVQLKQADAALKTLDTIKGEGWAAIV<br>ADLRGEALLSKGDKQGARSAWEAGVKSDVTPA<br>LSEMMQMKINNLSIGSPSRLEEELRRRLTE |
| pNT1123 | YfgM-ALFA$^{PE}$<br>(SEQ ID NO: 197) | MEIYENENDQVEAVKRFFAENGKALAVGVILG<br>VGALIGWRYWNSHQVDSARSASLAYQNAVTAV<br>SEGKPDSIPAAEKFAAENKNTYGALASLELAQ<br>QFVDKNELEKAAAQLQQGLADTSDENLKAVIN<br>LRLARVQVQLKQADAALKTLDTIKGEGWAAIV<br>ADLRGEALLSKGDKQGARSAWEAGVKSDVTPA<br>LSEMMQMKINNLSIGSMSGRLEEELRRRLS |
| pSC-yfgM | YfgM<br>(SEQ ID NO: 198) | MEIYENENDQVEAVKRFFAENGKALAVGVILG<br>VGALIGWRYWNSHQVDSARSASLAYQNAVTAV<br>SEGKPDSIPAAEKFAAENKNTYGALASLELAQ<br>QFVDKNELEKAAAQLQQGLADTSDENLKAVIN<br>LRLARVQVQLKQADAALKTLDTIKGEGWAAIV<br>ADLRGEALLSKGDKQGARSAWEAGVKSDVTPA<br>LSEMMQMKINNLSI |
| pNT0076 | His$_{14}$-bdSUMO-<br>TwinStrepTag-<br>bdNEDD8-ALFA$_{min}$<br>(SEQ ID NO: 199) | MSKHHHHSNHHRHNHHHHSGNHHHSGSAAGGE<br>EDKKPAGGEGGGAHINLKVKGQDGNEVFFRIK<br>RSTQLKKLMNAYCDRQSVDMTAIAFLFDGRRL<br>RAEQTPDELEMEDGDEIDAMLHQTGGACWSH<br>PQFEKGGGSGGSSGGSAWSHPQFEKGSGSAES<br>EAASSTMIKVKTLTGKEIEIDIEPTDTIDRIK<br>ERVEEKEGIPPVQQRLIYAGKQLADDKTAKDY |

TABLE 5-continued

Fusion proteins

| Identifier | Encoded protein | Sequence of encoded protein |
|---|---|---|
| | | NIEGGSVLHLVLALRGGATGTASTRLEEELRR<br>RLAS |

Protein Expression and Purification

All recombinant proteins were expressed under the control of the Tac-promoter from expression vectors with ColE1 origin that confer resistance to Kanamycin.

The MBP fusion protein harboring multiple epitope tags, ALFA$^{ST}$-shGFP2, ALFA$^{PE}$-shGFP2 and TwinStrepTag-bdNEDD8-ALFA$_{min}$ were expressed as N-terminal His$_{14}$-bdSUMO fusions. For protein expression, E. coli was cultured in Terrific broth (TB) supplemented with 0.3 mM IPTG for 14-16 h at 23° C. After harvest, E. coli cells were lysed in LS buffer (50 mM Tris/HCl pH 7.5, 300 mM NaCl) supplemented with 15 mM imidazole/HCl pH 7.5 and 10 mM DTT, and purified by binding to Ni(II)-chelate beads. After extensive washing, proteins were eluted by on-column-cleavage with bdSENP1 as described before (Frey, S. & Görlich, D. A new set of highly efficient, tag-cleaving proteases for purifying recombinant proteins. J Chromatogr A 1337, 95-105 (2014); Frey, S. & Görlich, D. Purification of protein complexes of defined subunit stoichiometry using a set of orthogonal, tag-cleaving proteases. J Chromatogr A 1337, 106-115 (2014)).

ALFA$^{ST}$-shGFP2-His$_6$, ALFA$^{PE}$-shGFP2-His$_6$, His$_{14}$-bdSUMO-ALFA$^{ST}$-shsfGFP and His$_{14}$-bdSUMO-ALFA$^{PE}$-shsfGFP were expressed and purified in a similar fashion; Elution was, however, performed using 250 mM Imidazole in buffer LS.

For affinity determinations and binding studies from complex lysates, substrate proteins were in addition purified via size exclusion chromatography on a Superdex200 10/30 column (GE Healthcare).

Selection of Specific sdAb Clones by Affinity Purification of B-Cells "Celline"

1 mL of T-Catch resin (IBA Lifesciences) was washed with B cell isolation buffer (PBS pH7.4, 1% BSA, 1 mM EDTA) and incubated with saturating amounts of a TwinStrepTag-bdNEDD8-ALFA$_{min}$ fusion protein for 30 min rolling at RT. The resins were cleared form excess bait protein by extensively washing with B cell isolation buffer. 100 mL of blood sample was taken from alpaca immunized with ALFA peptide fusions and immediately incubated with 5000 IU/mL heparin (Sigma) to prevent clotting. From the fresh blood (less than 4 h past sampling) PBMCs were isolated using Ficoll-Paque PLUS (GE Healthcare). To remove residual serum, PBMCs were washed three times consecutively with B cell isolation buffer. PBMCs were passed over the loaded T-Catch resin for three times before washing the resins with 10 column volumes B cell isolation buffer. Bound B cells were eluted from the resins by incubating 2 µM NEDP1 (Frey, S. & Görlich, D. A new set of highly efficient, tag-cleaving proteases for purifying recombinant proteins. J Chromatogr A 1337, 95-105 (2014); Frey, S. & Görlich, D. Purification of protein complexes of defined subunit stoichiometry using a set of orthogonal, tag-cleaving proteases. J Chromatogr A 1337, 106-115 (2014)) for 30 min at RT. From the eluted B cells an sdAb-specific cDNA library was amplified by a multistep nested RT-PCR and cloned into a bacterial expression vector. 96 single clones were tested by ELISA for expression of ALFA-reactive sdAbs.

Preparation of Human PBMCs

Human peripheral blood mononuclear cells (PBMCs) were obtained from fresh blood using standard density gradient centrifugation. Briefly, 60 mL of fresh blood were diluted with 40 mL of phosphate-buffered saline (PBS) supplemented with 1 mM EDTA and placed on top of a layer of CELLPURE Roti-Sep 1077 (Carl Roth) in 50 mL LEUCOSEP tubes (Greiner Bio-One) and centrifuged at 800×g for 20 minutes at room temperature. Subsequently, the PBMC-containing layer was collected and washed five times in cold PBS+EDTA to remove platelets.

Isolation of CD62L-Positive Lymphocytes

Approximately 2×10$^7$ PBMCs were passed by gravity flow through an ALFA Selector$^{PE}$ resin loaded with an ALFA-tagged anti-human CD62L nanobody, followed by extensive washing with PBS supplemented with 1 mM EDTA 1 and 1% (w/v) bovine serum albumin. Subsequently, bound cells were eluted in the same buffer containing 200 µM ALFA peptide.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A single domain antibody that is capable of binding a peptide having the sequence SRLEEELRRRLTE (SEQ ID NO: 04), wherein the antibody comprises CDR1, CDR2, and CDR3 sequences selected from the group consisting of:
   (a) a CDR1 sequence having the sequence of GVTISAL-NAMAMG (SEQ ID NO: 115), a CDR2 sequence having the sequence of AVSERGNAM (SEQ ID NO: 116), and a CDR3 sequence having the sequence of LEDRVDSFHDY (SEQ ID NO: 117); and
   (b) a CDR1 sequence having the sequence of GVTISAL-NAMAMG (SEQ ID NO: 115), a CDR2 sequence having the sequence of AVSSRGNAM (SEQ ID NO: 119), and a CDR3 sequence having the sequence of LEDRVDSFHDY (SEQ ID NO: 117).

2. The antibody of claim 1, comprising a camelid single variable domain of a heavy chain (VHH) sequence having at least 95%, sequence identity to (SEQ ID NO: 133)
EVQLQESGGGLVQPGGSLRLSCTASGVTISALNAMAMGWYRQAPGERRV
MVAAVSERGNAMYRESVQGRFTVTRDFTNKMVSLQMDNLKPEDTAVYYC
HVLEDRVDSFHDYWGQGTQVTVSS; or (SEQ ID NO: 134)
EVQLQESGGGLVQPGGSLRLSCTASGVTISALNAMAMGWYRQAPGEERV
MVAAVSSRGNAMYRESVQGRFTVTRDFTNKMVSLQMDNLKPEDTAVYYC
HVLEDRVDSFHDYWGQGTQVTVSS.

3. The antibody of claim 1, wherein the antibody is conjugated to a detectable label, an affinity tag, or a solid support.

4. The antibody of claim 1, wherein the antibody is in a complex with a fusion protein that comprises
   (a) a peptide P having the sequence of SRLEEELRRRLTE (SEQ ID NO: 04); and
   (b) a polypeptide.

5. The antibody of claim 1, wherein the antibody comprises: the CDR1 sequence GVTISALNAMAMG (SEQ ID NO: 115), the CDR2 sequence AVSERGNAM (SEQ ID NO: 116), and the CDR3 sequence LEDRVDSFHDY (SEQ ID NO: 117).

6. The antibody of claim 1, wherein the antibody comprises: the CDR1 sequence GVTISALNAMAMG (SEQ ID NO: 115), the CDR2 sequence AVSSRGNAM (SEQ ID NO: 119), and the CDR3 sequence LEDRVDSFHDY (SEQ ID NO: 127).

7. The antibody of claim 1, comprising a camelid single variable domain of a heavy chain (VHH) sequence having the sequence of (SEQ ID NO: 133)
EVQLQESGGGLVQPGGSLRLSCTASGVTISALNAMAMGWYRQAPGERRV
MVAAVSERGNAMYRESVQGRFTVTRDFTNKMVSLQMDNLKPEDTAVYYC
HVLEDRVDSFHDYWGQGTQVTVSS; or (SEQ ID NO: 134)
EVQLQESGGGLVQPGGSLRLSCTASGVTISALNAMAMGWYRQAPGEERV
MVAAVSSRGNAMYRESVQGRFTVTRDFTNKMVSLQMDNLKPEDTAVYYC
HVLEDRVDSFHDYWGQGTQVTVSS.

8. The single domain antibody of claim 1, wherein the antibody binds the peptide having the sequence SRLEEELRRRLTE (SEQ ID NO: 04) with a $K_D$ of $10^{-6}$ M or lower.

9. The single domain antibody of claim 1, wherein the antibody binds the peptide having the sequence SRLEEELRRRLTE (SEQ ID NO: 04) with a $K_D$ of 30 nM or lower.

10. A single domain antibody comprising the VHH sequence selected from the group consisting of:

(a)
(SEQ ID NO: 133)
EVQLQESGGGLVQPGGSLRLSCTASGVTISALNAMAMGWYRQAPGERRV
MVAAVSERGNAMYRESVQGRFTVTRDFTNKMVSLQMDNLKPEDTAVYYC
HVLEDRVDSFHDYWGQGTQVTVSS; and (b)
(SEQ ID NO: 134)
EVQLQESGGGLVQPGGSLRLSCTASGVTISALNAMAMGWYRQAPGEERV
MVAAVSSRGNAMYRESVQGRFTVTRDFTNKMVSLQMDNLKPEDTAVYYC
HVLEDRVDSFHDYWGQGTQVTVSS.

11. The antibody of claim 10, comprising the VHH sequence of (SEQ ID NO: 133)
EVQLQESGGGLVQPGGSLRLSCTASGVTISALNAMAMGWYRQAPGERRV

MVAAVSERGNAMYRESVQGRFTVTRDFTNKMVSLQMDNLKPEDTAVYYC

HVLEDRVDSFHDYWGQGTQVTVSS.

12. The antibody of claim 10, comprising the VHH sequence of (SEQ ID NO: 134)
EVQLQESGGGLVQPGGSLRLSCTASGVTISALNAMAMGWYRQAPGEERV

MVAAVSSRGNAMYRESVQGRFTVTRDFTNKMVSLQMDNLKPEDTAVYYC

HVLEDRVDSFHDYWGQGTQVTVSS.

13. The antibody of claim 10, wherein the antibody is conjugated to a detectable label, an affinity tag, or a solid support.

* * * * *